(12) United States Patent
Baugh et al.

(10) Patent No.: US 7,285,609 B2
(45) Date of Patent: *Oct. 23, 2007

(54) OLEFIN POLYMERIZATION CATALYST SYSTEM USEFUL FOR POLAR MONOMERS

(75) Inventors: Lisa Saunders Baugh, Ringoes, NJ (US); Enock Berluche, Phillipsburg, NJ (US); Paul Veinbergs Hinkle, Wallingford, PA (US); Francis Charles Rix, League City, TX (US); Donald Norman Schulz, Annandale, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/844,683

(22) Filed: May 13, 2004

(65) Prior Publication Data

US 2004/0260043 A1 Dec. 23, 2004

Related U.S. Application Data

(63) Continuation-in-part of application No. 10/436,741, filed on May 13, 2003.

(51) Int. Cl.
C08F 4/44 (2006.01)
B01J 31/38 (2006.01)

(52) U.S. Cl. .................. 526/161; 526/171; 526/172; 526/348; 502/155; 502/167

(58) Field of Classification Search ................ 526/161, 526/171, 172, 348; 502/155, 167
See application file for complete search history.

(56) References Cited

U.S. PATENT DOCUMENTS

| | | | |
|---|---|---|---|
| 6,037,297 A | 3/2000 | Stibrany et al. | |
| 6,143,857 A | 11/2000 | Bansleben et al. | |
| 6,147,173 A | 11/2000 | Holtcamp | |
| 6,147,174 A | 11/2000 | Holtcamp et al. | |
| 6,180,788 B1 | 1/2001 | Stibrany | |
| 6,197,714 B1 | 3/2001 | Bansleben et al. | |
| 6,197,715 B1 | 3/2001 | Bansleben et al. | |
| 6,211,105 B1 | 4/2001 | Holtcamp | |
| 6,258,903 B1 | 7/2001 | Mawson et al. | |
| 6,265,505 B1 | 7/2001 | McConville et al. | |
| 6,265,513 B1 | 7/2001 | Murray et al. | |
| 6,268,447 B1 | 7/2001 | Murray et al. | |
| 6,281,306 B1 | 8/2001 | Oskam et al. | |
| 6,320,002 B1 | 11/2001 | Murray et al. | |
| 6,333,389 B2 | 12/2001 | Whiteker et al. | |
| 6,340,730 B1 | 1/2002 | Murray et al. | |
| 6,346,584 B1 | 2/2002 | Wenzel et al. | |
| 6,372,868 B1 | 4/2002 | Szul et al. | |
| 6,380,328 B1 | 4/2002 | McConville et al. | |
| 6,399,722 B1 | 6/2002 | Szul et al. | |
| 6,410,664 B1 | 6/2002 | Bansleben et al. | |
| 6,417,303 B1 | 7/2002 | Stibrany et al. | |
| 6,506,704 B1 | 1/2003 | Bansleben et al. | |
| 6,562,922 B1 | 5/2003 | Bansleben et al. | |
| 6,897,275 B2* | 5/2005 | Wang et al. | 526/161 |
| 6,962,890 B2* | 11/2005 | Matsukawa et al. | 526/161 |
| 2004/0171479 A1 | 9/2004 | Bazan et al. | 502/102 |
| 2004/0181018 A1 | 9/2004 | Weiss | |

FOREIGN PATENT DOCUMENTS

DE 99 556 8/1973

(Continued)

OTHER PUBLICATIONS

Grubbs et al., Science vol. 287 (Jan. 27, 2000).*

(Continued)

*Primary Examiner*—Robert D. Harlan
(74) *Attorney, Agent, or Firm*—Catherine L. Bell

(57) ABSTRACT

This invention relates to a polymerization method comprising contacting at least one olefin monomer, at least one polar monomer, an optional activator, and a catalyst compound represented by the formula:

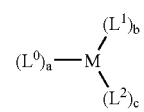

wherein M is selected from groups 3-11 of the periodic table;

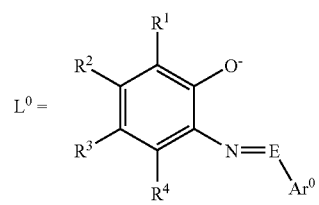

$L^1$ represents a formal anionic ligand, $L^2$ represents a formal neutral ligand, a is an integer greater than or equal to 1; b is greater than or equal to 0; c is greater than or equal to 1,
E is nitrogen or phosphorus, $Ar^0$ is arene, $R^1$-$R^4$ are, each independently, selected from hydrogen, hydrocarbyl, substituted hydrocarbyl or functional group, provided however that $R^3$ and $R^4$ do not form a naphthyl ring, N is nitrogen and O is oxygen.

50 Claims, No Drawings

FOREIGN PATENT DOCUMENTS

| EP | 0 990 664 | 4/2000 |
|---|---|---|
| EP | 1 217 013 | 6/2002 |
| WO | 96/23010 | 8/1996 |
| WO | 98/30609 | 7/1998 |
| WO | 98/42664 | 10/1998 |
| WO | 98/42665 | 10/1998 |
| WO | WO99/05189 | 2/1999 |
| WO | 99/30822 | 6/1999 |
| WO | 00/04058 | 1/2000 |
| WO | 00/15676 | 3/2000 |
| WO | 00/29454 | 5/2000 |
| WO | 00/35969 | 6/2000 |
| WO | 00/37509 | 6/2000 |
| WO | 00/37511 | 6/2000 |
| WO | 00/37512 | 6/2000 |
| WO | 00/56781 | 9/2000 |
| WO | 00/56785 | 9/2000 |
| WO | 00/56786 | 9/2000 |
| WO | 00/56787 | 9/2000 |
| WO | 01/30860 | 5/2001 |
| WO | 01/30861 | 5/2001 |
| WO | 01/30862 | 5/2001 |
| WO | 01/40325 | 6/2001 |
| WO | 01/40330 | 6/2001 |
| WO | 01/44321 | 6/2001 |
| WO | 01/92342 | 12/2001 |
| WO | 02/06358 | 1/2002 |
| WO | 02/10227 | 2/2002 |
| WO | 02/18452 | 3/2002 |
| WO | 02/32968 | 4/2002 |
| WO | 02/38629 | 5/2002 |
| WO | 02/45854 | 6/2002 |
| WO | 02/46243 | 6/2002 |
| WO | 02/46250 | 6/2002 |
| WO | 02/49995 | 6/2002 |
| WO | 02/051884 | 7/2002 |

OTHER PUBLICATIONS

Hicks, F.; Brookhart, M.; "A Highly Active Anilinotropone-Based Neutral Nickel (II) Catalyst for Ethylene Polymerization", *Organometallics* 2001, 20, 3217-3219.

Connor, E.F.; Younkin, T.R.; Henderson, J.I.; Hwang, S.; Grubbs, R.H.; Roberts, W.P.; Litzau, J.J., "Linear Functionalized Polyethylene Prepared with Highly Active Neutral Ni (II) Complexes", *J. Pol. Sci. A.* 2002, 40, 2842-2854.

Schroeder, D.L.; Keim, w.; Zuideveld, M.A.; Mecking, S, "Ethylene Polymerization by Novel, Easily Accesible Catalysts Based on Nickel (II) Diazene Complexes", *Macromolecules*, 2002, 35, 6071-6073.

Laali, K.; Szele, I.; Zollinger, H., "Dediazoniation of Arendediazonium Ion. Part XXII. Reactions of 2,6-Dialkyl-Substituted Benzenediazonium Ions in Super Acids, Acetonitrile and Acetone" *Helvetica Chimica Acta* 1983, 66, 1737-1747.

Drent et al., "Palladium Catalysed Copolymerisation of Ethene with Alkylacrylates: Polar Comonomer Built into the Linear Polymer Chain", Chem. Commun. 2002, 744-745.

Stibrany et al., "Cu Catalysts for Homo- and Copolymerization of Olefins and Acrylates", Polymeric Materials: Science & Engineering 2002, 86, 325.

Stibrany et al., "Cu Catalysts for Homo- and Copolymerization of Olefins and Acrylates", Beyond Metallocenes: Next-Generation Polymerization Catalysts, ACS Symposium Series 857, Washington, DC. 2003, 222-230.

Wang et al., "Novel Nickel Catalysts for Ethylene/Polar Monomer Copolymerization", Polymeric Materials: Science & Engineering 2002, 86, 322.

Petrillo, G.; Novi, M.; Garbarino, G.; Filiberti, M., The Reaction Between Arendiazonium Tetrafloroborates and Alkaline Thiocarboxylates in DMSO: A Convenient Access to Aryl Thiolesters and other Aromatic Sulfur Derivatives: *Tetrahedron* 1989, 45, 7411-7420.

Johnson et al., "Copolymerization of Ethylene and Propylene with Functionalized Vinyl Monomers by Palladium(II) Catalysts", J. Am. Chem. Soc. 1996, 118, 267-268.

Mecking et al., "Mechanistic Studies of the Palladium-Catalyzed Copolymerization of Ethylene and α-Olefins with Methyl Acrylate", J. Am. Chem. Soc. 1998, 120, 888-899.

Johnson et al., "Copolymerization of Ethylene and Acrylates by Nickel Catalysts", Polymeric Materials: Science & Engineering 2002, 86, 319.

Liu et al., "Ethylene Polymerization and Ethylene/Methyl 10-Undecenoate Copolymerization Using Nickel(II) and Palladium(II) Complexes Derived from a Bulky P,O Chelating Ligand", Organometallics 2002, 21, 2836-2838.

Ittel et al., "Late-Metal Catalysts for Ethylene Homo- and Copolymerization", Chem. Rev. 2000, 100, 1169-1203.

Gibson et al., "Advances in Non-Metallocene Olefin Polymerization Catalysis", Chem. Rev. 2003, 103, 283-315.

Stibrany et al., "Polymerization and Copolymerization of Olefins and Acrylates by Bis(benzimidazole) Copper Catalysts", Macromolecules 2003, 36, 8584-8586.

U.S. Appl. No. 10/436,741, filed May 13, 2003, Hinkle et al., entitled :Olefin Polymerization Catalysts System.

Younkin et al., "Neutral, Single-Component Nickel (II) Polyolefin Catalysts that Tolerate Heteroatoms", Science, Jan. 21, 2000, vol. 287, pp. 460-462, XP-002296280.

* cited by examiner

OLEFIN POLYMERIZATION CATALYST SYSTEM USEFUL FOR POLAR MONOMERS

CROSS REFERENCE TO RELATED APPLICATION

The present application is a Continuation-in-Part of U.S. application Ser. No. 10/436,741, filed May 13, 2003.

FIELD OF THE INVENTION

This invention relates to novel processes to polymerize or oligomerize olefin monomers with polar monomers using novel phenoxide-containing transition metal compounds and polymers produced therefrom.

BACKGROUND OF THE INVENTION

The present invention is directed toward new transition metal compounds containing bidentate E-phenoxide ligands and formal neutral ligands that are useful for the oligomerization and polymerization of olefins. Bidentate E-phenoxide ligands form 6-membered metallacycle rings when bound to a transition metal. These compounds, and optionally an activator, can be used to oligomerize or polymerize unsaturated monomers such as olefins.

Other polymerization catalysts employing bidentate ligands based on phenoxides that form six-membered metallacycle rings have been reported in the art. Mitsui has reported low activity transition metal complexes containing azo-phenoxide ligands (European Patent EP-A1 0 990 664). Low activity, low molecular weight catalysts that use an azo-phenoxide ligand based upon a naphthyl ring have also been reported in the literature (*Macromolecules*, 2002, 35, 6071). Catalysts based upon keto-amide structures have been reported by DuPont (WO 98/30609). These show poor activity and low molecular weight or poor molecular weight control. Imine-phenoxide catalysts based on nickel have been reported both by Grubbs (*Science* 2000, 287, 460; *Organometallics* 1998, 17, 3149; *J. Polym. Sci. A*. 2002, 40, 2842; WO 98/42665; WO 2000/56786; WO 2000/56787; WO 2000/56781) and DuPont researchers (WO 98/30609). These imine-phenoxide systems were examined alongside the azo-phenoxide catalysts reported here and the imine-phenoxide systems were shown to give lower molecular weight polymer.

Other references of interest include: WO 98/42664; Hicks, F.; Brookhart, M. *Organometallics* 2001, 20, 3217; Laali, K.; Szele, I.; Zollinger, H., *Helvetica Chimica Acta* 1983, 66, 1737; and Petrillo, G.; Novi, M.; Garbarino, G.; Filiberti, M., *Tetrahedron* 1989, 45, 7411.

Functionalized polyolefins are of interest for many industrial applications due to the polymer property enhancements bestowed by polar groups. These advantages can include improved impact strength, adhesion, dyeability, printability, solvent resistance, melt strength, miscibility with other polymers, and gas barrier properties, as compared to unfunctionalized polyolefins.

ExxonMobil currently sells ester—(Optema™, Enable™), acetate—(Escorene™), and acid/ionomer— functionalized polyethylenes (Escor™, Iotek™) made by free-radical processes for adhesive, film, and specialty applications, among others.

However, free-radical polymerization methods do not allow for the precise control of important polymer properties such as branching, tacticity, molecular weight and molecular weight distribution. For this reason, it is desirable to develop transition metal catalysts capable of carrying out the direct copolymerization of olefins with polar comonomers. Market opportunities and advantages for substantially linear functional polyolefins and other controlled structures are expected in areas such as recreational materials (golf ball covers), durable goods, packaging, adhesives, and alloys.

To date, few systems for the direct copolymerization of olefins and polar comonomers exist. Cationic Pd diimine initiators, developed by Brookhart/DuPont, are capable of producing polyethylenes with up to ~20 mol % incorporation of acrylate comonomer. However, these materials are very heavily branched, and the acrylate comonomer is overwhelmingly placed at the ends of branches rather than in the main chain (WO 96/23010; *J. Am. Chem. Soc.* 1996, 118, 267; *J. Am. Chem. Soc.* 1998, 120, 888). Modified versions of these Pd diimines, and related P—O ligated Pd complexes (developed by Drent), can give more linear copolymers but at the expense of greatly reducing comonomer incorporation (<2 mol %) (WO 2001/92342; *Polym. Mat. Sci. Eng.* 2002, 86, 319; *Polym. Mat. Sci. Eng.* 2002, 86, 322; *Chem. Commun.* 2002, 744; *Organometallics* 2002, 21, 2836). To date, the most versatile copolymerization catalysts reported are Grubbs' single-component imine-phenoxide "neutral nickel" initiators. These salicylaldimine-ligated complexes can produce relatively linear copolymers of ethylene with functionalized long-chain and norbornene comonomers, having polar incorporations of up to ~30 mol %.

Recently, ExxonMobil developed a proprietary single-component neutral nickel olefin polymerization catalyst having o-aryl-disubstituted azo-phenoxide ligands (U.S. Ser. No. 10/436,741, filed May 13, 2003). This initiator can produce higher molecular weight polyethylenes and ethylene-octene copolymers than the related imine-phenoxide nickel initiators of Grubbs (which are reported to catalyze copolymerization of olefins with certain polar comonomers). Herein we report a process for the direct copolymerization of ethylene (or other olefins) with functionalized comonomers using our novel catalyst compounds. This catalyst shows certain advantages over the imine-phenoxide nickel initiators, including greater retention of catalyst activity and molecular weight in the presence of functional groups, and greater copolymer linearity or polar comonomer incorporation under certain conditions.

Additional references of interest involving ethylene/polar comonomer copolymerizations include: U.S. Pat. No. 6,410,664; U.S. Pat. No. 6,143,857; U.S. Pat. No. 6,562,922; Ittel, S. D. et al., *Chem. Rev.* 2000, 100, 1169; Gibson, V. C. et al., *Chem. Rev.* 2003, 103, 283; DD 99556 (East German patent); U.S. Pat. No. 6,506,704, WO 00/56785; U.S. Pat. No. 6,197,715; U.S. Pat. No. 6,197,714; Stibrany, R. T. et al., *Macromolecules* 2003, 36, 8584; WO 99/30822; U.S. Pat. No. 6,037,297; U.S. Pat. No. 6,417,303; U.S. Pat. No. 6,180,788; Stibrany, R. T. et al., *Polymeric Materials: Science & Engineering* 2002, 86, 325; and Stibrany, R. T. et al., in *Beyond Metallocenes: Next-Generation Polymerization Catalysts*; Patil, A. O.; Hlatky, G. G., Eds.; ACS Symposium Series 857; American Chemical Society: Washington, D.C., 2003, 222.

SUMMARY OF THE INVENTION

This invention relates to a polymerization method comprising contacting one or more polar monomers and one or more olefin monomers with a catalyst system comprising: 1) optionally, an activator, and 2) a catalyst composition represented by the formula:

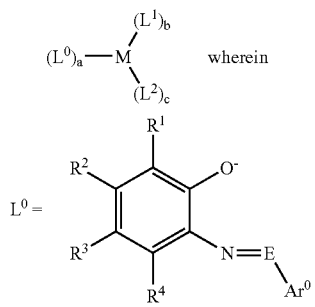

wherein

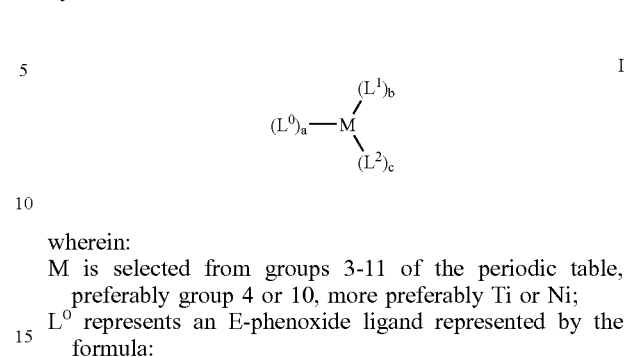

M is selected from groups 3-11 of the periodic table;
E is nitrogen or phosphorus;
$Ar^0$ is arene;
$R^1$-$R^4$ are, each independently, selected from hydrogen, hydrocarbyl, substituted hydrocarbyl or functional group, provided however that $R^3$ and $R^4$ do not form a naphthyl ring;
$L^1$ represents a formal anionic ligand,
$L^2$ represents a formal neutral ligand,
a is an integer greater than or equal to 1;
b is an integer greater than or equal to 0; and
c is an integer greater than or equal to 1.

DETAILED DESCRIPTION OF THE INVENTION

For the purposes of this invention and the claims thereto when a polymer is referred to as comprising a monomer, the momomer present in the polymer is the polymerized form of the monomer. For the purposes of this invention and the claims thereto when a polymer is referred to as comprising an olefin, the olefin present in the polymer is the polymerized form of the olefin. For the purposes of this invention and the claims thereto when a polymer is referred to as comprising a polar monomer, the polar monomer present in the polymer is the polymerized form of the polar monomer. In the description herein the transition metal catalyst compound may be described as a catalyst precursor, a pre-catalyst compound, a transition metal complex or a catalyst compound, and these terms are used interchangeably. A catalyst system is a combination of a transition metal catalyst compound and an activator. An activator is also interchangeably referred to as a cocatalyst. In addition, a reactor is any container(s) in which a chemical reaction occurs.

As used herein, the numbering scheme for the Periodic Table Groups is the new notation as described in CHEMICAL AND ENGINEERING NEWS, 63(5), 27 (1985).

Further for purposes of this invention Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, and TMS is trimethylsilyl.

The catalyst compound preferably contains at least one E-phenoxide ligand ($L^0$), and at least one formal neutral ligand ($L^2$). The remaining ligands in the coordination sphere of the metal compound typically are such that the compound attains a d electron count of 14-18. The d electron count is the formal sum of the metal's d electrons plus those contributed by the ligands.

Preferred E-phenoxide metal compounds are represented by formula:

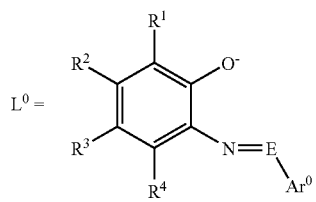

wherein:
M is selected from groups 3-11 of the periodic table, preferably group 4 or 10, more preferably Ti or Ni;
$L^0$ represents an E-phenoxide ligand represented by the formula:

$$L^0 = \begin{array}{c}\text{[phenoxide structure with } R^1, R^2, R^3, R^4, O^-, N=E, Ar^0\text{]}\end{array}$$

wherein:
E is nitrogen or phosphorus, preferably nitrogen;
$Ar^0$ is arene;
$R^1$-$R^4$ are each independently selected from hydrogen, hydrocarbyl, substituted hydrocarbyl or functional group, provided that $R^3$ and $R^4$ do not form a naphthyl ring;
$L^1$ represents a formal anionic ligand;
$L^2$ represents a formal neutral ligand;
a is an integer greater than or equal to 1, preferably a=1, 2, 3 or 4, preferably a=1 or 2;
b is an integer greater than or equal to 0, preferably b is 0, 1, 2, 3, 4, 5 or 6, more preferably b=0, 1 or 2; and
c is an integer greater than or equal to 1, preferably c=1, 2, 3 or 4, more preferably 1 or 2.

The metal compound may be neutral or a charged species with a counterion.

The metal compound preferably contains at least one formal neutral ligand coordinated to the metal in addition to the nitrogen or phosphorus of the E-phenoxide ligand(s). Formal neutral ligands are defined as ligands that are neutral, with respect to charge, when formally removed from the metal in their closed shell electronic state. Formal neutral ligands contain at least one lone pair of electrons, pi-bond or sigma bond that are capable of binding to the transition metal. Formal neutral ligands may also be polydentate when more than one formal neutral ligand is connected via a bond or a hydrocarbyl, substituted hydrocarbyl or a functional group tether. A formal neutral ligand may be a substituent of another metal compound, either the same or different, such that multiple compounds are bound together.

Formal neutral ligands may be composed of combinations of hydrocarbyl, substituted hydrocarbyl, and functional groups. Non-limiting examples of formal neutral ligands are ethers, ketones, esters, alcohols, carboxylic acids, amines, imines, azo, nitriles, heterocycles, phosphines, thioethers, alkyls, alkenes, alkynes, and arenes.

For purposes of this invention and the claims thereto "ZETA FORMAL NEUTRAL LIGANDS" are defined to be formal neutral ligands represented by the following formulae:

P(C(CH₃)₃)₃  P(C₆H₁₁)₃  P(CH(CH₃)₂)₃  P(CH₂CH₂CH₃)₃  P(CH₂CH₃)₃

P(CH₃)₃  P(C₆H₄OCH₃)₃  P(CH₂C₆H₅)₃  P(C₆H₄CH₃)  P(C₆H₅)₃

P(CH=CH₂)₃  P(C₆H₄F)₃  P(C₆H₄Cl)₃  P(C₂H₅)₂C₆H₅P(CH₃)₂C₆H₅

P(C₆H₅)₂CH₃  P(C₆H₅)₂NMe₂  P(C₆H₅)CH₂C₆H₅  P(C₆H₅)₂(C₆H₄OCH₃)

P(C₆H₅)(CH₂C₆H₅)₂  P(C₆H₅)₂(CH=CH₂)  P(C₆H₅)₂(C₆H₄F)

P(OCH₂CH₃)(C₆H₅)₂  P(OCH(CH₃)₂)₂C₆H₅  PH(C₆H₅)₂

P(OCH₂CH₂CH₃)₂C₆H₅  P(OC₆H₅)(C₆H₅)₂  P(C₆H₅)₂C₆F₅

PPh₂(C₆H₄Cl)  P(C₆H₃(OCH₃)₂)₃  P(C₆H₅)₂(C₆H₄N(CH₃)₂)

P(C₆H₂(CH₃)₃)₃  P(C₆H₅)₂(C₆H₂(CH₃)₃)  P(C₆H₅)(C₆F₅)₂  P(C₆F₅)₃

P(C₁₀H₇)₃  Me₃P=CH₂  (C₆H₅)₃P=CH₂  H₂C=CH₂

H₂C=CHCH₃  H₂C=CH₂CH₂CH₃  CH₃CH=CHCH₃

H₂C=CH₂CH₂CH₂CH₃  CH₃CH=CHCH₂CH₃

H₂C=CH₂CH₂CH₂CH₂CH₃  CH₃CH=CHCH₂CH₂CH₃

CH₃CH₂CH=CHCH₂CH₃  CH₃CH=CHCH₂CH₂CH₂CH₃

CH₃CH₂CH=CHCH₂CH₂CH₃

H₂C=CH₂CH₂CH₂CH₂CH₂CH₂CH₃

CH₃CH₂CH₂CH=CHCH₂CH₂CH₃  CH₃CH(CH₃)CH=CH₂

C(CH₃)₃CH=CH₂  (CH₃)₂C=CH₂  CH₃CH₂CH(CH₃)CH=CH₂

H₂C=CH·CH=CH₂  CH₃CH=CH·CH=CH₂

CH₃CH=CH·CH=CHCH₃  H₂C=C(CH₃)—(CH₃)C=CH₂

(CH₃CH₂)₂C=CH₂  H₂C=C(CH₃)—CH=CH₂

H₂C=CH—CH₂)₁—CH=CH₂  H₂C=CH—CH₂)₂—CH=CH₂

H₂C=CH—CH₂)₃—CH=CH₂  H₂C=CH—CH₂)₄—CH=CH₂

H₂C=CH—CH₂)₁—CH=C(CH₃)₂

H₂C=CH—CH₂)₂—CH=C(CH₃)₂

H₂C=CH—CH₂)₃—CH=C(CH₃)₂

H₂C=CH—CH₂)₄—CH=C(CH₃)₂

(C₆H₅)CH=CH—CH=CH₂

(C₆H₅)CH=CH—CH=CH(C₆H₅)

CH₂=CH—CH₂CH=CHCH₃

CH₂=CH—CH₂C(CH₃)=CHCH₃

CH₂=C(CH₃)—CH₂CH=CHCH₃

CH₂=C(CH₃)—CH₂CH₃

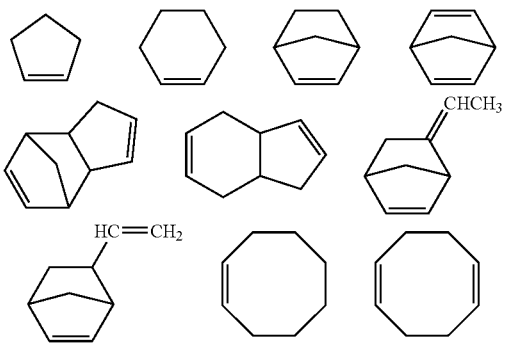

-continued

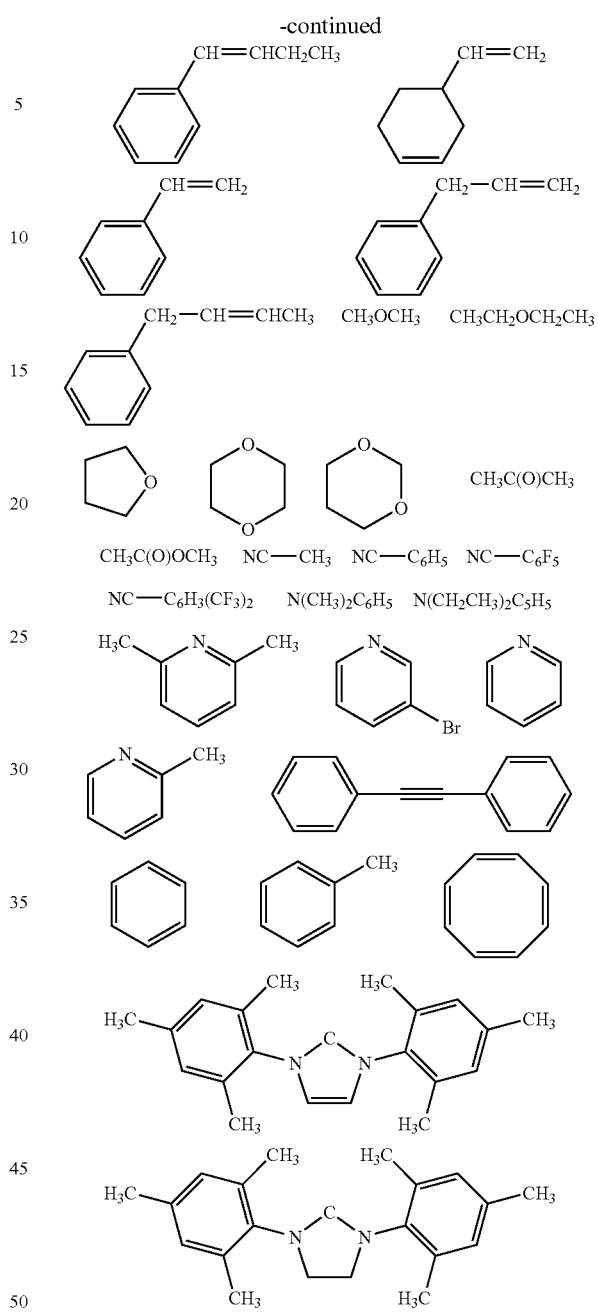

Formal anionic ligands are defined as ligands that are anionic, with respect to charge, when formally removed from the metal in their closed shell electronic state. Formal anionic ligands include hydride, halide, hydrocarbyl, substituted hydrocarbyl or functional group. Non-limiting examples of formal anionic ligands include hydride, fluoride, chloride, bromide, iodide, alkyl, aryl, alkenyl, alkynyl, allyl, benzyl, acyl, trimethylsilyl. Formal anionic ligands may also be polydentate when more than one formal anionic ligand is connected via a bond or a hydrocarbyl, substituted hydrocarbyl or a functional group tether. A formal anionic ligand may be a substituent of another metal compound, either the same or different, such that multiple compounds are bound together.

For purposes of this invention and the claims thereto "ZETA-FORMAL ANIONIC LIGANDS" is defined to be the group of formal anionic ligands represented by the following formulae:

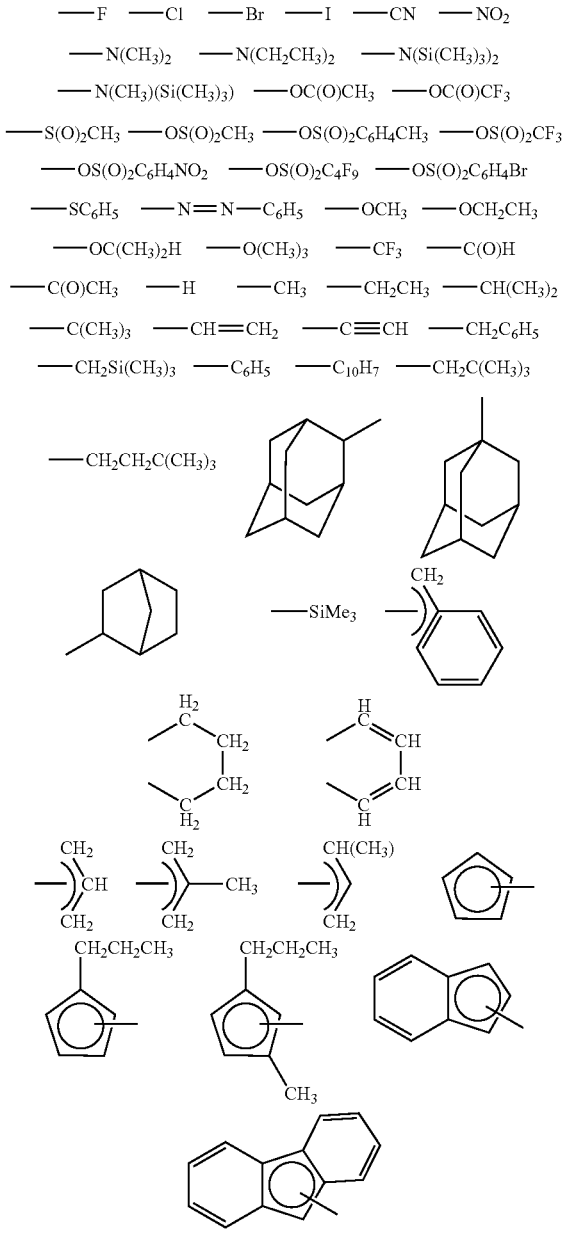

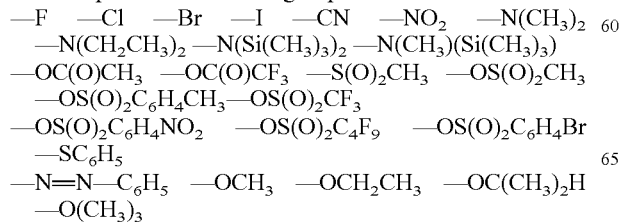

More preferred formal anionic ligands include: —F, —Cl, —Br, —I, —N(CH$_3$)$_2$, —OCH$_3$, —H, —CH$_3$, —C$_6$H$_5$, -allyl, -benzyl, —CH$_2$Si(CH$_3$)$_3$.

Preferred non-limiting examples of formal anionic ligand that comprises a functional group include:
—F   —Cl   —Br   —I   —CN   —NO$_2$   —N(CH$_3$)$_2$
—N(CH$_2$CH$_3$)$_2$   —N(Si(CH$_3$)$_3$)$_2$   —N(CH$_3$)(Si(CH$_3$)$_3$)
—OC(O)CH$_3$   —OC(O)CF$_3$   —S(O)$_2$CH$_3$   —OS(O)$_2$CH$_3$
—OS(O)$_2$C$_6$H$_4$CH$_3$   —OS(O)$_2$CF$_3$
—OS(O)$_2$C$_6$H$_4$NO$_2$   —OS(O)$_2$C$_4$F$_9$   —OS(O)$_2$C$_6$H$_4$Br
—SC$_6$H$_5$
—N=N—C$_6$H$_5$   —OCH$_3$   —OCH$_2$CH$_3$   —OC(CH$_3$)$_2$H
—O(CH$_3$)$_3$ More preferred formal anionic ligands that comprise functional groups include: —F, —Cl, —Br, —I, —N(CH$_3$)$_2$, —OCH$_3$.

Using this nomenclature of anionic and neutral ligands, the ligands may be categorized as combinations of anionic and neutral ligands as when L$^1$ and L$^2$ are connected via a bond or a hydrocarbyl, substituted hydrocarbyl or a functional group tether. Preferred non-limiting examples of L$^1$, L$^2$ that meet this definition include ethyl, norbornyl, allyl, benzyl, CH$_2$CH$_2$C(O)Me, 1-(2-N(CH$_3$)$_2$C$_6$H$_4$), acetylacetonate. The capability of hydrocarbyl groups, such as ethyl and norbornyl, to coordinate as a formal anionic ligand (M-C sigma bond) and a formal neutral ligand, via an agostic 3 center-2 electron interaction between C, H and M is well recognized.

Monodentate ligands that are capable of multiple bonding to the metal may be categorized as combinations of anionic and neutral ligands. Ligands which display this behavior are functional groups that in addition to being a formal anionic ligand, have at least one pair of electrons, either localized or in a bonding arrangement with another atom or atoms, that also interact with the metal.

Non-limiting examples of such ligands are oxo, imido, carbene and carbyne. Preferred non-limiting examples include:
=O   =CPh$_2$   =CH$_2$   =CHPh   =CH(C$_6$H$_2$(CH$_3$)$_3$)
≡C—C$_6$H$_2$(CH$_3$)$_3$   ≡C—C$_6$H$_3$(CH(CH$_3$)$_2$   ≡N—C$_6$H$_2$(CH$_3$)$_3$
≡N—C$_6$H$_3$(CH(CH$_3$)$_2$ Preferred non-limiting examples of hydrocarbyl groups include:

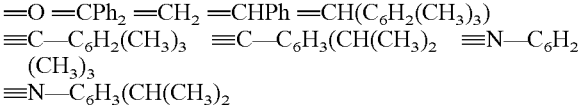
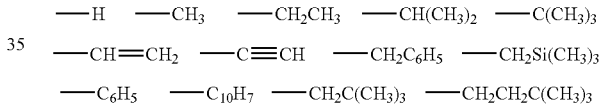
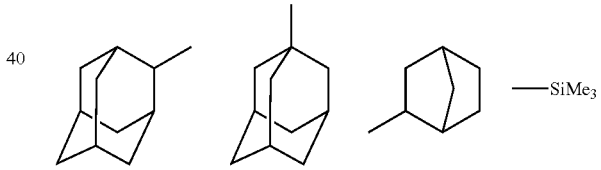

Substituted hydrocarbyl radicals (also called substituted hydrocarbyls) are radicals in which at least one hydrocarbyl hydrogen atom has been substituted with at least one heteroatom or heteroatom containing group.

Preferred non-limiting examples of substituted hydrocarbyls include:

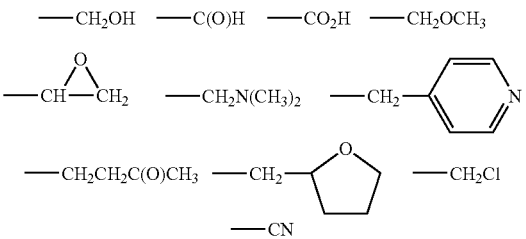

The term "hydrocarbyl radical" is sometimes used interchangeably with "hydrocarbyl" throughout this document. For purposes of this disclosure, "hydrocarbyl radical"

encompasses radicals containing carbon hydrogen and optionally silicon atoms, preferably 1 to 100 carbon atoms, hydrogen and optionally silicon. These radicals can be linear, branched, or cyclic including polycyclic. These radicals can be saturated, partially unsaturated or fully unsaturated, and when cyclic, may be aromatic or non-aromatic.

In some embodiments, the hydrocarbyl radical is selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. For this disclosure, when a radical is listed it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

An arene is a substituted or unsubstituted aromatic hydrocarbon. Arenes may be monocyclic, polycyclic, hydrocarbon ring assemblies or fused ring systems. Arenes may be substituted or unsubstituted heterocyclics, polyheterocyclics, heterocyclic ring assemblies or fused heterocyclic ring systems. (In the formulae below, $Z^+$ is a cation, preferably a metal or metal compound of groups 1, 2, 11, or 12 and $A^-$ is an anion.) For purposes of this invention and the claims thereto the term "ZETA-ARENES" is defined to be the group of arenes represented by the following formulae:

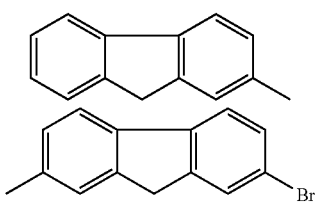

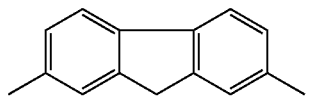

-continued

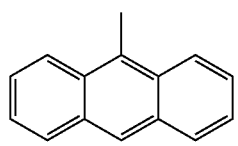
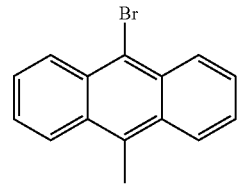

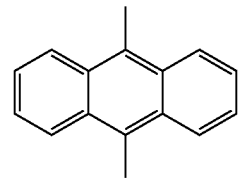

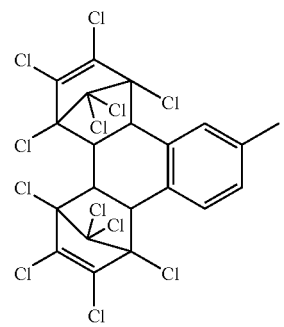

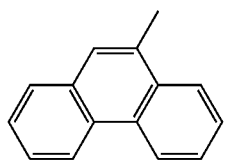
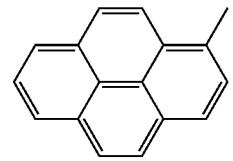

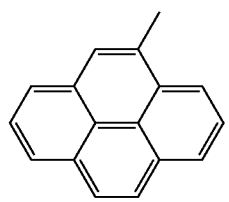
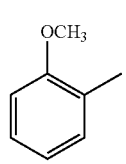
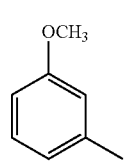

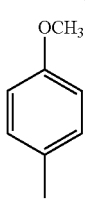
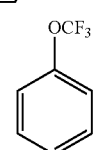
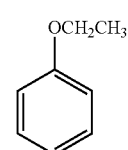
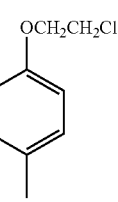

-continued
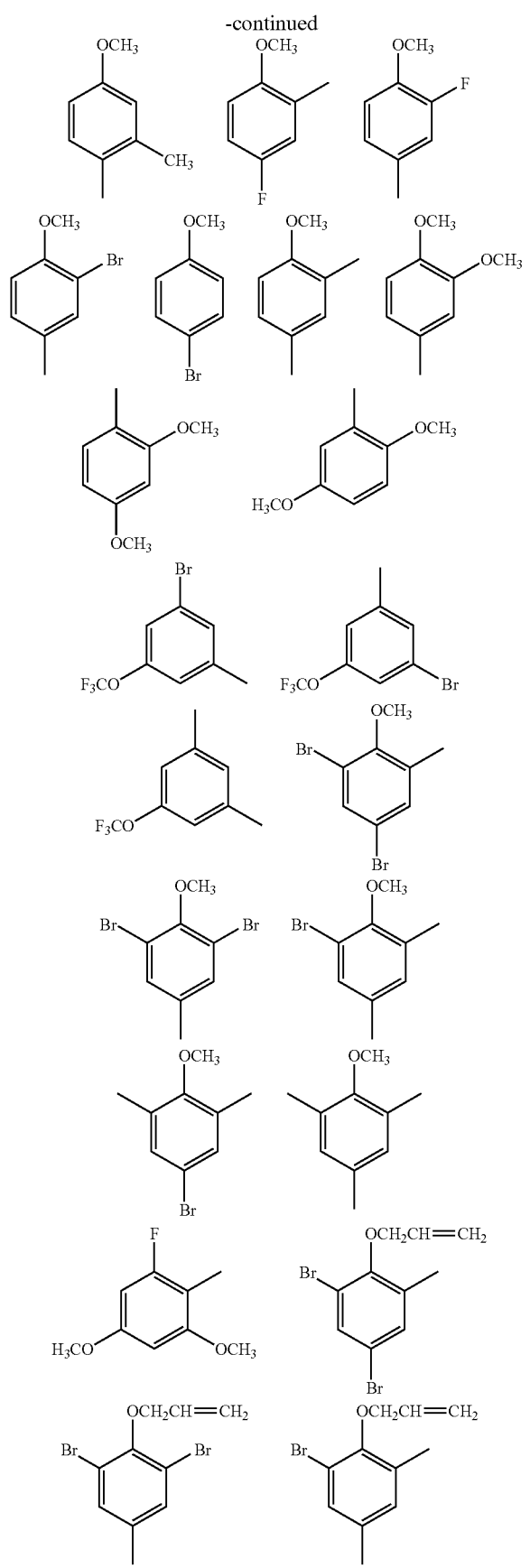
-continued
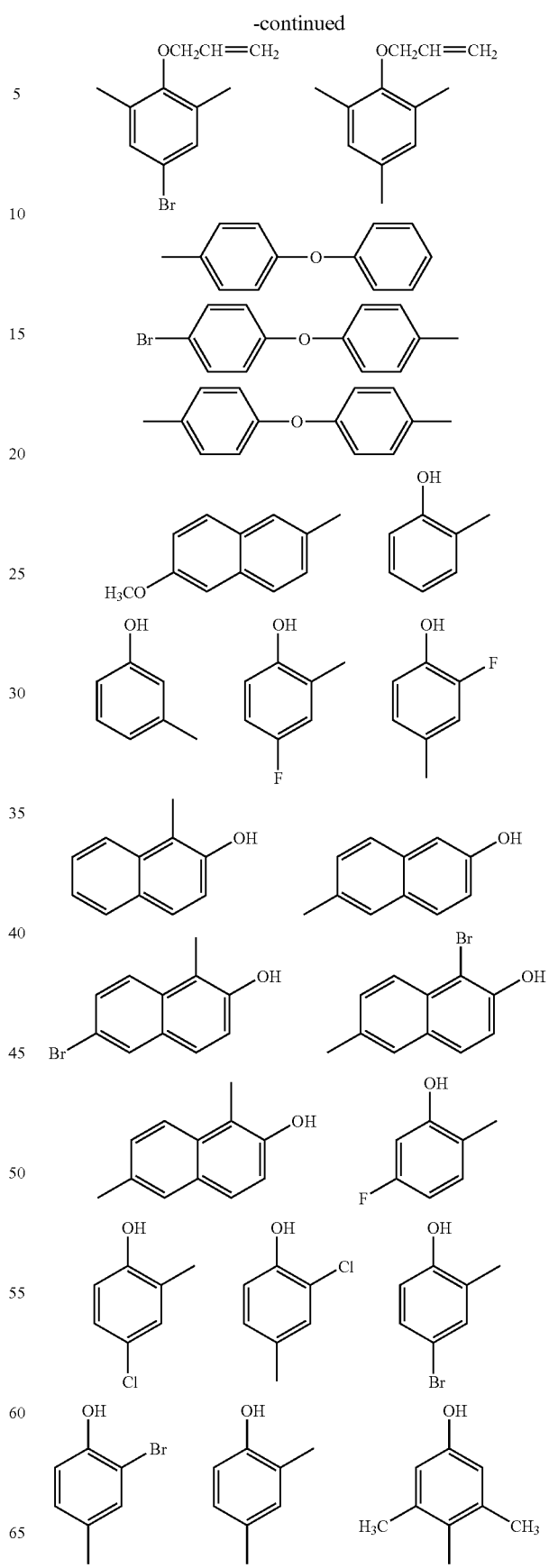

-continued
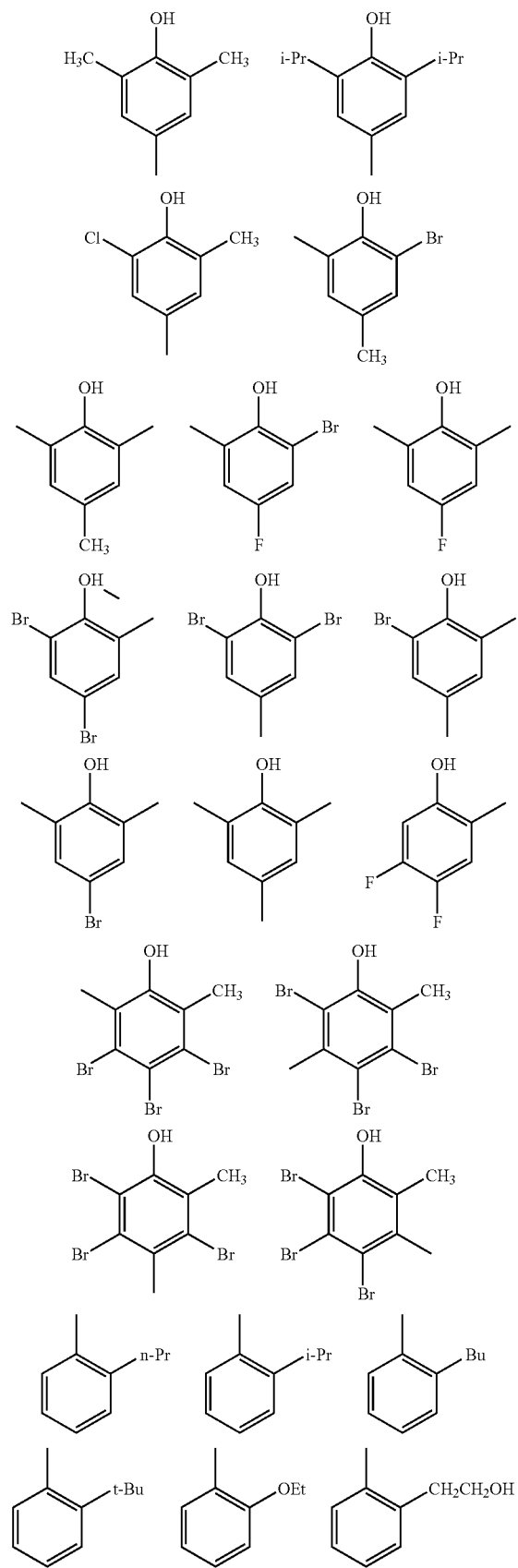
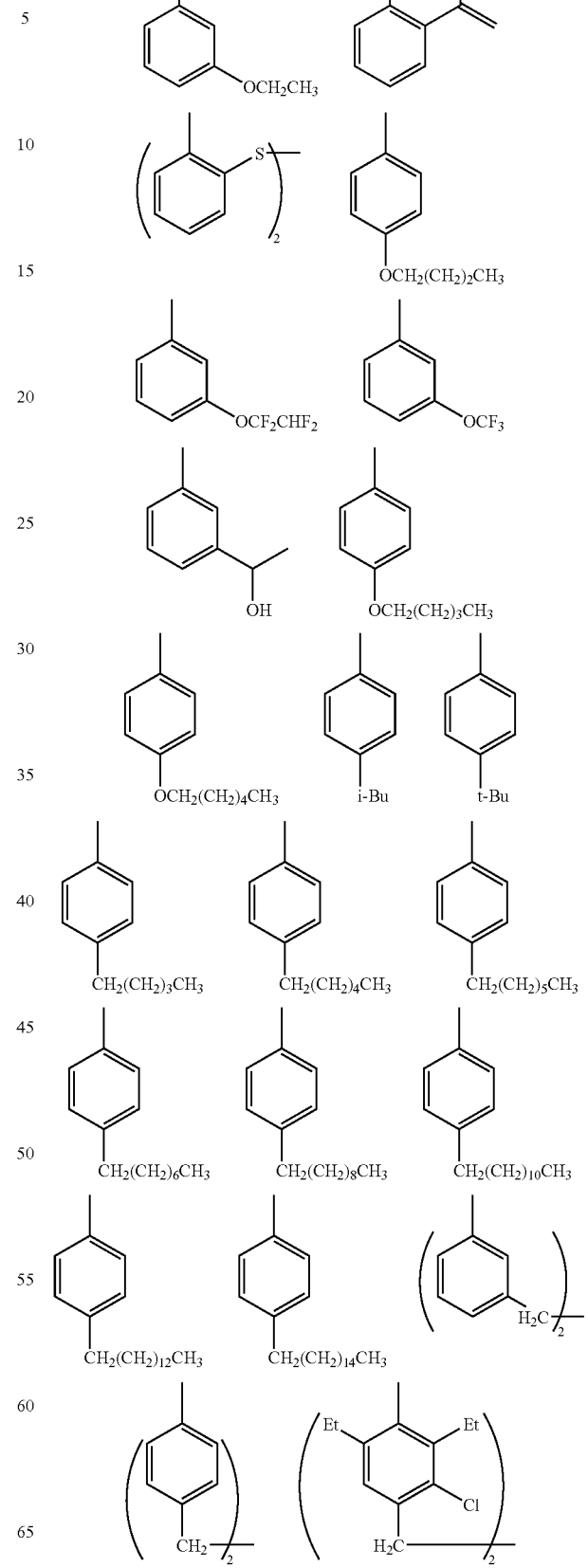

-continued
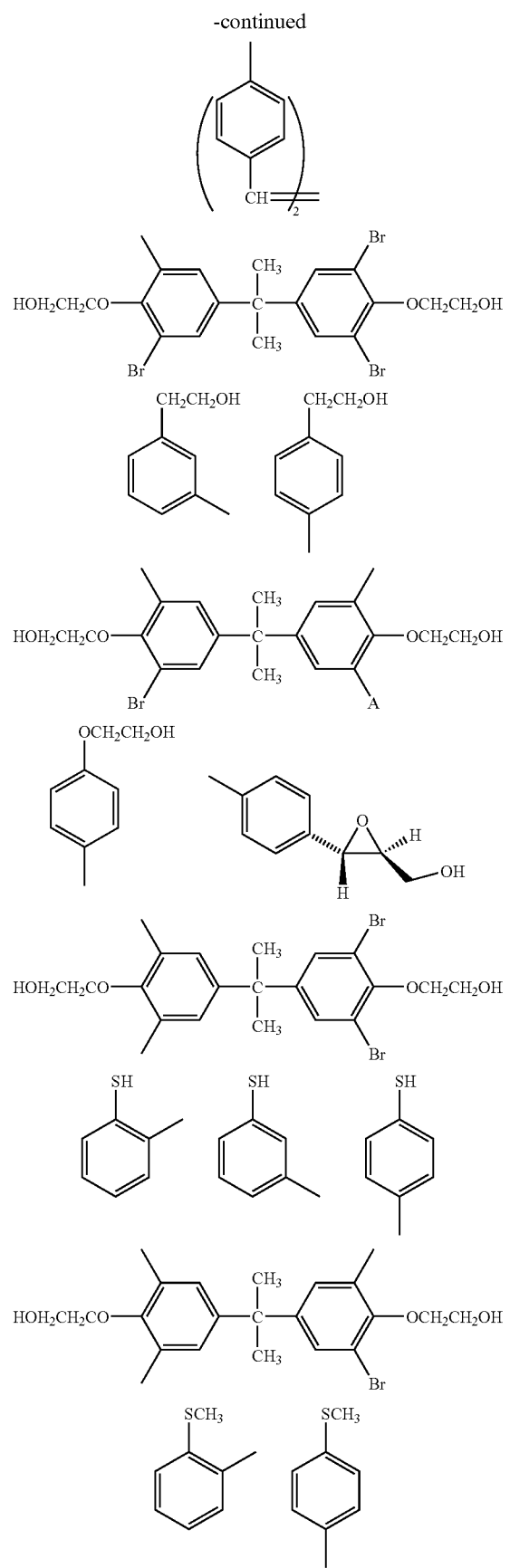
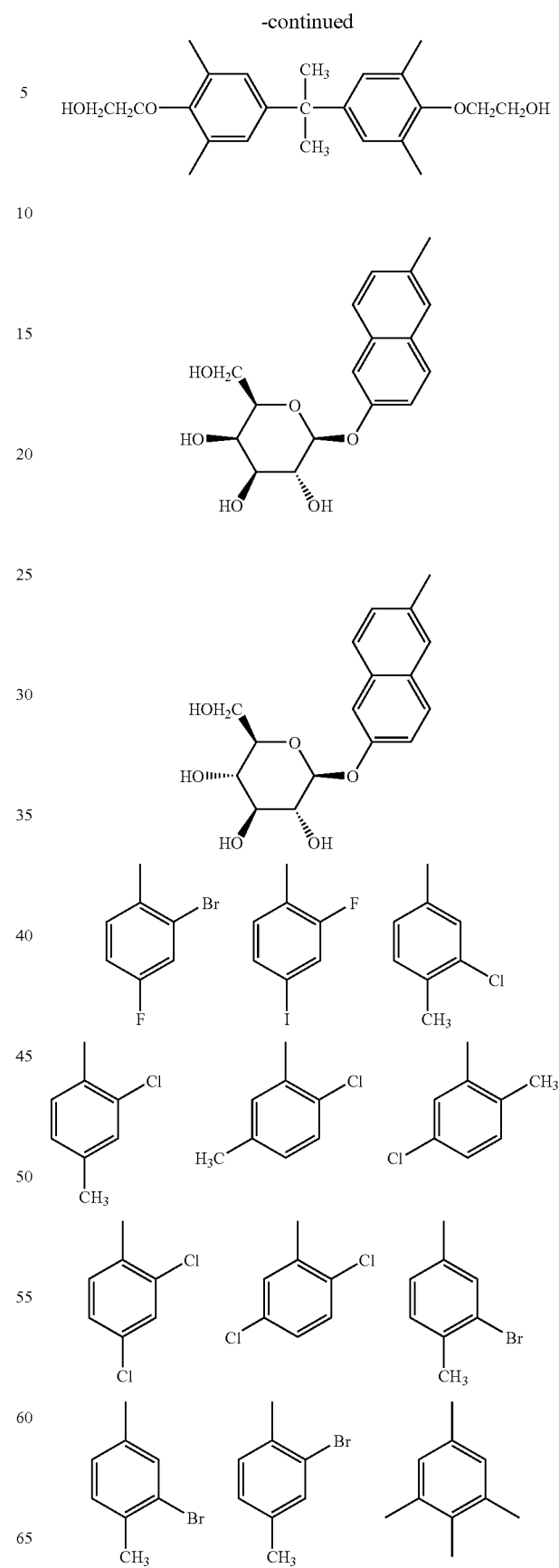

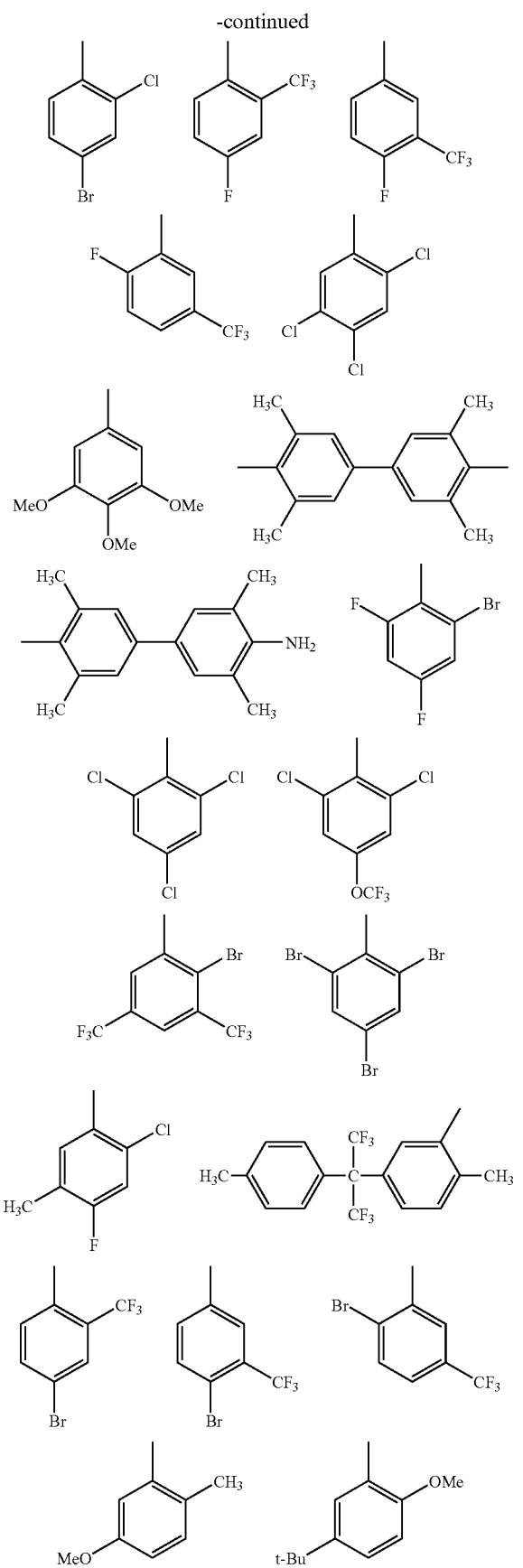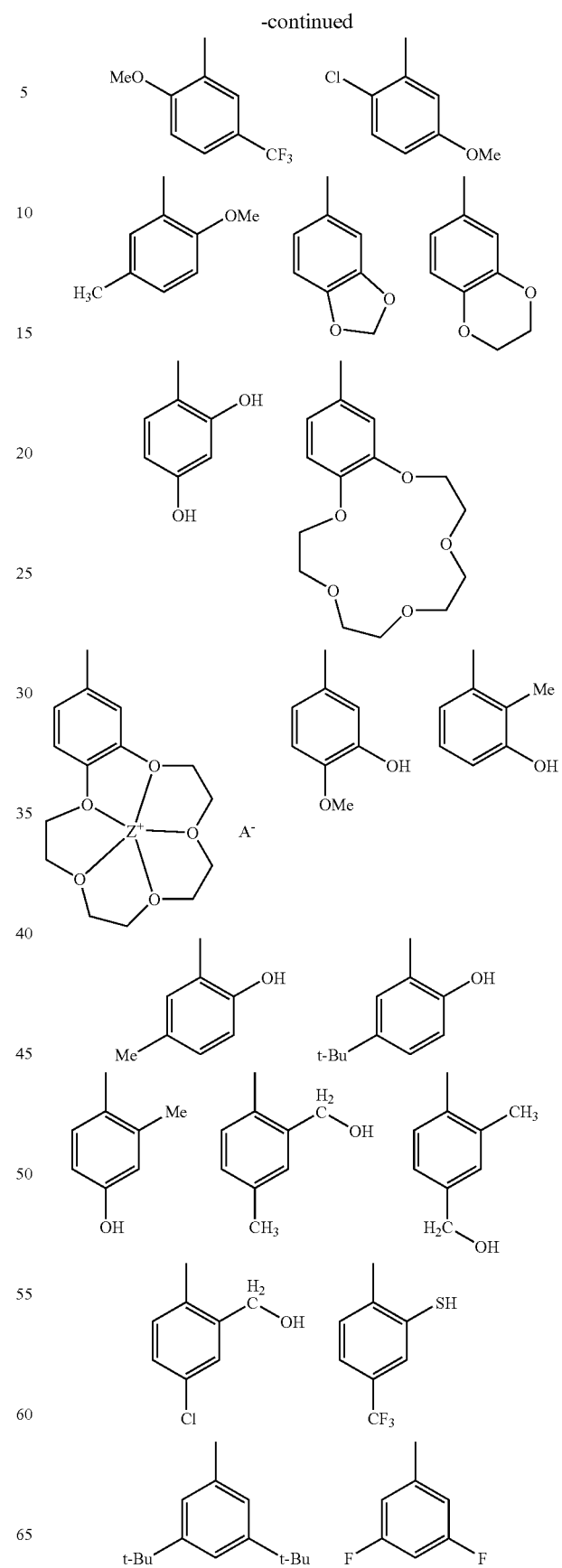

-continued
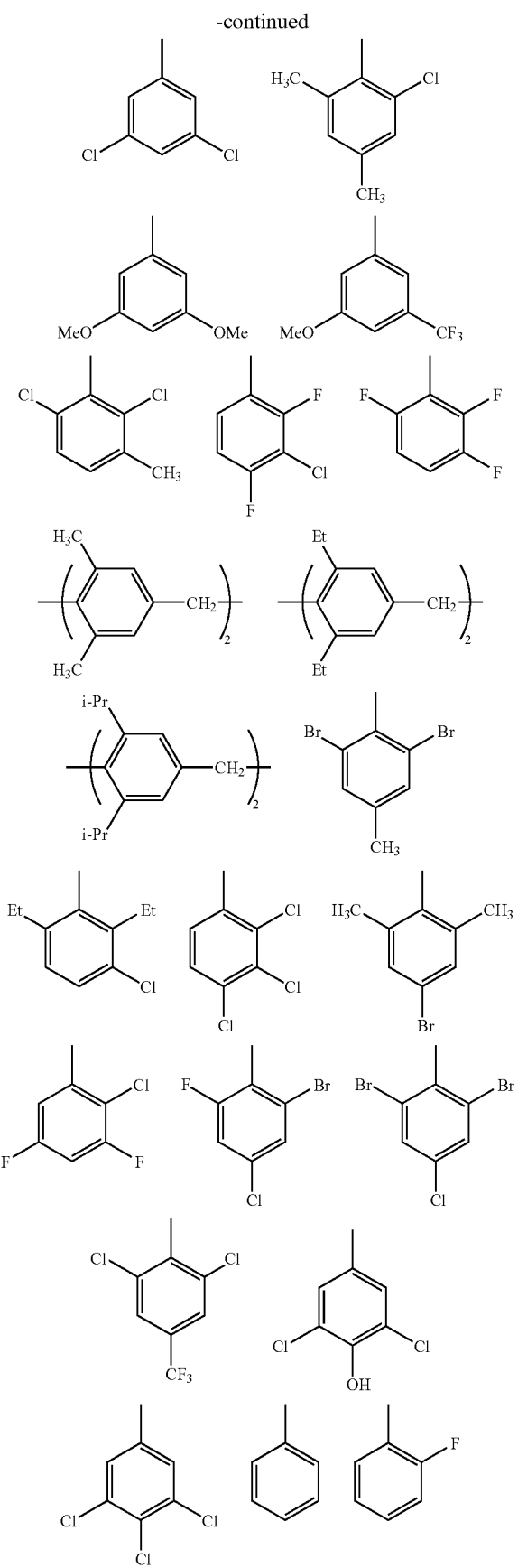
-continued
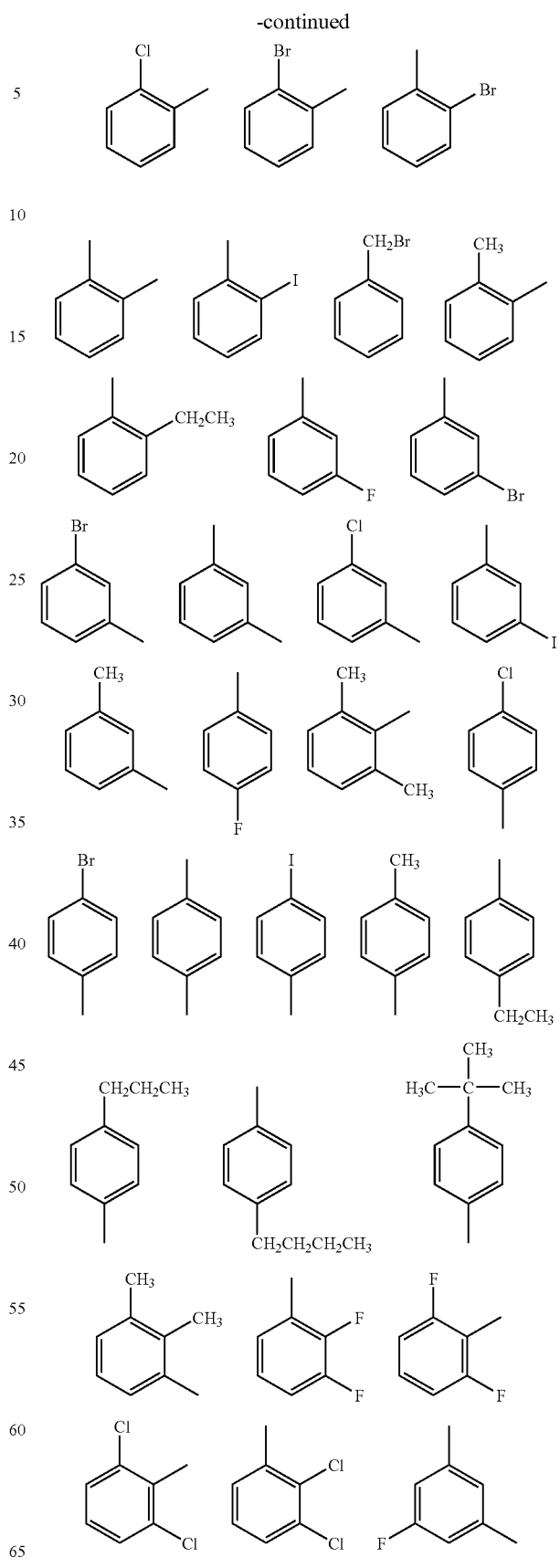

-continued
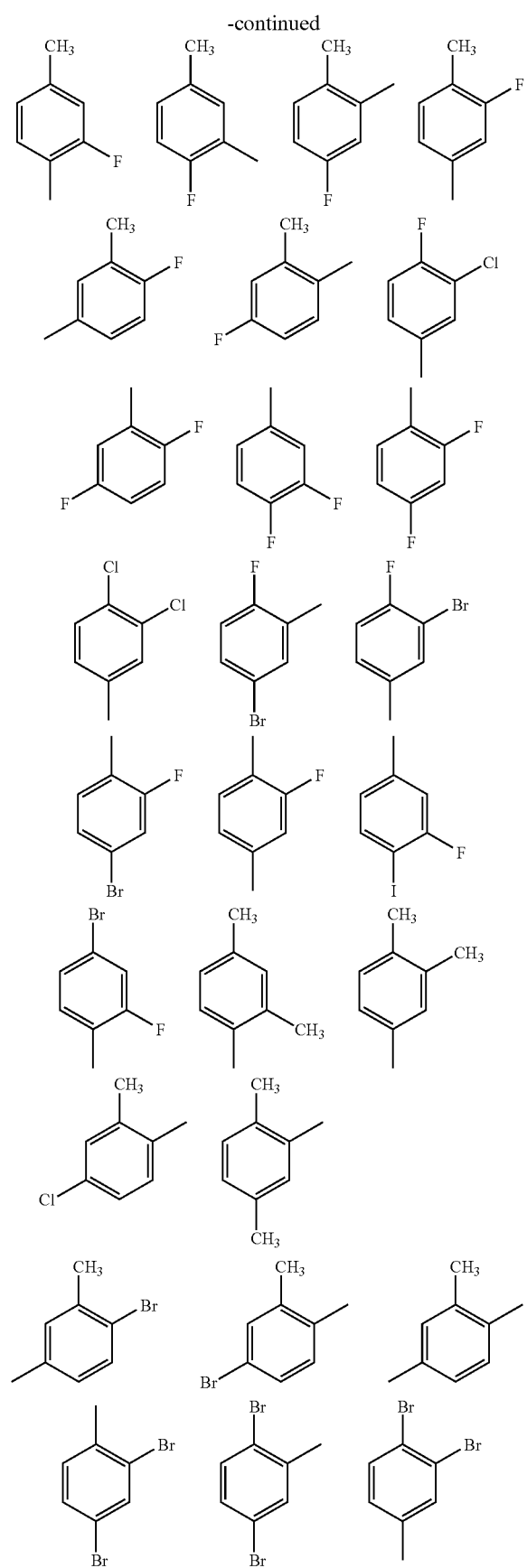
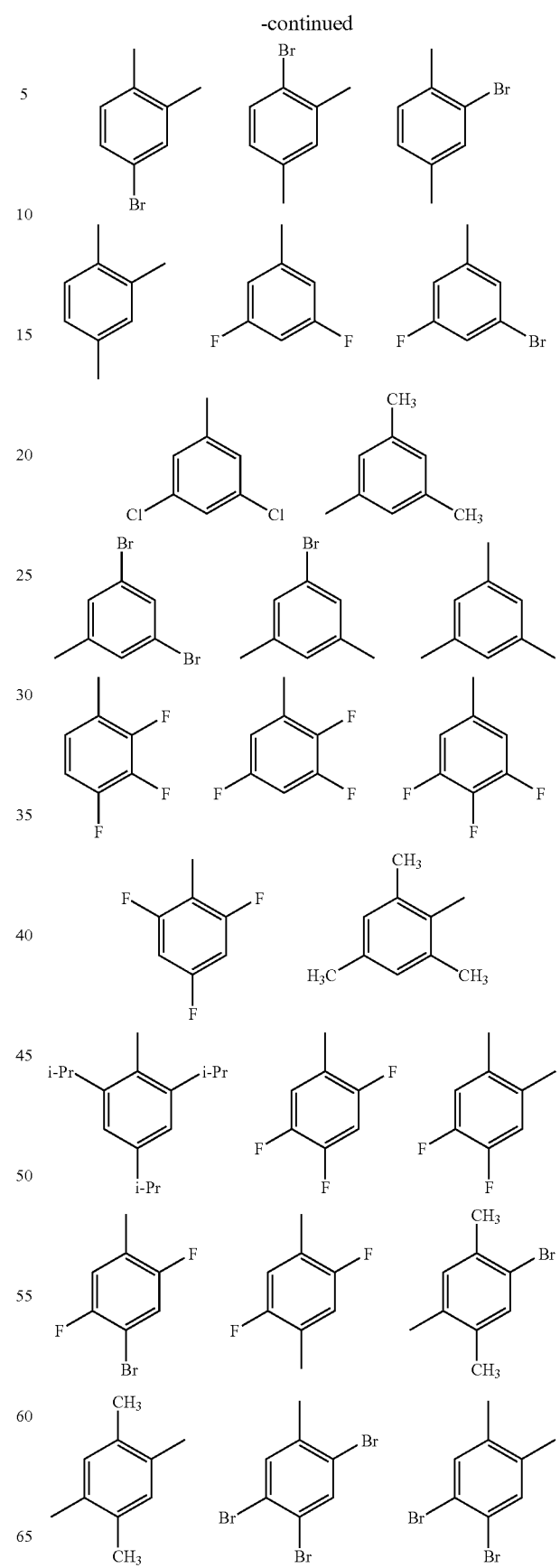

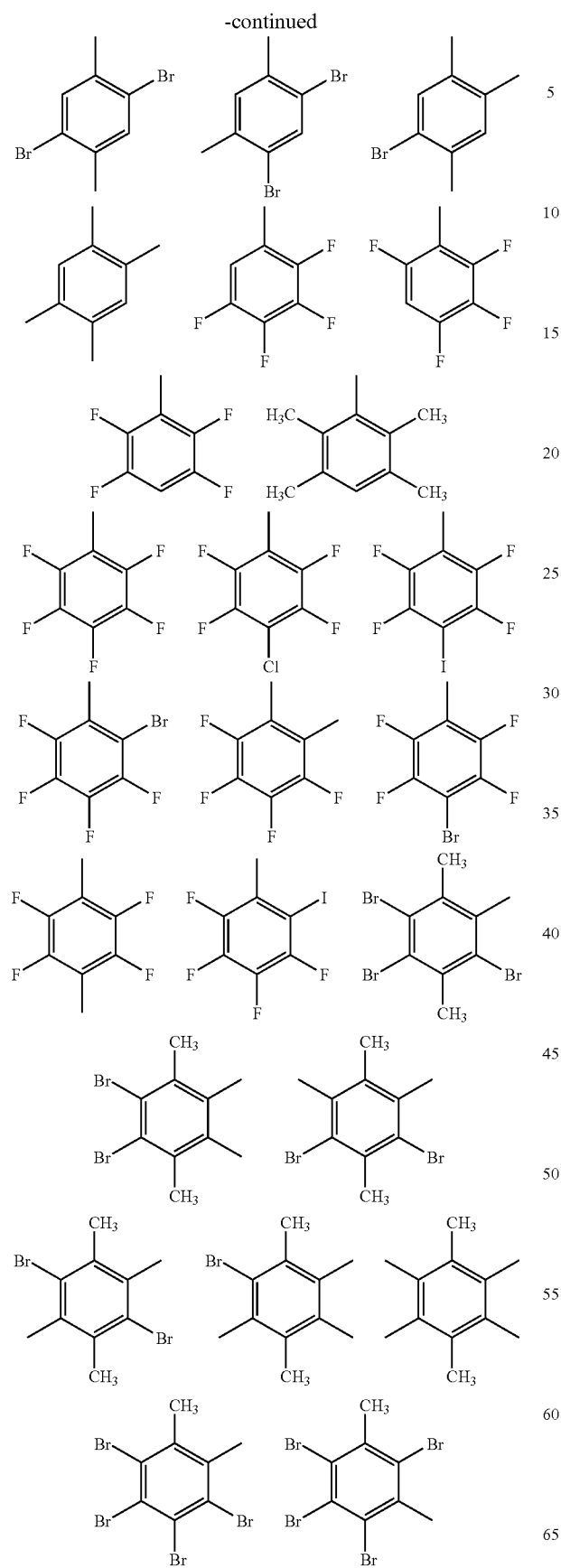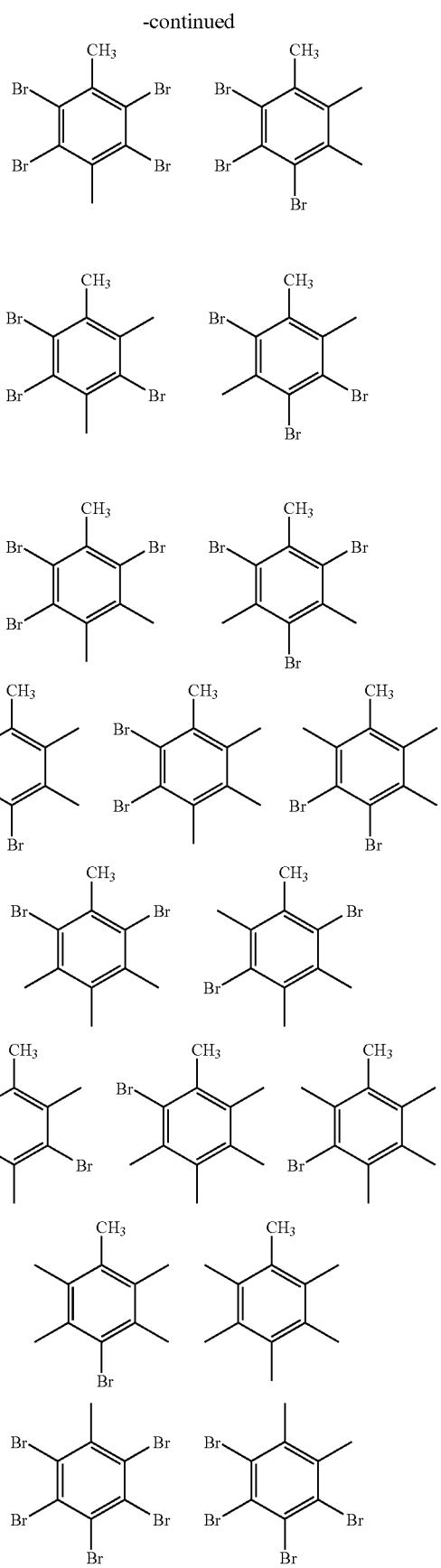

-continued
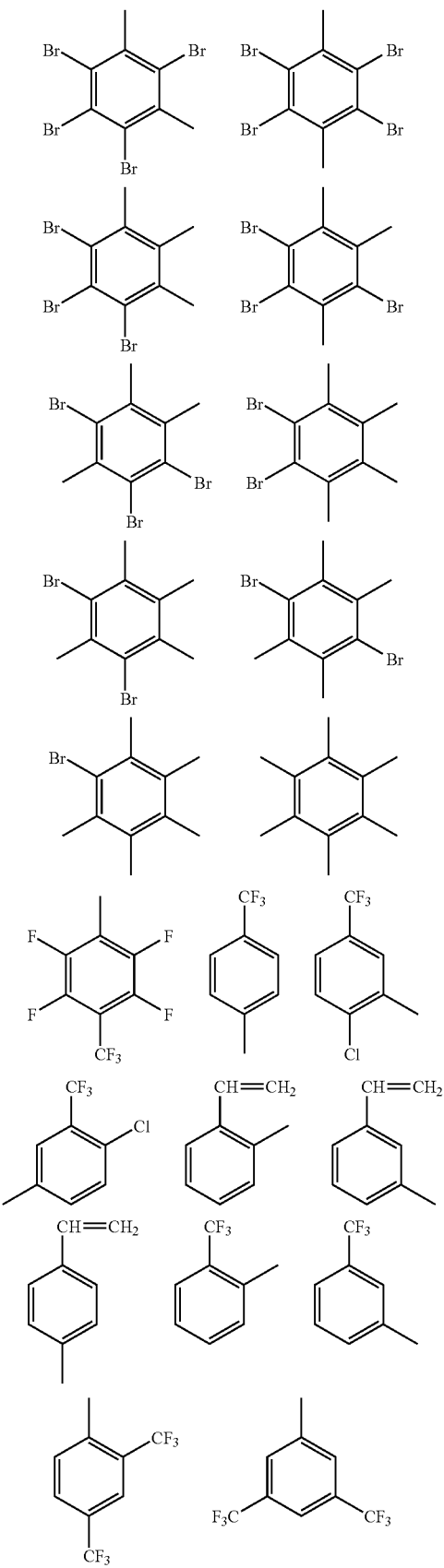
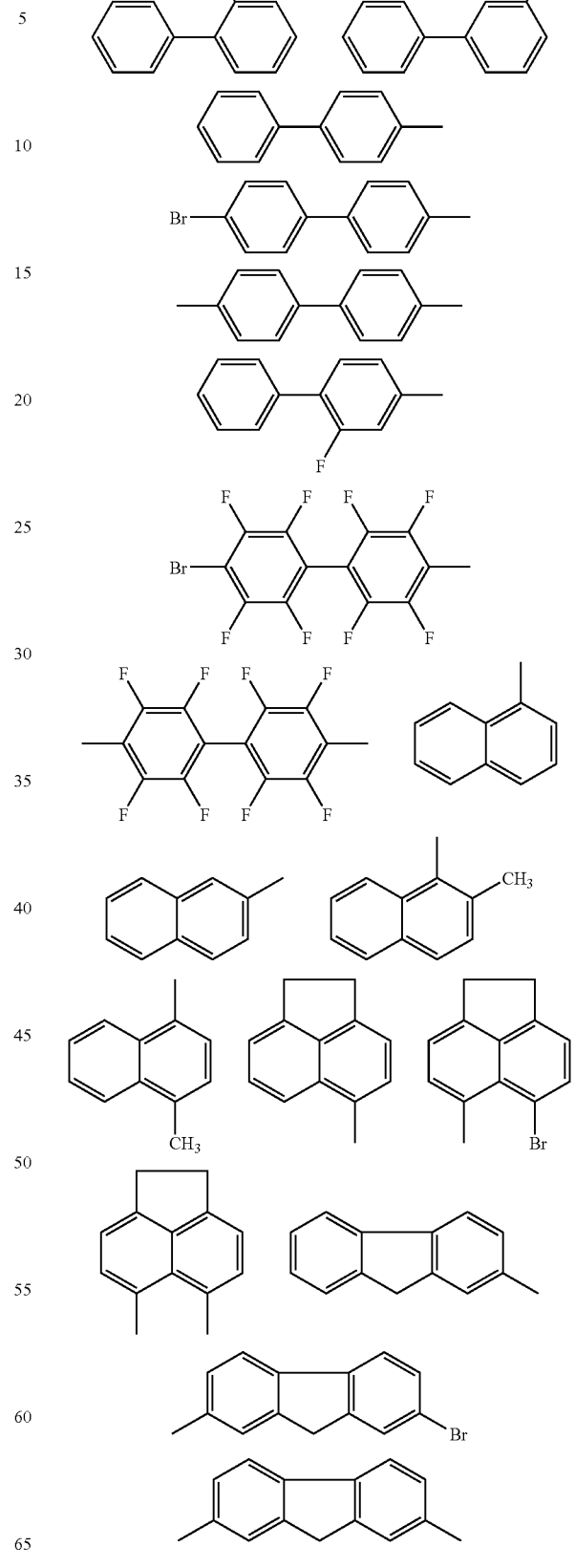

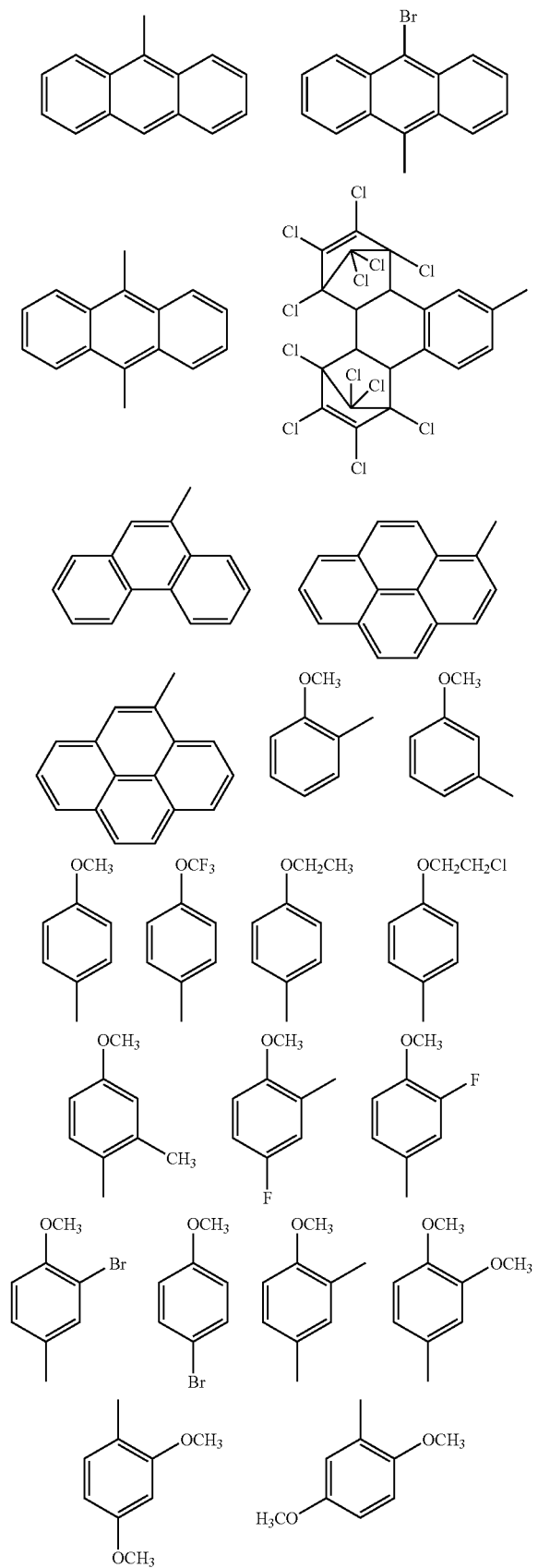
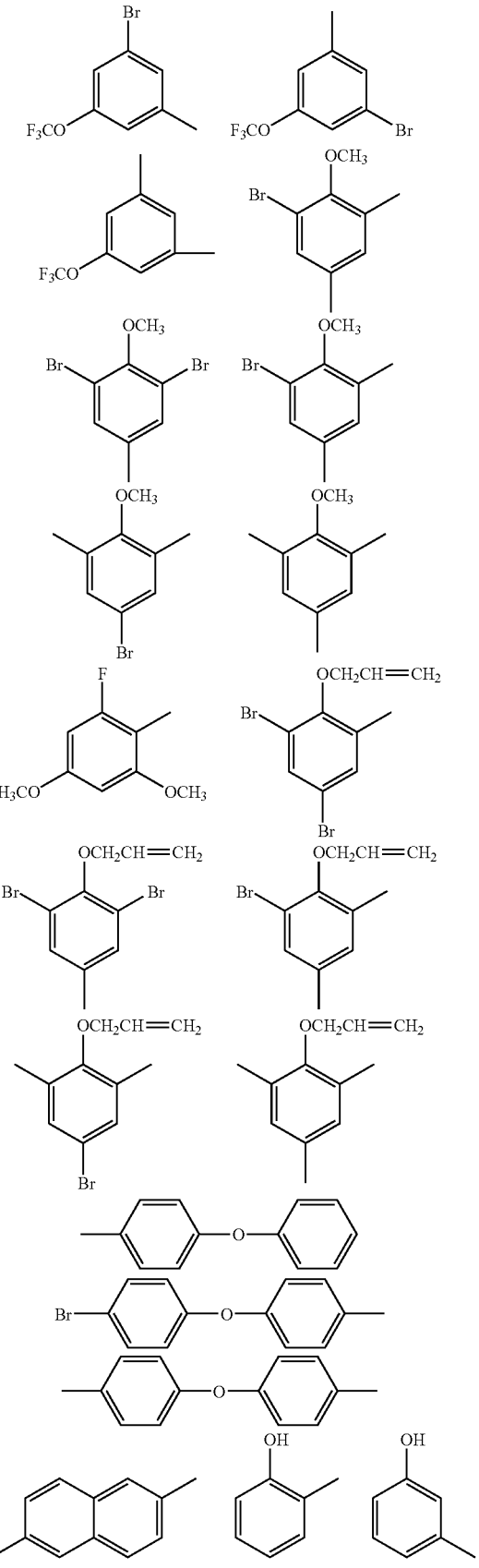

-continued
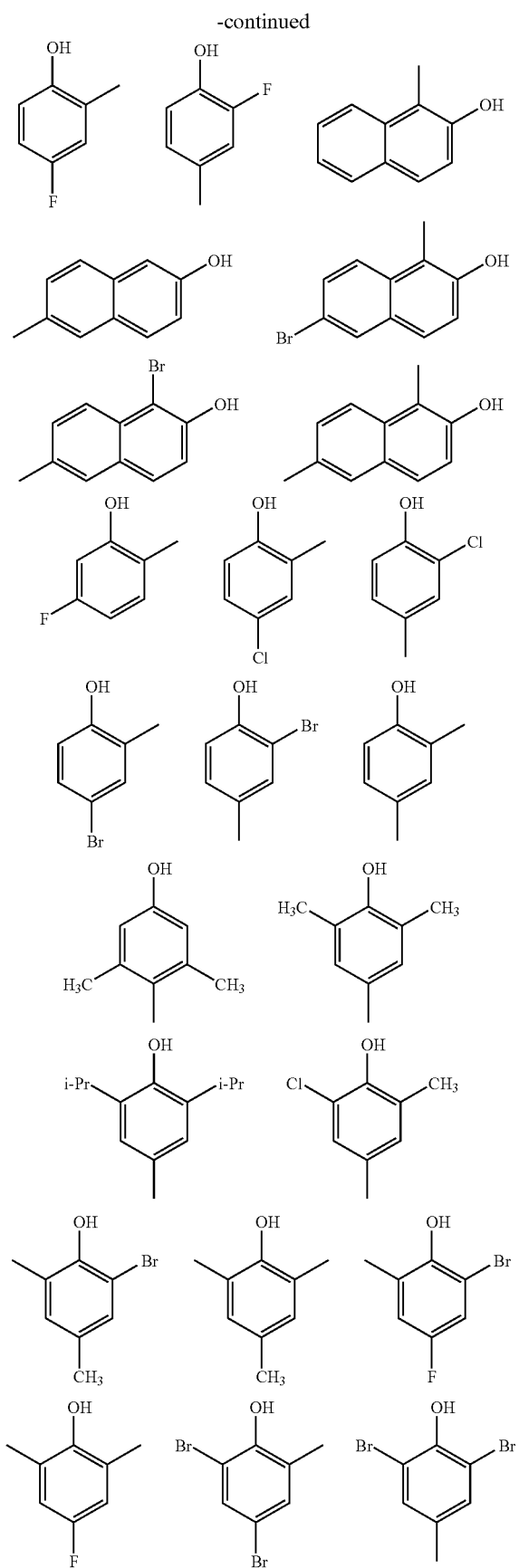
-continued
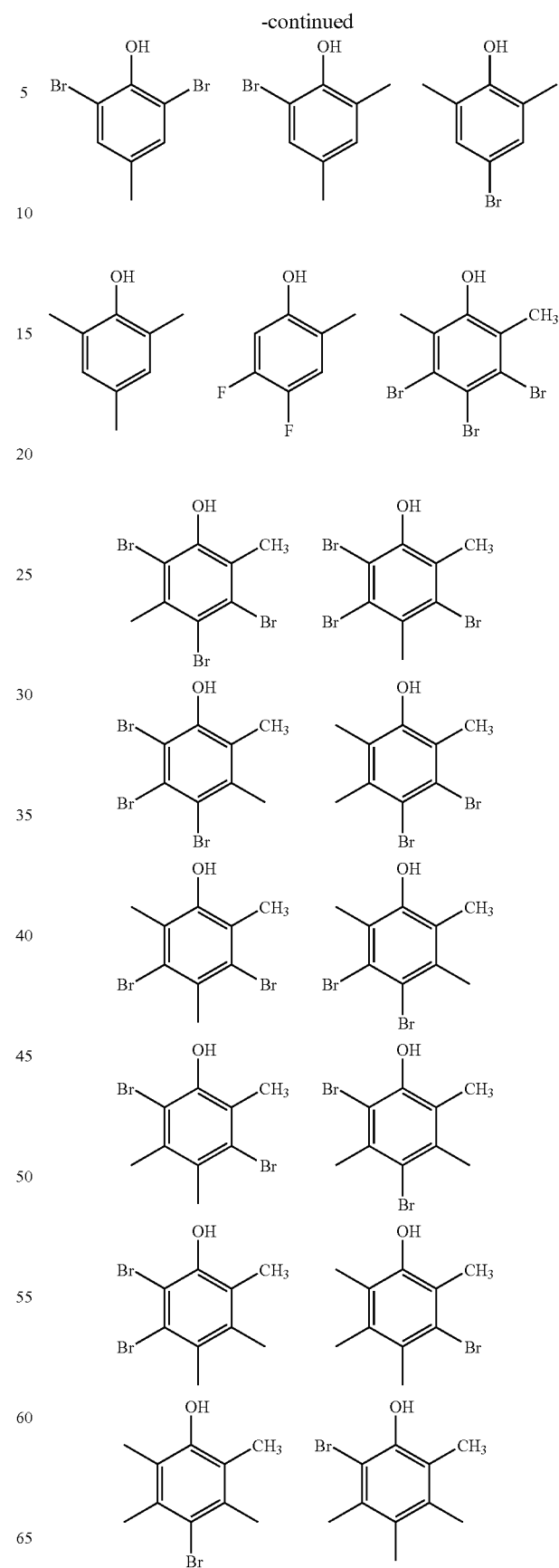

-continued
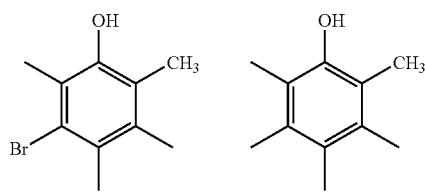 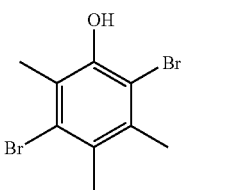
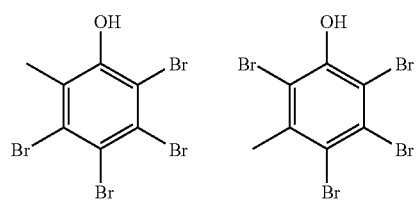 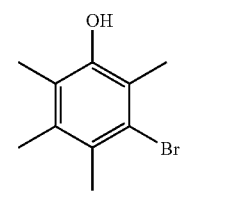
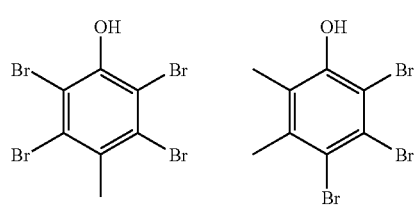 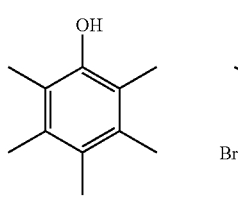
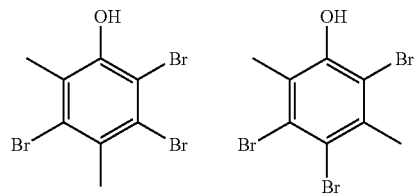 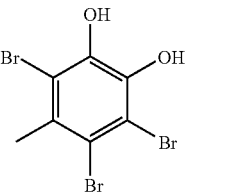
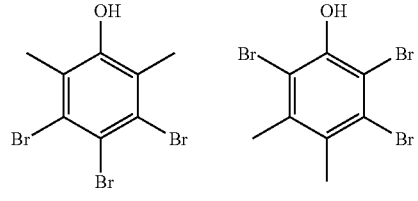 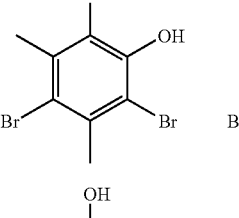
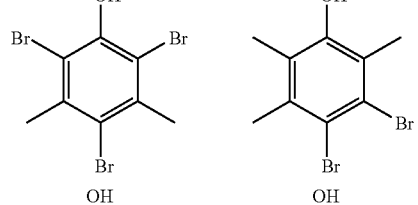 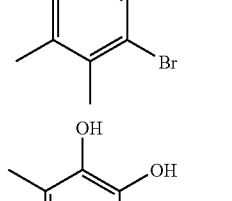
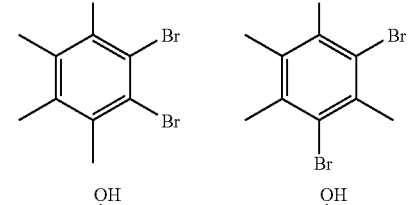 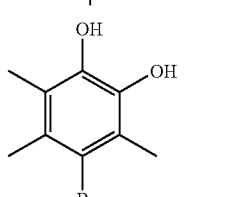
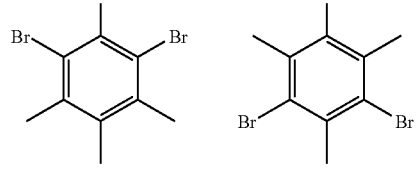 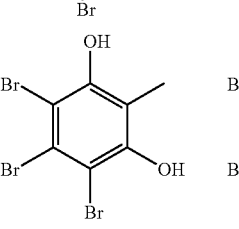

-continued
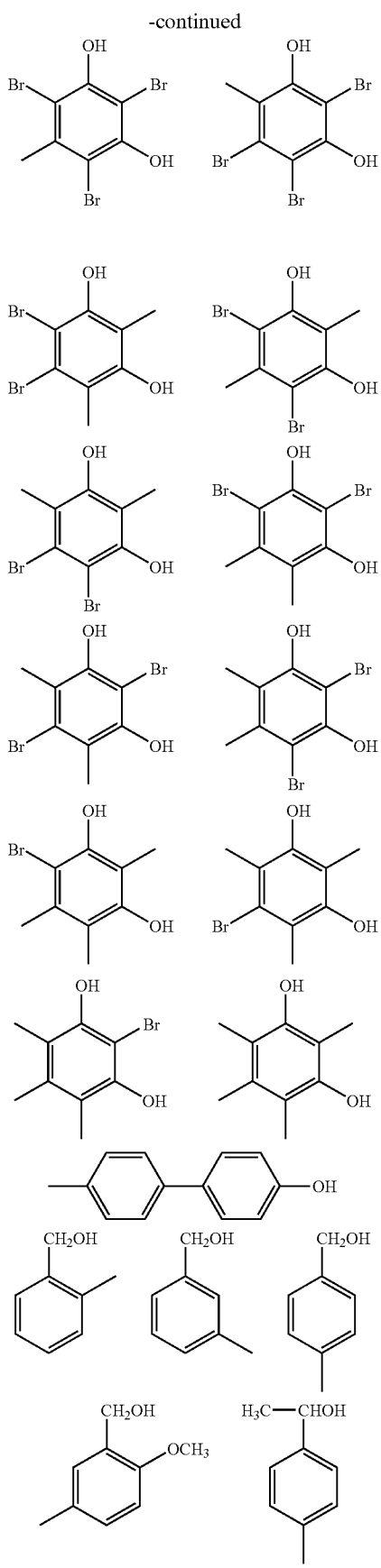
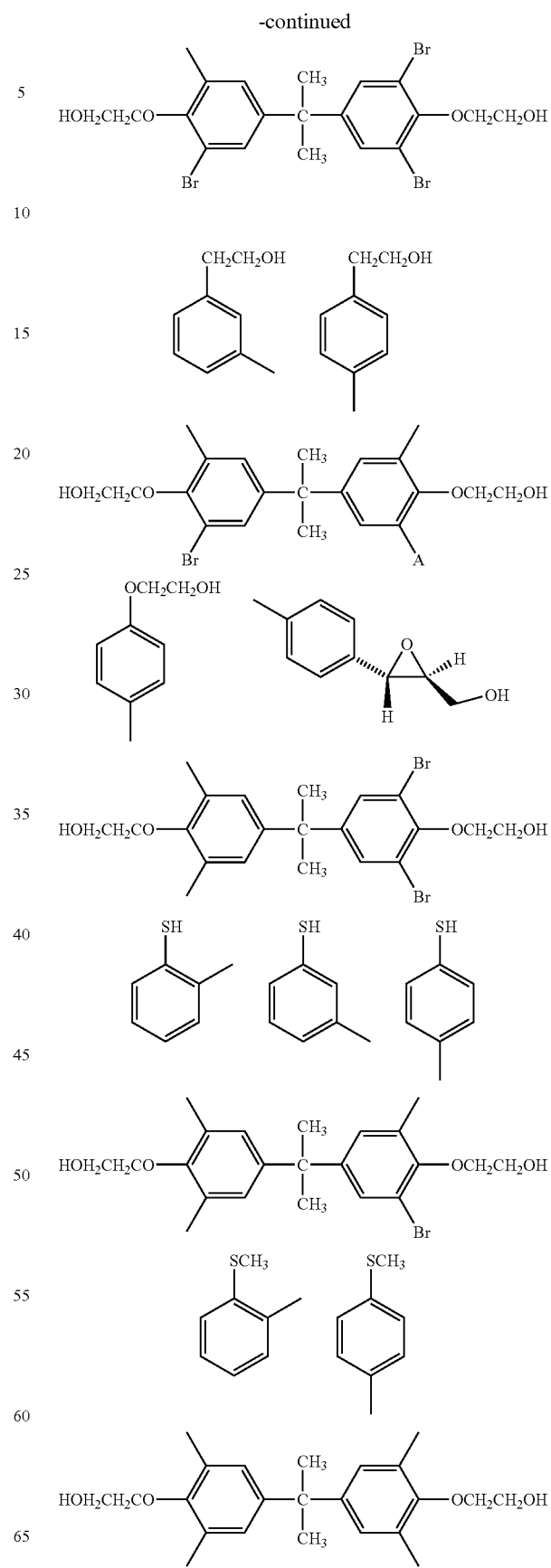

-continued

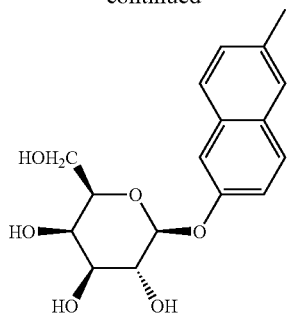

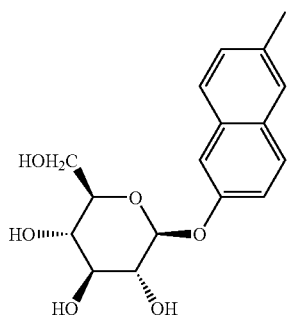

Functional groups are heteroatoms of groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica.

The nomenclature of d electron count, anionic ligands, neutral ligands, and oxidation state used here are described in length in the texts: Hegedus, L. S. Transition Metals in the Synthesis of Complex Organic Molecules 2nd Ed, University Science Press, 1999, Sausalito, Calif. and Collman, J. P. et. al. Principles and Applications of Organotransition Metal Chemistry. University Science Press, 1987, Sausalito, Calif.

Preferred E-phenoxide metal compounds include those represented by the following formulae:

wherein:

M is selected from groups 3-11 of the periodic table, preferably group 4 or 10, more preferably Ti or Ni.

$L^0$ represents an E-phenoxide ligand represented by the formula:

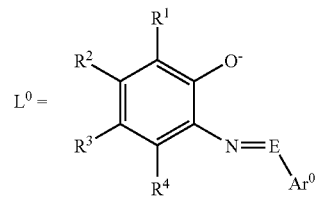

$L^1$ represents a formal anionic ligand;

$L^2$ represents a formal neutral ligand;

$L^3$ represents a formal anionic ligand that comprises a functional group;

a is greater than or equal to 1, preferably a=1, 2, 3 or 4, preferably a=1 or 2;

b is greater than or equal to 0, preferably b is 0, 1, 2, 3, 4, 5 or 6, more preferably b=0, 1 or 2, provided that b is not 0 or 1 in formula 2, 3 or 4 and b is not 0 in formula 6 or 7;

c is greater than or equal to 1, preferably c=1, 2, 3 or 4, more preferably 1 or 2;

E is nitrogen or phosphorus, preferably nitrogen;

N is nitrogen;

O is oxygen;

$Ar^0$ is an arene;

$R^1$-$R^4$ are each independently hydrogen, a hydrocarbyl, a substituted hydrocarbyl or a functional group, provided that $R^3$ and $R^4$ do not form a naphthyl ring; and $R^5$ is a hydride, a hydrocarbyl or a substituted hydrocarbyl.

Additional preferred E-phenoxide metal compounds include those represented by the following formulae:

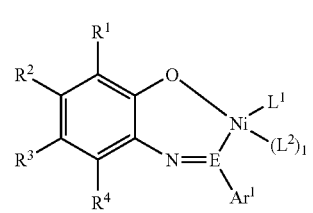

8

| $(L^0)_a(L^1)_{b-2}(L^2)_cM(R^5)_2$ | $(L^0)_a(L^1)_{b-2}(L^2)_cM(R^5)_1(L^3)_1$ | $(L^0)_a(L^1)_{b-2}(L^2)_cM(L^3)_2$ |
|---|---|---|
| 2 | 3 | 4 |
| $(L^0)_a(L^2)_cM$ | $(L^0)_a(L^1)_{b-1}(L^2)_cM(R^5)_1$ | $(L^0)_a(L^1)_{b-1}(L^2)_cM(L^3)_1$ |
| 5 | 6 | 7 |

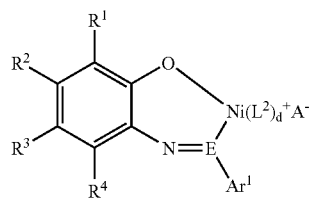
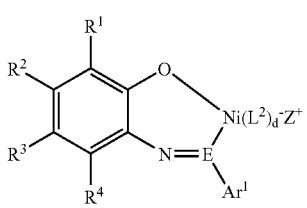
E is nitrogen or phosphorus, preferably nitrogen;
N is nitrogen;
O is oxygen
$Ar^1$ is arene; preferably one or more of:
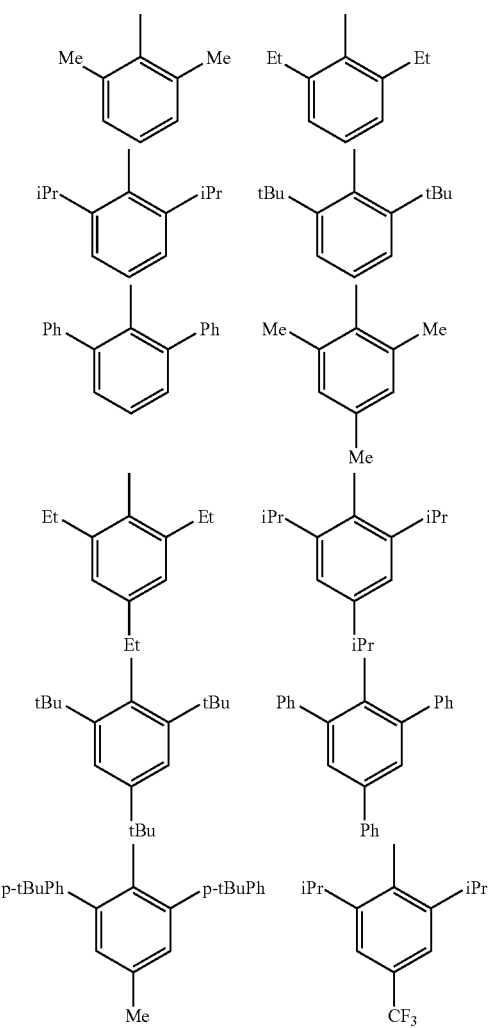
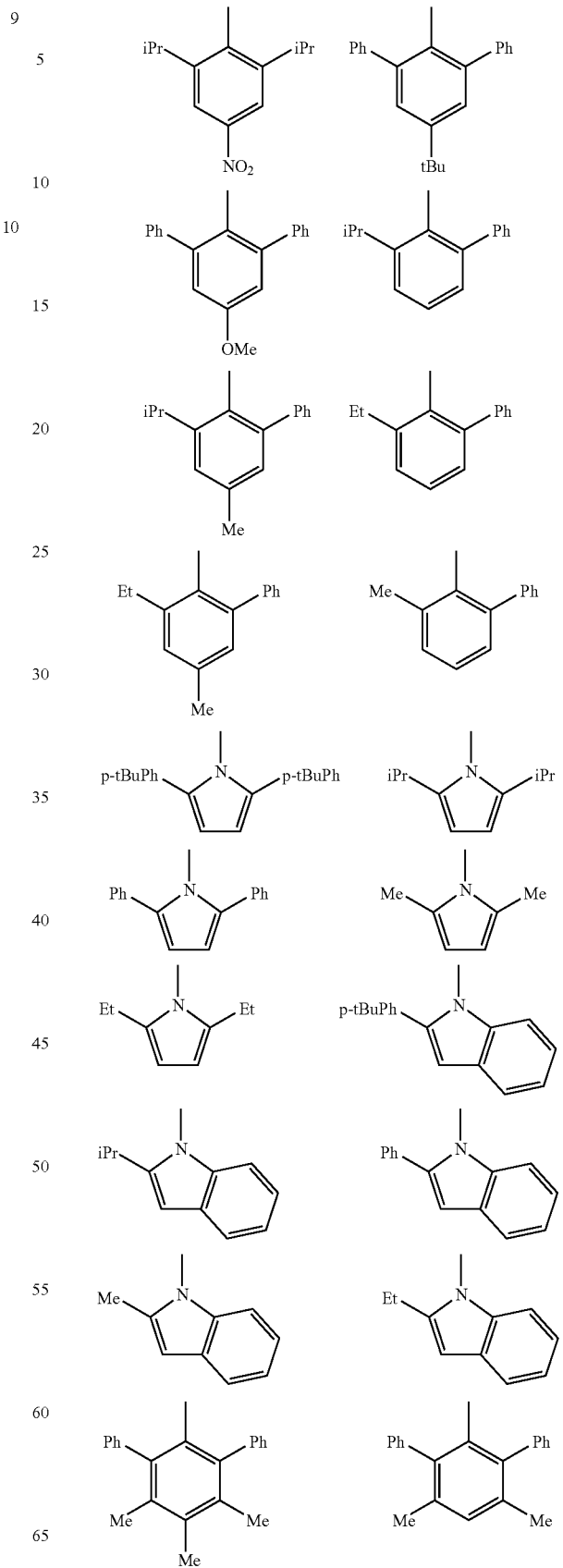

-continued

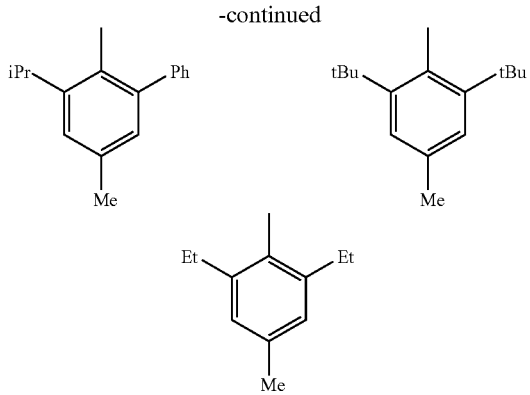

$R^1-R^4$ are each independently hydrogen, a hydrocarbyl, a substituted hydrocarbyl or a functional group, provided that $R^3$ and $R^4$ do not form a naphthyl ring;
$L^1$ represents a formal anionic ligand;
$L^2$ represents a formal neutral ligand;
"d" equals 1, 2 or 3, preferably 2;
$A^-$ is an anion that may or may not coordinate to Ni or may coordinate weakly to N; $A^-$ may be a non-coordinating anion, a substituted hydrocarbon or a functional group, preferably $A^-$ comprises one or more halides, carboxylates, phosphates, sulfates, sulfonates, borates, aluminates, alkoxides, thioalkoxides, anonic substituted hydrocarbons, or anionic metal complexes;
$Z^+$ is a cation, preferably a metal or metal complex of groups 1, 2, 11, or 12.

Preferably, the metal compound contains at least one formal neutral ligand coordinated to the metal in addition to the nitrogen or phosphorus of the E-phenoxide ligand(s).

The nickel compounds contain one E-phenoxide ligand and at least one formal neutral ligand. The remaining ligands in the coordination sphere of the metal compound are such that the compound attains a d electron count of 14-18. The nickel compound may be neutral or a charged species with an appropriate counterion.

Preferred metal compounds include those containing one azo-phenoxide ligand, one formal neutral ligand, and one formal anionic ligand.

Additional preferred azo-phenoxide metal compounds are represented by formula 11 and its steroisomers:

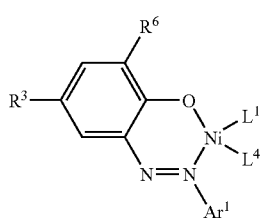

$L^1$ represents a formal anionic ligand;
$R^3$ is hydrogen, a hydrocarbyl, a substituted hydrocarbyl or a functional group;
$R^6$ is $C(R^7)_e$, e=2 or 3, $R^7$ is a hydrocarbon, a substituted hydrocarbon, or a functional group, two $R^7$ groups may be part of a common arene ring when e=2; Preferred non-limiting examples of $R^6$ include t-butyl, adamantyl, phenyl, naphthyl, anthracenyl.

$Ar^1$ is an arene;
$L^4$, is a formal neutral ligand, coordinated to the nickel in addition to the nitrogen of the azo-phenoxide ligand, based on carbon, nitrogen or phosphorus, preferably one or more alkenes, alkynes, nitriles, pyridines, aryl phosphines and phosphorus ylides. Non-limiting preferred examples of $L^4$ include:

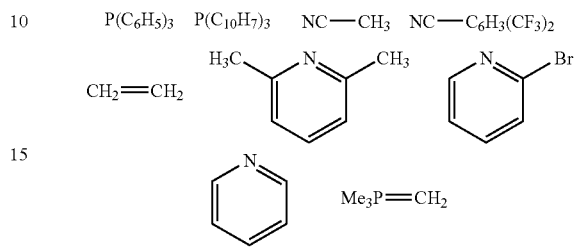

Particularly preferred azo-phenoxide compounds are represented by formula 12:

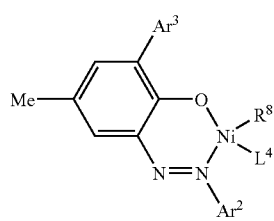

wherein:
$L^4$ represents a formal neutral ligand based on carbon, nitrogen or phosphorus preferably one or more alkenes, alkynes, nitriles, pyridines, aryl phosphines and or phosphorus ylides;
$R^8$ represents a formal anionic ligand which may be hydrogen or a hydrocarbon, preferably a hydride, methyl, ethyl, trimethylsilylmethyl, trimethylsilyl, phenyl, naphthyl, allyl, benzyl;
$Ar^2$ is a phenyl group substituted in the 2 and 6 positions by 2° hydrocarbons, 2° substituted hydrocarbons, 3° hydrocarbons, 3° substituted hydrocarbons, or arenes;
Me is methyl.

Preferred non-limiting examples of $Ar^2$ include:

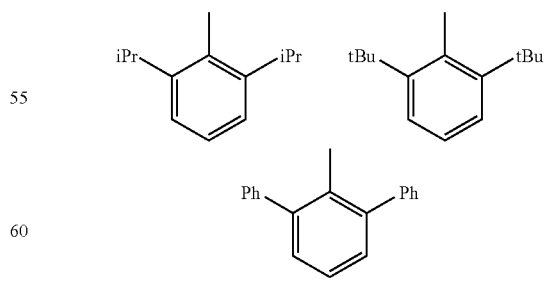

For purposes of this invention, where the terms 2° and 3° are used we mean that the hydrocarbon is 2° or 3° prior to substitution onto the arene ring. For example in the structures above the iPr is 2° and the tBu is 3°.

Ar³ is an arene. Preferred non-limiting examples of Ar³ include:

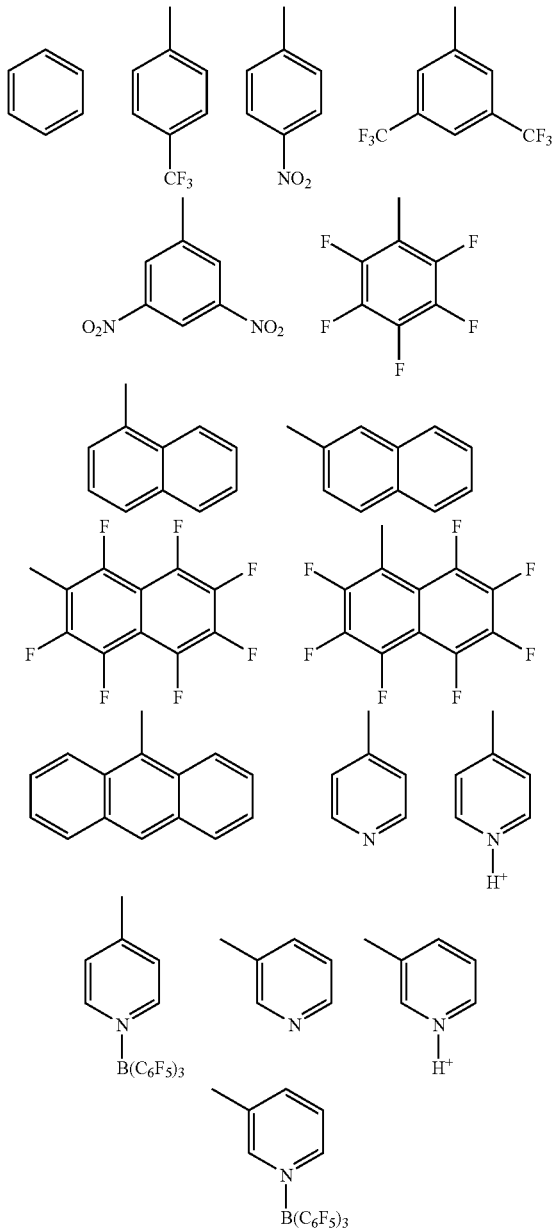

In another preferred embodiment the catalyst compounds described herein may be used in combination with other polymerization and or oligomerization catalysts. In a preferred embodiment the instant catalyst compounds are used in combination with catalyst compounds described in any of the following references:

1. Younkin, T. R.; Connor, E. F.; Henderson, J. I.; Friederich, S. K.; Grubbs, R. H.; Bansleben, D. A. *Science* 2000, 287, 460
2. Wang, C. Friederich, S.; Younkin, T. R.; Li, R. T.; Grubbs, R. H.; Bansleben, D. A.; Day, M. W. *Organometallics* 1998, 17, 3149
3. Johnson, L. K.; Bennett, A. M. A.; Wang, L.; Parthasarathy, A.; Hauptman, E.; Simpson, R. D.; Feldman, J.; Coughlin, E. B. WO 98/30609
4. Bansleben, D. A.; Friederich, S. K.; Younkin, T. R.; Grubbs, R. H.; Wang, C.; Li, R. T. WO 98/42664
5. Bansleben, D. A.; Friederich, S. K.; Younkin, T. R.; Grubbs, R. H.; Wang, C.; Li, R. T. WO 98/42665
6. Bansleben, D. A.; Connor, E. F.; Grubbs, R. H.; Henderson, J. I.; Younkin, T. R.; Nadjadi, A. R. WO 2000/56786
7. Bansleben, D. A.; Connor, B. F.; Grubbs, R. H.; Henderson, J. I.; Younkin, T. R.; Nadjadi, A. R. WO 2000/56787
8. Bansleben, D. A.; Friedrich, S. K.; Grubbs, R. H.; Li, R. T.; Connor, E. F.; Roberts, W. P. WO 2000/56781
9. Hicks, F.; Brookhart, M. *Organometallics* 2001, 20, 3217
10. Connor, E. F.; Younkin, T. R.; Henderson, J. I.; Hwang, S.; Grubbs, R. H.; Roberts, W. P.; Litzau, J. J. *J. Polym. Sci. A* 2002, 40, 2842
11. Schroeder, D. L.; Keim, W.; Zuideveld, M. A.; Mecking, S, *Macromolecules*, 2002, 35, 6071
12. Matsui, S.; Nitabaru, M.; Tsuru, K.; Fujita, T.; Suzuki, Y.; Takagi, Y.; Tanaka, H. EP 0 990 664 A1
13. Laali, K.; Szele, I.; Zollinger, H., *Helvetica Chimica Acta* 1983, 66, 1737
14. Petrillo, G.; Novi, M.; Garbarino, G.; Filiberti, M., *Tetrahedron* 1989, 45, 7411
15. Johnson, L. K.; Killian, C. M.; Arthur, S. D.; Feldman, J.; McCord, E. F.; McLain, S. J.; Kreutzer, K. A.; Bennett, M. A.; Coughlin, E. B.; Ittel, S. D.; Parthasarathy, A.; Tempel, D.; Brookhart, M. S. WO 96/23010
16. Johnson, L. K.; Mecking, S.; Brookhart, M. *J. Am. Chem. Soc.* 1996, 118,
17. Mecking, S.; Johnson, L. K.; Wang, L.; Brookhart, M. *J. Am. Chem. Soc.* 1998, 120, 888
18. Wang, L.; Hauptman, E.; Johnson, L. K.; McCord, E. F.; Wang, Y.; Ittel, S. D. WO 01/92342
19. Johnson, L.; Bennett, A.; Dobbs, K.; Hauptman, E.; Ionkin, A.; Ittel, S.; McCord, E.; McLain, S.; Radzewich, C.; Yin, Z.; Wang, L.; Wang, Y.; Brookhart, M. *Polym. Mat. Sci. Eng.* 2002, 86, 319
20. Wang, L.; Hauptman, E.; Johnson, L. K.; Marshall, W. J.; McCord, E. F.; Wang, Y.; Ittel, S. D.; Radzewich, C. E.; Kunitsky, K.; Ionkin, A. S. *Polym. Mat. Sci. Eng.* 2002, 2002, 322
21. Drent, E.; van Dijk, R.; van Ginkel, R.; van Oort, B.; Pugh, R. I. *Chem. Commun.* 2002, 744
22. Liu, W.; Malinoski, J. M.; Brookhart, M. *Organometallics* 2002, 21, 2836
23. Bansleben, D. A.; Friederich, S. K.; Younkin, T. R.; Grubbs, R. H.; Wang, C.; Li, R. T. U.S. Pat. No. 6,410,664
24. Bansleben, D. A.; Friederich, S. K.; Grubbs, R. H.; Li, R. T.; Wang, C.; Younkin, T. R. U.S. Pat. No. 6,143,857
25. Bansleben, D. A.; Connor, E. F.; Grubbs, R. H.; Roberts, W. P. U.S. Pat. No. 6,562,922
26. Mix, H.; Kurras, E.; Wilcke, F.-W.; Reihsig, J.; Schulz, W.; Fuhrmann, H.; Grassert, I.; Fuchs, W.; Meissner, J. DD 99556 Aug. 12, 1973
27. Bansleben, D. A.; Connor, E. F.; Grubbs, R. H.; Henderson, J. I.; Younkin, T. R. U.S. Pat. No. 6,506,704
28. Bansleben, D. A.; Connor, E. F.; Grubbs, R. H.; Henderson, J. I.; Younkin, T. R. WO 00/56785
29. Bansleben, D. A.; Connor, E. F.; Grubbs, R. H.; Henderson, J. I.; Nadjadi, A. R. Jr.; Younkin, T. R. U.S. Pat. No. 6,197,715
30. Bansleben, D. A.; Connor, E. F.; Grubbs, R. H.; Henderson, J. I.; Nadjadi, A. R. Jr.; Younkin, T. R. U.S. Pat. No. 6,197,714
31. Stibrany, R. T.; Schulz, D. N.; Kacker, S.; Patil, A. O.; Baugh, L. S.; Rucker, S. P.; Zushma, S.; Berluche, E.; Sissano, J. A. *Macromolecules* 2003, 36, 8584

32. Stibrany, R. T.; Schulz, D. N.; Kacker, S.; Patil, A. O. PCT Int. Appl. WO 99/30822 (Exxon), 1999
33. Stibrany, R. T.; Schulz, D. N.; Kacker, S.; Patil, A. O. U.S. Pat. No. 6,037,297 (Exxon), 2000
34. Stibrany, R. T.; Schulz, D. N.; Kacker, S.; Patil, A. O. U.S. Pat. No. 6,417,303 (ExxonMobil), 2002
35. Stibrany, R. T. U.S. Pat. No. 6,180,788 (Exxon), 2001
36. Stibrany, R. T.; Schulz, D. N.; Kacker, S.; Patil, A. O.; Baugh, L. S.; Rucker, S. P.; Zushma, S.; Berluche, E.; Sissano, J. A. *Polymeric Materials: Science & Engineering* 2002, 86, 325
37. Stibrany, R. T.; Schulz, D. N.; Kacker, S.; Patil, A. O.; Baugh, L. S.; Rucker, S. P.; Zushma, S.; Berluche, E.; Sissano, J. A. In *Beyond Metallocenes: Next-Generation Polymerization Catalysts*; Patil, A. O.; Hlatky, G. G., Eds.; ACS Symposium Series 857; American Chemical Society: Washington, D.C., 2003, 222.

Activators and Activation Methods for Catalyst Compounds

An activator is defined as any combination of reagents that increases the rate at which a metal compound, containing at least one E-phenoxide ligand and one formal neutral ligand, oligomerizes or polymerizes unsaturated monomers. An activator may also affect the molecular weight, degree of branching, comonomer content, or other properties of the oligomer or polymer. The E-phenoxide compounds according to the invention may be activated for oligomerization and or polymerization catalysis in any manner sufficient to allow coordination or cationic oligomerization and or coordination or cationic polymerization.

Generally speaking, successful oligomerization and/or polymerization catalysts contain a formal anionic ligand, such as hydride or hydrocarbyl, with an adjacent (cis) coordination site accessible to an unsaturated monomer. Coordination of an unsaturated monomer to the cis coordination site allows a migratory insertion reaction to form a metal alkyl. Repetition of this process causes chain growth. An activator is thus any combination of reagents that facilitates formation of a transition metal compound containing, in addition to at least one E-phenoxide ligand, cis coordinated olefin and hydride or hydrocarbyl.

When the E-phenoxide compound contains at least one hydride or hydrocarbyl ligand, activation can be achieved by removal of formal anionic or neutral ligands, of higher binding affinity than the unsaturated monomer. This removal, also called abstraction, process may have a kinetic rate that is first-order or non-first order with respect to the activator. Activators that remove formal anonic ligands are termed ionizing activators. Activators that remove formal neutral ligands are termed non-ionizing activators. Activators are typically strong Lewis-acids which may play either the role of ionizing or non-ionizing activator.

When the E-phenoxide compound does not contain at least one hydride or hydrocarbyl ligands, then activation may be a one step or multi step process. A step in this process includes coordinating a hydride or hydrocarbyl group to the metal compound. A separate activation step is removal of formal anionic or neutral ligands of higher binding affinity than the unsaturated monomer. These activation steps may occur in series or in parallel. These steps may occur in the presence of unsaturated monomers or these steps may occur prior to exposure to the monomers. More than one sequence of activation steps is possible to achieve activation.

The activator may also act to coordinate a hydride or hydrocarbyl group to the metal compound, containing at least one E-phenoxide ligand and one formal neutral ligand. When the E-phenoxide compound does not contain at least one hydride or hydrocarbyl ligands but does contain at least one functional group ligand, activation may be effected by substitution of the functional group with a hydride, hydrocarbyl or substituted hydrocarbyl group. This substitution may be effected with appropriate hydride or alkyl reagents of group 1, 2, 12, 13 elements as is known in the art. To achieve activation, it may be necessary to also remove formal anionic or neutral ligands of higher binding affinity than the unsaturated monomer.

Alumoxane and aluminum alkyl activators are capable of alkylation and abstraction activation.

The activator may also act to coordinate a hydride or hydrocarbyl group to the metal compound, containing at least one E-phenoxide ligand and one formal neutral ligand. If the E-phenoxide compound does not contain formal anionic ligands, then a hydride, hydrocarbyl or substituted hydrocarbyl may be coordinated to a metal using electrophilic proton or alkyl transfer reagents represented by $H^+(LB)_nA^-$, $(R^9)^+(LB)_nA^-$. $R^9$ is a hydrocarbyl or a substituted hydrocarbyl; LB is a Lewis-base, n=0, 1 or 2. Non-limiting examples of preferred Lewis-bases are diethyl ether, dimethyl ether, ethanol, methanol, water, acetonitrile, N,N-dimethylaniline. $A^-$ is an anion preferably a substituted hydrocarbon, a functional group, or a non-coordinating anion. Non-limiting examples of $A^-$ include halides, carboxylates, phosphates, sulfates, sulfonates, borates, aluminates, alkoxides, thioalkoxides, anionic substituted hydrocarbons, and anionic metal complexes.

A. Alumoxane and Aluminum Alkyl Activators

In one embodiment, one or more alumoxanes are utilized as an activator in the catalyst composition of the invention. Alumoxanes, sometimes called aluminoxanes in the art, are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180.

When the activator is an alumoxane (modified or unmodified), some embodiments select the maximum amount of activator at a 5000-fold molar excess Al/M over the catalyst precursor (per metal catalytic site). The minimum activator-to-catalyst-precursor is typically a 1:1 molar ratio.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279

586, EP-A-0 594-218 and EP-B1-0 586 665, and PCT publications WO 94/10180 and WO 99/15534, all of which are herein fully incorporated by reference. It may be preferable to use a visually clear methylalumoxane. A cloudy or gelled alumoxane can be filtered to produce a clear solution or clear alumoxane can be decanted from the cloudy solution. Another preferred alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum and the like.

B. Ionizing Activators

It is within the scope of this invention to use an ionizing or stoichiometric activator, neutral or ionic, such as tri(n-butyl)ammonium tetrakis (pentafluorophenyl)boron, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Preferred activators include a cation and an anion component, and may be represented by the following formula:

$$(W^{f+})_g(NCA^{h-})_i$$

$W^{f+}$ is a cation component having the charge f+
$NCA^{h-}$ is a non-coordinating anion having the charge h−
f is an integer from 1 to 3.
h is an integer from 1 to 3.
g and h are constrained by the relationship: $(g)\times(f)=(h)\times(i)$.

The cation component, $(W^{f+})$ may include Bronsted acids such as protons or protonated Lewis bases or reducible Lewis acids capable of protonating or abstracting a moiety, such as an akyl or aryl, from an analogous metallocene or Group 15 containing transition metal catalyst precursor, resulting in a cationic transition metal species.

In a preferred embodiment, the activators include a cation and an anion component, and may be represented by the following formula:

$$(LB-H^{f+})_g(NCA^{h-})_i$$

wherein
LB is a neutral Lewis base;
H is hydrogen;
$NCA^{h-}$ is a non-coordinating anion having the charge h−
f is an integer from 1 to 3,
h is an integer from 1 to 3,
g and h are constrained by the relationship: $(g)\times(f)=(h)\times(i)$.

The activating cation $(W^{f+})$ may be a Bronsted acid, $(LB-H^{f+})$, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene and mixtures thereof.

The activating cation $(W^{f+})$ may also be an abstracting moiety such as silver, carboniums, tropylium, carbeniums, ferroceniums and mixtures, preferably carboniums and ferroceniums. Most preferably $(W^{f+})$ is triphenyl carbonium or N,N-dimethylanilinium.

The anion component $(NCA^{h-})$ includes those having the formula $[T^{j+}Qk]^{h-}$ wherein j is an integer from 1 to 3; k is an integer from 2 to 6; k−j=h; T is an element selected from Group 13 or 15 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $(NCA^{h-})$ also include diboron compounds as disclosed in U.S. Pat. No. 5,447,895, which is fully incorporated herein by reference.

Additional suitable anions are known in the art and will be suitable for use with the catalysts of the invention. See in particular, U.S. Pat. No. 5,278,119 and the review articles by S. H. Strauss, "The Search for Larger and More Weakly Coordinating Anions", Chem. Rev., 93, 927-942 (1993) and C. A. Reed, "Carboranes: A New Class of Weakly Coordinating Anions for Strong Electrophiles, Oxidants and Superacids", Acc. Chem. Res., 31, 133-139 (1998).

Illustrative, but not limiting examples of boron compounds which may be used as an activating cocatalyst in the preparation of the improved catalysts of this invention are tri-substituted ammonium salts such as:
trimethylammonium tetraphenylborate,
triethylammonium tetraphenylborate,
tripropylammonium tetraphenylborate,
tri(n-butyl)ammonium tetraphenylborate, tri(t-butyl)ammonium tetraphenylborate,
N,N-dimethylanilinium tetraphenylborate,
N,N-diethylanilinium tetraphenylborate,
N,N-dimethyl-(2,4,6-trimethylanilinium)tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl-(2,4,6-trimethylanilinium)tetrakis(pentafluorophenyl)borate,
trimethylammonium tetrakis-(2,3,4,6-tetrafluorophenylborate,
triethylammonium tetrakis-(2,3,4,6-tetrafluorophenyl)borate,
tripropylammonium tetrakis-(2,3,4,6-tetrafluorophenyl)borate,
tri(n-butyl)ammonium tetrakis-(2,3,4,6-tetrafluoro-phenyl)borate,
dimethyl(t-butyl)ammonium tetrakis-(2,3,4,6-tetrafluorophenyl)borate,
N,N-dimethylanilinium tetrakis-(2,3,4,6-tetrafluorophenyl)borate,
N,N-diethylanilinium tetrakis-(2,3,4,6-tetrafluoro-phenyl)borate, and
N,N-dimethyl-(2,4,6-trimethylanilinium)tetrakis-(2,3,4,6-tetrafluorophenyl)borate;
dialkyl ammonium salts such as: di-(i-propyl)ammonium tetrakis(pentafluorophenyl)borate, and dicyclohexylammonium tetrakis(pentafluorophenyl)borate; and tri-substituted phosphonium salts such as: triphenylphosphonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate.

Most preferably, the ionic stoichiometric activator is N,N-dimethylanilinium tetra(perfluorophenyl)borate and/or triphenylcarbenium tetra(perfluorophenyl)borate.

In one embodiment, activation methods using ionizing ionic compounds not containing an active proton but capable of producing an analogous metallocene catalyst cation and their non-coordinating anion are also contemplated and are described in EP-A-0 426 637, EP-A-0 573 403 and U.S. Pat. No. 5,387,568, which are all herein incorporated by reference.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Non-coordinating anions useful in accordance with this invention are those that are compatible, stabilize the metal cation in the sense of balancing its ionic charge, yet retain sufficient liability to permit displacement by an ethylenically or acetylenically unsaturated monomer during polymerization. These types of cocatalysts sometimes use tri-isobutyl aluminum or tri-octyl aluminum as a scavenger.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.* 2000, 100, 1391.

When the E-phenoxide complex does not contain at least one hydride or hydrocarbyl ligand but does contain at least one functional group ligand, such as chloride, amido or alkoxy ligands, and the functional group ligands are not capable of discrete ionizing abstraction with the ionizing, anion pre-cursor compounds, these functional group ligands can be converted via known alkylation reactions with organometallic compounds such as lithium or aluminum hydrides or alkyls, alkylalumoxanes, Grignard reagents, etc. See EP-A-0 500 944, EP-A1-0 570 982 and EP-A1-0 612 768 for analogous processes describing the reaction of alkyl aluminum compounds with analogous dihalide substituted metallocene compounds prior to or with the addition of activating noncoordinating anion precursor compounds.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl)boron can be used with methylalumoxane.

C. Non-Ionizing Activators

Activators are typically strong Lewis-acids which may play either the role of ionizing or non-ionizing activator. Activators previously described as ionizing activators may also be used as non-ionizing activators.

Abstraction of formal neutral ligands may be achieved with Lewis acids that display an affinity for the formal neutral ligands. These Lewis acids are typically unsaturated or weakly coordinated. Examples of non-ionizing activators include $R^{10}(R^{11})_3$, where $R^{10}$ is a group 13 element and $R^{11}$ is a hydrogen, a hydrocarbyl, a substituted hydrocarbyl, or a functional group. Typically, $R^{11}$ is an arene or a perfluorinated arene. Non-ionizing activators also include weakly coordinated transition metal compounds such as low valent olefin complexes.

Non-limiting examples of non-ionizing activators include $BMe_3$, $BEt_3$, $B(iBu)_3$, $BPh_3$, $B(C_6F_5)_3$, $AlMe_3$, $AlEt_3$, $Al(iBu)_3$, $AlPh_3$, $B(C_6F_5)_3$, alumoxane, CuCl, Ni(1,5-cyclooctadiene)$_2$.

Additional neutral Lewis-acids are known in the art and will be suitable for abstracting formal neutral ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.* 2000, 100, 1391.

Preferred non-ionizing activators include $R^{10}(R^{11})_3$, where $R^{10}$ is a group 13 element and $R^{11}$ is a hydrogen, a hydrocarbyl, a substituted hydrocarbyl, or a functional group. Typically, $R^{11}$ is an arene or a perfluorinated arene.

More preferred non-ionizing activators include $B(R^{12})_3$, where $R^{12}$ is a an arene or a perfluorinated arene. Even more preferred non-ionizing activators include $B(C_6H_5)_3$ and $B(C_6F_5)_3$. A particularly preferred non-ionizing activator is $B(C_6F_5)_3$. More preferred activators are ionizing and non-ionizing activators based on perfluoroaryl borane and perfluoroaryl borates such as $PhNMe_2H^+ B(C_6F_5)_4^-$, $(C_6H_5)_3 C^+ B(C_6F_5)_4^-$, and $B(C_6F_5)_3$.

It appears that alumoxane and aluminum alkyl activators may act to reduce molecular weight. While not wishing to be bound by theory, we believe however, that in some embodiments the alumoxane or aluminum alkyl may not affect molecular weight or may even increase it.

In general the combined metal compounds and the activator are combined in ratios of about 1000:1 to about 0.5:1. In a preferred embodiment the metal compounds and the activator are combined in a ratio of about 300:1 to about 1:1, preferably about 150:1 to about 1:1, for boranes, borates, aluminates, etc. the ratio is preferably about 1:1 to about 10:1 and for alkyl aluminum compounds (such as diethylaluminum chloride combined with water) the ratio is preferably about 0.5:1 to about 10:1.

In a preferred embodiment the ratio of the first catalyst to the second or additional catalyst is 5:95 to 95:5, preferably 25:75 to 75:25, even more preferably 40:60 to 60:40.

In another embodiment the catalyst compositions of this invention include a support material or carrier. For example, the one or more catalyst components and/or one or more activators may be deposited on, contacted with, vaporized with, bonded to, or incorporated within, adsorbed or absorbed in, or on, one or more supports or carriers.

The support material is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is in the range of from about 50 to about 500 $m^2/g$, pore volume of from about 0.5 to about 3.5 cc/g and average particle size of from about 10 to about 200 μm. Most preferably the surface area of the support material is in the range is from about 100 to about 400 $m^2/g$, pore volume from about 0.8 to about 3.0 cc/g and average particle size is from about 5 to about 100 μm. The average pore size of the carrier of the invention typically has pore size in the range of from 10 to 1000 Å, preferably 50 to about 500 Å, and most preferably 75 to about 350 Å.

Monomers

For purposes of this invention and the claims thereto the term unsaturated monomer includes olefins, polar monomers, dienes, cyclics, and the like.

In a preferred embodiment the catalyst compounds of this invention are used to polymerize at least one olefin monomer and at least one polar monomer. For purposes of this invention and the claims thereto, an olefin monomer is defined to be a monomer comprising only carbon and hydrogen having at least one unsaturation, and a polar monomer is defined to be a monomer comprising carbon, hydrogen and at least one heteroatom, and having at least one unsaturation. Preferred olefin monomers include $C_2$ to $C_{100}$ olefins, preferably $C_2$ to $C_{60}$ olefins, preferably $C_2$ to $C_{40}$ olefins, preferably $C_2$ to $C_{20}$ olefins, preferably $C_2$ to $C_{12}$ olefins. In some embodiments, preferred olefin monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins, preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, undecene, dodecene, 4-methyl-pentene-1,3-methyl pentene-1,3,5,5-trimethyl-hexene-1, and 5-ethyl-1-nonene.

Preferred olefin monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene, and allyl benzene.

Non aromatic cyclic group containing monomers are also preferred for use as olefin monomers. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclopentane, cyclopentene, cyclohexene, cyclobutene, vinyladamantane and the like.

Preferred diolefin (also referred to as diene) monomers useful in this invention as olefin monomers include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, cyclohexadiene, vinylnorbornene, norbornadiene, ethylidene norbornene, divinylbenzene, dicyclopentadiene, or higher ring containing diolefins with or without substituents at various ring positions. Alternately, the diolefin monomer may be selected from linear or branched aliphatic dienes having a non-di-vinyl structure. These diolefins have a structure in which one olefin is a vinyl group and the remaining olefin is an internal 1,2-disubstituted, trisubstituted, or tetrasubstituted olefin. Preferred non-di-vinyl diolefins include 7-methyl-1,6-octadiene, 1,4-hexadiene, and 4-vinyl-1-cyclohexene.

Preferred polar monomers for use in this invention include monomers containing a group 13, 14 (other than carbon), 15, 16, or 17 heteroatom; preferably monomers containing one or more of aluminum, boron, silicon, nitrogen, oxygen, sulfur, phosphorus, bromine, chlorine, iodine, fluorine, and the like. It is particularly preferred that the heteroatom(s) is nitrogen and or oxygen. The heteroatom may be attached directly to the double bond of the olefin monomer or cyclic monomer, or alternately may be attached to any other carbon atom(s). If desired, the heteroatom may comprise part of a ring structure. Preferred polar monomers include monomers containing one or more heteroatom containing groups, which are selected from the group consisting of: siloxy, silane, alcohol (hydroxy), dihydroxy, phenol, acetal, epoxide, carbonate, methyl ether, ethyl ether, propyl ether, butyl ether, isobutyl ether, sec-butyl ether, tert-butyl ether, cyclohexyl ether, phenyl ether, benzyl ether, carboxylic acid, carboxylic salt, carboxylic anhydride, methyl ester, ethyl ester, propyl ester, isopropyl ester, butyl ester, isobutyl ester, sec-butyl ester, tert-butyl ester, cyclohexyl ester, phenyl ester, benzyl ester, acetate, nitrile, imine, trimethylsilyl ether, di-tert-butylmethylsilyl ether, trimethylsilane and other alkyl silanes, borane, alkyl boranes, aryl boranes, alanes, aluminates, carboxylic acid trimethylsilyl ether, carboxylic acid di-tert-butylmethylsilyl ether, sulfonate, nitro, amine, amide, aldehyde, ketone, thiol, and sulfide. In some embodiments, it is preferred that the heteroatom containing group be selected from the group consisting of hydroxy, dihydroxy, acetal, trimethylsilyl ether, acetate, methyl ester, ethyl ester, and carbonate. In another embodiment the polar monomer comprises carbon monoxide.

In a preferred embodiment, the polar monomers may be selected from linear alpha-vinyl, omega-polar monomers in which the heteroatom containing group(s) are attached to the carbon termini most distant from the vinyl unit (or also to the next most distant carbon, for the case of multiple heteroatom containing groups). More preferably, the linear alpha-vinyl, omega-polar monomers contain from 2 to 30 carbon atoms, with 0 to 28 carbon atoms separating the vinyl and heteroatom. Most preferably, the linear alpha-vinyl, omega-polar monomers contain from 2 to 18 carbon atoms, with 0 to 11 carbon atoms separating the vinyl and heteroatoms. In some cases, the linear alpha-vinyl, omega-polar monomer may include a cyclic group as part of the heteroatom containing group, wherein the cyclic group does not contain the polymerizing olefin or serve to separate the vinyl and polar groups. Preferred linear alpha-vinyl, omega-polar monomers include: 3-buten-1-ol, 2-methyl-3-buten-1-ol, 3-butene-1,2-diol, 4-penten-1-ol, 4-pentene-1,2-diol, 5-hexen-1-ol, 5-hexene-1,2-diol, 6-hepten-1-ol, 6-heptene-1,2-diol, 7-octen-1-ol, 7-octene-1,2-diol, 8-nonen-1-ol, 8-nonene-1,2-diol, 9-decen-1-ol, 9-decene-1,2-diol, 10-undecen-1-ol, 10-undecene-1,2-diol, 11-dodecen-1-ol, 11-dodecene-1,2-diol, 12-tridecen-1-ol, 12-tridecene-1,2-diol, 4-(3-butenyl)-2,2-dimethyldioxolane, 1,2-epoxy-3-butene (butadiene monoxide), 2-methyl-2-vinyloxirane, 1,2-epoxy-4-pentene, 1,2-epoxy-5-hexene, 1,2-epoxy-6-heptene, 1,2-epoxy-7-octene, 1,2-epoxy-8-nonene, 1,2-epoxy-9-decene, 1,2-epoxy-10-undecene, 1,2-epoxy-11-dodecene, 1,2-epoxy-12-tridecene, 3-buten-1-ol methyl ether, 4-penten-1-ol methyl ether, 5-hexen-1-ol methyl ether, 6-hepten-1-ol methyl ether, 7-octen-1-ol methyl ether, 8-nonen-1-ol methyl ether, 9-decen-1-ol methyl ether, 10-undecen-1-ol methyl ether, 11-dodecen-1-ol methyl ether, 12-tridecen-1-ol methyl ether, 4-pentenoic acid, 2,2-dimethyl-4-pentenoic acid, 5-hexenoic acid, 6-heptenoic acid, trans-2,4-pentadienoic acid, 2,6-heptadienoic acid, 7-octenoic acid, 8-nonenoic acid, 9-decenoic acid, 10-undecenoic acid, 11-dodecenoic acid, 12-tridecenoic acid, methyl 4-pentenoate, methyl 5-hexenoate, methyl 6-heptenoate, methyl 7-octenoate, methyl 8-nonenoate, methyl 9-decenoate, methyl 10-undecenoate, ethyl 10-undecenoate, methyl 11-dodecenoate, methyl 12-tridecenoate, 3-butenyl acetate, pentenyl acetate, hexenyl acetate, heptenyl acetate, octenyl acetate, nonenyl acetate, decenyl acetate, undecenyl acetate, dodecenyl acetate, tridecenyl acetate, 4-pentene-1-nitrile, 5-hexene-1-nitrile, 6-heptene-1-nitrile, 7-octene-1-nitrile, 8-nonene-1-nitrile, 9-decene-1-nitrile, 10-undecene-1-nitrile, 11-dodecene-1-nitrile, 12-tridecene-1-nitrile, 3-buten-1-ol trimethylsilyl ether, 4-penten-1-ol trimethylsilyl ether, 5-hexen-1-ol trimethylsilyl ether, 6-hepten-1-ol trimethylsilyl ether, 7-octen-1-ol trimethylsilyl ether, 8-nonen-1-ol trimethylsilyl ether, 9-decen-1-ol trimethylsilyl ether, 10-undecen-1-ol trimethylsilyl ether, 11-dodecen-1-ol trimethylsilyl ether, 12-tridecen-1-ol trimethylsilyl ether, 2,2-dimethyl-4-pentenal, undecylenic aldehyde, 2,4-dimethyl-2,6-heptadienal, 5-hexen-2-one, and nonafluoro-1-hexene. In a preferred embodiment, the linear alpha-vinyl, omega-polar monomers are selected from the group consisting of: 7-octen-1-ol, 7-octen-1-ol trimethylsilyl ether, and octenyl acetate.

Alternately, the polar monomers be selected from cyclic polar monomers, in which the heteroatom(s) or heteroatom containing group are attached to a carbon forming part of the ring structure which either contains the polymerizing olefin or separates the vinyl and heteroatom groups. Preferred cyclic polar monomers include: 5-norbornene-2-carbonitrile, 5-norbornene-2-carboxaldehyde, 5-norbornene-2-carboxylic acid, cis-5-norbornene-endo-2,3-dicarboxylic acid, cis-5-norbornene-2-endo-3-exo-dicarboxylic acid, 5-norbornene-2-carboxylic acid methyl ester, cis-5-norbornene-endo-2,3-dicarboxylic anhydride, cis-5-norbornene-exo-2,3-dicarboxylic anhydride, 5-norbornene-2-endo-3-endo-dimethanol, 5-norbornene-2-endo-3-exo-dimethanol, 5-norbornene-2-exo-3-exo-dimethanol, 5-norbornene-2,2,-dimethanol, 5-norbornene-2-methanol, 5-norbornen-2-ol, 5-norbornen-2-ol trimethylsilyl ether, 5-norbornen-2-ol methyl ether, 5-norbornen-2-yl acetate, 1-[2-(5-norbornene-2-yl)ethyl]-3,5,7,9,11,13,15-heptacyclopentylpentacyclo[9.5.1.1$^{3,9}$.1$^{5,15}$.1$^{7,13}$]octasiloxane, 2-benzoyl-5-norbornene, tricyclo[4.2.1.0$^{0,0}$]non-7-ene-3-carboxylic acid tert-butyl ester, tricyclo[4.2.1.0$^{0,0}$]non-7-ene-3,4-dicarboxylic acid tert-butyl ester, tricyclo[4.2.1.0$^{0,0o}$]non-7-ene-3,4-dicarboxylic acid anhydride, N-butyl-tricyclo[4.2.1.0$^{0,0}$]non-7-ene-3,4-dicarboxyimide, 2-cyclopenten-1-one ethylene ketal, and vinylene carbonate. In another preferred embodiment, the cyclic polar monomers are selected from the group consisting of 5-norbornen-2-yl acetate, 5-norbornen-2-ol, and 5-norbornen-2-ol trimethylsilyl ether.

In a preferred embodiment the polar monomer is selected from the group consisting of carbon monoxide, 3-buten-1-ol, 2-methyl-3-buten-1-ol, 3-butene-1,2-diol, 4-penten-1-ol, 4-pentene-1,2-diol, 5-hexen-1-ol, 5-hexene-1,2-diol, 6-hepten-1-ol, 6-heptene-1,2-diol, 7-octen-1-ol, 7-octene-1,2-diol, 8-nonen-1-ol, 8-nonene-1,2-diol, 9-decen-1-ol, 9-decene-1,2-diol, 10-undecen-1-ol, 10-undecene-1,2-diol, 11-dodecen-1-ol, 11-dodecene-1,2-diol, 12-tridecen-1-ol, 12-tridecene-1,2-diol, 4-(3-butenyl)-2,2-dimethyldioxolane, 1,2-epoxy-3-butene (butadiene monoxide), 2-methyl-2-vinyloxirane, 1,2-epoxy-4-pentene, 1,2-epoxy-5-hexene, 1,2-epoxy-6-heptene, 1,2-epoxy-7-octene, 1,2-epoxy-8-nonene, 1,2-epoxy-9-decene, 1,2-epoxy-10-undecene, 1,2-epoxy-11-dodecene, 1,2-epoxy-12-tridecene, 3-buten-1-ol methyl ether, 4-penten-1-ol methyl ether, 5-hexen-1-ol methyl ether, 6-hepten-1-ol methyl ether, 7-octen-1-ol methyl ether, 8-nonen-1-ol methyl ether, 9-decen-1-ol methyl ether, 10-undecen-1-ol methyl ether, 11-dodecen-1-ol methyl ether, 12-tridecen-1-ol methyl ether, 4-pentenoic acid, 2,2-dimethyl-4-pentenoic acid, 5-hexenoic acid, 6-heptenoic acid, trans-2,4-pentadienoic acid, 2,6-heptadienoic acid, 7-octenoic acid, 8-nonenoic acid, 9-decenoic acid, 10-undecenoic acid, 11-dodecenoic acid, 12-tridecenoic acid, methyl 4-pentenoate, methyl 5-hexenoate, methyl 6-heptenoate, methyl 7-octenoate, methyl 8-nonenoate, methyl 9-decenoate, methyl 10-undecenoate, ethyl 10-undecenoate, methyl 11-dodecenoate, methyl 12-tridecenoate, 3-butenyl acetate, pentenyl acetate, hexenyl acetate, heptenyl acetate, octenyl acetate, nonenyl acetate, decenyl acetate, undecenyl acetate, dodecenyl acetate, tridecenyl acetate, 4-pentene-1-nitrile, 5-hexene-1-nitrile, 6-heptene-1-nitrile, 7-octene-1-nitrile, 8-nonene-1-nitrile, 9-decene-1-nitrile, 10-undecene-1-nitrile, 11-dodecene-1-nitrile, 12-tridecene-1-nitrile, 3-buten-1-ol trimethylsilyl ether, 4-penten-1-ol trimethylsilyl ether, 5-hexen-1-ol trimethylsilyl ether, 6-hepten-1-ol trimethylsilyl ether, 7-octen-1-ol trimethylsilyl ether, 8-nonen-1-ol trimethylsilyl ether, 9-decen-1-ol trimethylsilyl ether, 10-undecen-1-ol trimethylsilyl ether, 11-dodecen-1-ol trimethylsilyl ether, 12-tridecen-1-ol trimethylsilyl ether, 2,2-dimethyl-4-pentenal, undecylenic aldehyde, 2,4-dimethyl-2,6-heptadienal, 5-hexen-2-one, nonafluoro-1-hexene, 5-norbornene-2-carbonitrile, 5-norbornene-2-carboxaldehyde, 5-norbornene-2-carboxylic acid, cis-5-norbornene-endo-2,3-dicarboxylic acid, cis-5-norbornene-2-endo-3-exo-dicarboxylic acid, 5-norbornene-2-carboxylic acid methyl ester, cis-5-norbornene-endo-2,3-dicarboxylic anhydride, cis-5-norbornene-exo-2,3-dicarboxylic anhydride, 5-norbornene-2-endo-3-endo-dimethanol, 5-norbornene-2-endo-3-exo-dimethanol, 5-norbornene-2-exo-3-exo-dimethanol, 5-norbornene-2,2,-dimethanol, 5-norbornene-2-methanol, 5-norbornen-2-ol, 5-norbornen-2-ol trimethylsilyl ether, 5-norbornen-2-ol methyl ether, 5-norbornen-2-yl acetate, 1-[2-(5-norbornene-2-yl)ethyl]-3,5,7,9,11,13,15-heptacyclopentylpentacyclo[9.5.1.1$^{3,9}$.1$^{5,15}$.1$^{7,13}$]octasiloxane, 2-benzoyl-5-norbornene, tricyclo[4.2.1.0$^{0,0}$]non-7-ene-3-carboxylic acid tert-butyl ester, tricyclo[4.2.1.0$^{0,0}$]non-7-ene-3,4-dicarboxylic acid tert-butyl ester, tricyclo[4.2.1.0$^{0,0}$]non-7-ene-3,4-dicarboxylic acid anhydride, N-butyl-tricyclo[4.2.1.0$^{0,0}$]non-7-ene-3,4-dicarboxyimide, 2-cyclopenten-1-one ethylene ketal, and vinylene carbonate.

In a preferred embodiment, the olefin monomers are present in the polymer at 50 mole % to 99.9 mole %, more preferably 70 to 98 mole %, more preferably 80 to 95 mole %. In a preferred embodiment, the polar monomers are present in the polymer at 0.1 mole % to 50 mole %, based upon the moles of all monomers present, more preferably 2 to 30 mole %, more preferably 5 to 20 mole %. In another preferred embodiment the polar monomer is present in the polymer at 0.2 to 15 mole % and the olefin monomer(s) is present at 99.8 to 85 mole %.

In a preferred embodiment, the polar monomers are present in the feed to the reactor at 0.1 mole % to 50 mole %, based on all monomers present in the feed, more preferably 2 to 30 mole %, more preferably 5 to 20 mole %. In a preferred embodiment, the olefin monomers are present in the feed to the reactor at 50 mole % to 99.9 mole %, more preferably 70 to 98 mole %, more preferably 80 to 95 mole %. In another preferred embodiment the polar monomer is present in the feed to the reactor at 0.2 to 15 mole % and the olefin monomer(s) is present at 99.8 to 85 mole %.

Preferred combinations of monomers include ethylene and one or more of: 7-octen-1-ol, 7-octen-1-ol trimethylsilyl ether, octenyl acetate, 5-norbornen-2-yl acetate, 5-norbornen-2-ol, and 5-norbornen-2-ol trimethylsilyl ether.

Preferred combinations of monomers include propylene and one or more of: 7-octen-1-ol, 7-octen-1-ol trimethylsilyl ether, octenyl acetate, 5-norbornen-2-yl acetate, 5-norbornen-2-ol, and 5-norbornen-2-ol trimethylsilyl ether.

For purposes of this disclosure, the term oligomer refers to compositions having 2-40 mer units and the term polymer refers to compositions having 41 or more mer units. A mer is defined as a unit of an oligomer or polymer that originally corresponded to the monomer(s) used in the oligomerization or polymerization reaction. For example, the mer of polyethylene would be ethylene. Oligomers and polymers may have one kind of mer unit or may have many different mer units. For example one may have an oligomer of ethylene alone or an oligomer of butene, ethylene and propylene.

In an embodiment herein, the process described herein is used to produce an oligomer of any of the olefin and polar monomers listed above. Preferred olefin monomers for use in oligomers include any $C_2$ to $C_{20}$ olefins, preferably $C_2$ to $C_{12}$ alpha-olefins, most preferably ethylene, propylene and or butene. Preferred polar monomers for use in oligomers include 7-octen-1-ol, 7-octen-1-ol trimethylsilyl ether, octenyl acetate, 5-norbornen-2-yl acetate, 5-norbornen-2-ol, and 5-norbornen-2-ol trimethylsilyl ether.

In a preferred embodiment the process described herein may be used to produce homopolymers or copolymers. (For the purposes of this invention and the claims thereto a copolymer may comprise two, three, four or more different monomer units.) Preferred polymers produced herein include copolymers of any of the above olefin monomers with any of the above polar monomers. In a preferred embodiment the process described herein may be used to produce a copolymer comprising ethylene and one or more of the polar monomers listed above. In another embodiment the process described herein may be used to produce a copolymer comprising propylene and one or more of the polar monomers listed above. In another embodiment the process described herein may be used to produce a copolymer comprising ethylene, propylene, and one or more of the polar monomers listed above.

In another preferred embodiment the polymer produced herein is a copolymer of ethylene and one or more polar monomers, preferably one or more linear alpha-vinyl, omega-polar monomers or cyclic polar monomers. Most preferably the polymer produced herein is a copolymer of ethylene and one or more of 7-octen-1-ol, 7-octen-1-ol trimethylsilyl ether, octenyl acetate, 5-norbornen-2-yl acetate, 5-norbornen-2-ol, and 5-norbornen-2-ol trimethylsilyl ether.

In another preferred embodiment the polymer produced herein is a copolymer of propylene and one or more polar monomers, preferably one or more linear alpha-vinyl, omega-polar monomers or cyclic polar monomers. Most preferably the polymer produced herein is a copolymer of propylene and one or more of 7-octen-1-ol, 7-octen-1-ol trimethylsilyl ether, octenyl acetate, 5-norbornen-2-yl acetate, 5-norbornen-2-ol, and 5-norbornen-2-ol trimethylsilyl ether.

In another preferred embodiment the polymer produced herein is a terpolymer of ethylene, propylene, and one or more polar monomers, preferably one or more linear alpha-vinyl, omega-polar monomers or cyclic polar monomers. Most preferably the polymer produced herein is a terpolymer of ethylene, propylene and one or more of 7-octen-1-ol, 7-octen-1-ol trimethylsilyl ether, octenyl acetate, 5-norbornen-2-yl acetate, 5-norbornen-2-ol, and 5-norbornen-2-ol trimethylsilyl ether.

In a preferred embodiment the polymers described herein further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more. Preferred dienes include butadiene, pentadiene, hexadiene, heptadiene, octadiene, nonadiene, decadiene, undecadiene, dodecadiene, and cyclopentadiene.

In a preferred embodiment the polar monomer comprises one or more of any alpha-vinyl, omega-polar monomers or cyclic polar monomers, including 7-octen-1-ol, 7-octen-1-ol trimethylsilyl ether, octenyl acetate, 5-norbornen-2-yl acetate, 5-norbornen-2-ol, and 5-norbornen-2-ol trimethylsilyl ether.

In another embodiment, the polymer produced herein comprises:
  a first olefin monomer present at from 40 to 95 mole %, preferably 50 to 90 mole %, more preferably 60 to 80 mole %, and
  a second olefin monomer present at from 5 to 60 mole %, preferably 10 to 40 mole %, more preferably 20 to 40 mole %,
  a third olefin monomer present at from 0 to 10 mole %, more preferably from 0.5 to 5 mole %, more preferably 1 to 3 mole %,
  a polar monomer present at from 0.001 to 50 mole %, preferably from 0.01 to 30 mole %, more preferably from 0.1 to 20 mole %, most preferably from 0.2 to 15 mole %.

In a preferred embodiment the first olefin monomer comprises one or more of any $C_3$ to $C_8$ linear, branched or cyclic alpha-olefins, including propylene, butene (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, and the like.

In a preferred embodiment the second olefin monomer comprises one or more of any $C_2$ to $C_{40}$ linear, branched or cyclic alpha-olefins, including ethylene, propylene, butene, pentene, hexene, heptene, octene, nonene, decene, undecene, dodecene, hexadecene, 3,5,5-trimethylhexene-1, 3-methylpentene-1,4-methylpentene-1,5-ethyl-1-nonene, cyclooctene, cyclopentene, and cyclohexene.

In a preferred embodiment the third olefin monomer comprises one or more of any $C_2$ to $C_{40}$ linear, branched or cyclic alpha-olefins, including 3,5,5-trimethylhexene-1,3-methylpentene-1,4-methylpentene-1,5-ethyl-1-nonene, cyclooctene, cyclopentene, and cyclohexene. In a preferred embodiment the third monomer comprises one or more dienes.

Oligomerization Processes

The catalyst compositions described above may be used to oligomerize or polymerize any unsaturated monomer, however they are preferably used to oligomerize olefins, typically alpha-olefins, with polar monomers. In the instant oligomerization processes, the process temperature may be −100° C. to 300° C., −20° C. to 200° C., or 0° C. to 150° C. Some embodiments select oligomerization pressures (gauge) from 0 kPa-35 MPa or 500 kPa-15 MPa. In a preferred embodiment, conditions that favor oligomer production include using aluminum alkyls (as activator or scavenger, etc.) and/or selecting a nickel catalyst compound where $Ar^1$ and or $Ar^2$ comprises phenyl and/or mesityl. A preferred feedstock for the oligomerization process is the alpha-olefin, ethylene, in combination with any alpha-vinyl, omega-polar monomer or cyclic polar monomer. But other alpha-olefins, including but not limited to propylene and 1-butene, may also be used in place of or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Preferred polar monomers include 7-octen-1-ol, 7-octen-1-ol trimethylsilyl ether, octenyl acetate, 5-norbornen-2-yl acetate, 5-norbornen-2-ol, and 5-norbornen-2-ol trimethylsilyl ether. Dienes may be used in the processes described herein, preferably alpha, omega-dienes are used alone or in combination with mono-alpha olefins.

Preferred oligomerization processes may be run in the presence of various liquids, particularly aprotic organic liquids. Preferably the homogeneous catalyst system, olefin monomers, polar monomers, and product are soluble in these liquids. A supported (heterogeneous) catalyst system may also be used, but will form a slurry rather than a solution. Suitable liquids for both homo- and heterogeneous catalyst systems, include alkanes, alkenes, cycloalkanes, selected halogenated hydrocarbons, aromatic hydrocarbons, and in some cases, hydrofluorocarbons. Useful solvents specifically include hexane, toluene, cyclohexane, benzene, and mixtures of toluene and diethyl ether.

Polymerization Processes

Typically one or more E-phenoxide compounds, one or more optional activators, one or more olefin monomers and one or more polar monomers are contacted to produce polymer. The components may be contacted in a solution, bulk, gas or slurry polymerization process or a combination thereof, preferably solution phase or bulk phase polymerization process.

In general the combined E-phenoxide compounds and the activator are combined in ratios of about 1:10,000 to about 1:1, in other embodiments the combined E-phenoxide compounds and the activator are combined in ratios of 1:1 to 100:1. When alumoxane or aluminum alkyl activators are used, the combined pre-catalyst-to-activator molar ratio is from 1:5000 to 10:1, alternatively from 1:1000 to 10:1; alternatively, 1:500 to 2:1; or 1:300 to 1:1. When ionizing activators are used, the combined pre-catalyst-to-activator molar ratio is from 10:1 to 1:10; 5:1 to 1:5; 2:1 to 1:2; or 1.2:1 to 1:1. Multiple activators may be used, including using mixtures of alumoxanes or aluminum alkyls with ionizing activators.

One or more reactors in series or in parallel may be used in the present invention. Catalyst component and activator may be delivered as a solution or slurry, either separately to the reactor, activated in-line just prior to the reactor, or preactivated and pumped as an activated solution or slurry to the reactor. A preferred operation is two solutions activated in-line. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-isobutyl aluminum and an excess of alumoxane or modified alumoxane.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg (0.001 bar) to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred. Alternately, mixtures of polar and nonpolar solvents can be used. For purposes of this invention, a nonpolar solvent is defined as a solvent that contains only carbon and hydrogen atoms (such as an alkene or arene), while a polar solvent is defined a solvent that contains at least one Group 15, 16, or 17 heteroatom (such as oxygen, fluorine, or chlorine). Particularly, a mixture of a nonpolar aliphatic or aromatic solvent with a polar solvent, particularly diethyl ether, is preferred. Preferred polar solvents include diethyl ether, methyl t-butyl ether, tetrahydrofuran, di-n-butyl ether, methyl propyl ether, di-n-propyl ether, diisopropyl ether, ethyl acetate, and acetone. Preferred non-polar solvents include toluene, hexane, pentane, isopentane, and octane. The process can be carried out in a continuous stirred tank reactor, batch reactor or plug flow reactor, or more than one reactor operated in series or parallel. These reactors may have or may not have internal cooling and the monomer feed my or may not be refrigerated. See the general disclosure of U.S. Pat. No. 5,001,205 for general process conditions. See also, international application WO 96/33227 and WO 97/22639 for more information. In a preferred embodiment, a mixture of toluene and diethyl ether is used as the diluent or solvent.

Polymers Produced

The polymers produced herein may have a weight average molecular weight (Mn) 1000 to 1,000,000, preferably from 1500 to 500,000. The polymers produced herein may have a molecular weight distribution (Mw/Mn) of up to 6, preferably from 1.1 to 4.5, more preferably from 1.1 to 3.5.

In a preferred embodiment, this invention relates to a copolymer comprising olefin monomer and from 0.2 to 30 mole %, preferably 0.2 to 15 mole % of a polar monomer where the copolymer has less than 25 total alkyl branches per 1000 carbons and the copolymer has 45% or more (alternately 50% or more, alternately 55% or more) of its olefinic end groups as vinyls.

Any of the polymers or oligomers produced by this invention, may be further functionalized after polymerization or oligomerization. Preferred functional groups for post-polymerization/oligomerization functionalization include maleic acid and maleic anhydride. By functionalized in this instance it is meant that the polymer has been contacted with an unsaturated acid or anhydride. Preferred unsaturated acids or anhydrides include any unsaturated organic compound containing at least one double bond and at least one carbonyl group. Representative acids include carboxylic acids, their anhydrides, their esters, and their salts, both metallic and non-metallic. Preferably the organic compound contains an ethylenic unsaturation conjugated with a carbonyl group (—C═O). Examples include maleic, fumaric, acrylic, methacrylic, itaconic, crotonic, alpha-methyl crotonic, and cinnamic acids as well as their anhydrides, esters and salt derivatives. Maleic anhydride is particularly preferred. The unsaturated acid or anhydride is preferably present at about 0.1 weight % to about 10 weight %, preferably at about 0.5 weight % to about 7 weight %, even more preferably at about 1 to about 4 weight %, based upon the weight of the hydrocarbon resin and the unsaturated acid or anhydride.

EXAMPLES

Catalysts

The precatalyst compounds used in the following examples are represented by the formulae below:

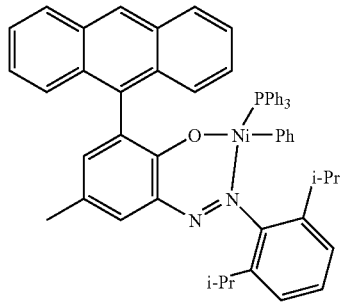

Azo-Phenoxide

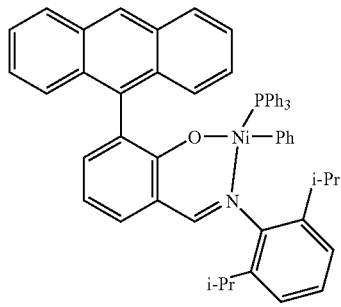

Imine-Phenoxide
(comparative)

Example 1

Preparation of [2-(2',6'-Diisopropylphenylazo)-4-methyl-6-(9-anthracenyl)phenoxide]-Nickel(phenyl)(triphenylphosphine) (Catalyst 1). Catalyst 1 was prepared as described in preceding application U.S. Ser. No. 10/436,741 (which is incorporated by reference herein), where it is referred to as catalyst C. This phenol was prepared from a theoretical yield of 3.9 mmol of diazotized 2,6-diisopropylaniline (prepared as reported (*Helvetica Chimica Acta* 1983, 66, 1737)) quenched with a phenolate solution comprised of 2-(9-anthracenyl)-4-methylphenol (0.63 g), water (20 mL), NaOH (20 mmol), pyridine (2 mL), and benzene (4 mL) cooled in an ice bath. The organic layer was collected and depleted of volatiles on a rotary evaporator. The crude ligand, 2-(2',6'-diisopropylphenylazo)-4-methyl-6-(9-anthracenyl)phenol, was purified by chromatography on silica gel using 10:1 hexanes/diethyl ether as an eluent, followed by crystallized from methanol (slow evaporation at ambient temperature). Yield was approximately 0.30 g (29%). $(PPh_3)_2$ Ni(Ph)(Br) (560 mg, 0.76 mmol) was added to a solution of potassium 2-(2',6'-diisopropylphenylazo)-4-methyl-6-(9-anthracenyl)phenoxide (0.56 mmol) in THF (45 mL) (prepared by addition of a slight excess of KH to the purified 2-(2',6'-diisopropylphenylazo)-4-methyl-6-(9-anthracenyl)phenol) causing a color change to red/brown. After 2 hours, the solvent and residual volatiles were removed and the residue was extracted with pentane (70 mL) and filtered to collect the crude insoluble product, which was dried in vacuo. Residual phosphine was removed by trituration with pentane overnight at −30° C. to give the product as the remaining pentane-insoluble dark red/brown powder. Yield was approximately 310 mg (64%). $^1$H NMR ($C_6D_6$): 1.27 (doublet of doublets; J=7, 18 Hz; 12H); 2.08 (singlet; 3H); 4.26 (septet; J=7 Hz; 2H); 6.29 (multiplet; 3H); 6.58 (triplet; J=8 Hz; 6H); 6.76 (triplet; J=8 Hz; 3H); 6.87-7.19 (multiplet; 16H); 7.63 (doublet; J=8 Hz; 2H); 7.81 (doublet; J=8 Hz; 2H); 7.86 (singlet; 1H); 7.94 (doublet; J=2 Hz; 1H) ppm. The 2-(9-anthracenyl)-4-methylphenol was prepared as follows: A 500 mL round bottom flask was charged with 9-bromoanthracene (20.7 g, 80.5 mmol, 1.1 equivalents) and $(PPh_3)_2NiCl_2$ (1.33 g, 2.0 mmol, 2.7% catalyst) in approximately 150 mL THF under a nitrogen atmosphere. While stirring at ambient temperature, a freshly prepared magnesium Grignard solution of tetrahydropyran (THP)-protected 2-bromo-cresol (2MgBr-CresolTHP)-(theoretical yield 75.0 mmol, 1 equivalent) in 150 mL THF was added over a 15 minute period with little change in the solution temperature. The reaction was heated at reflux for 5 days, slowly causing a change in color from brown to green. After cooling, the flask was moved to a fume hood and most of the solvent was evaporated via nitrogen flow. The reaction was diluted with 200 mL of hexanes, cooled in an ice bath, and any remaining Grignard or active magnesium compounds were quenched by slow addition of 50 mL water. Recovery of the organic layer and removal of volatiles by evaporation led to a yellow/brown oil that deposited some light yellow powder and crystals of product upon standing. More product was extracted from the oil by adding acetone and collecting the white crystalline material which formed. Removal of acetone in vacuo resulted in 7.8 g of phenol (37% yield). $^1$H NMR ($C_6D_6$, 250 MHz, 22° C.): δ 2.09 ppm, s, 3H; 4.13 ppm, s, 1H; 6.84 ppm, s, 1H; 7.05-7.23 ppm, m, 6H; 7.82 ppm, d, $J_{HH}$=9.3 Hz, 4H; 8.24 ppm, s, 1H.

Comparative Example C1

Preparation of [2-(2',6'-Diisopropylphenylimino)-6-(9-anthracenyl)phenoxide]-Nickel(phenyl)(triphenylphosphine) (Catalyst C1). Comparative catalyst C1 was prepared according to literature methods (WO 98/42664) and purified by reprecipitation from benzene into pentane (both solvents dried by distillation from sodium benzophenone ketyl), followed by three cycles of slurrying in diethyl ether (10 mL/400 mg catalyst; dried by passage through alumina) to remove soluble impurities. The resultant material contained approximately 1.5 mol % free $PPh_3$ (by $^{31}$P NMR in $CDCl_3$ vs. external 85% aqueous $H_3PO_4$ standard, δ 31.6 ppm; C1, δ 27.74 ppm) and some residual ether (by $^1$H NMR).

Monomers

In the below examples, $^{13}$C and $^1$H NMR spectra for monomers were obtained on a Bruker Avance 400 MHz Ultrashield spectrometer or a Varian UnityPlus 500 MHz spectrometer. Spectra were referenced to CDCl$_3$ ($^{13}$C, 77.00 ppm; $^1$H, 7.25 ppm); the following abbreviations are used: s=singlet, d=doublet, tr=triplet, q=quartet, m=multiplet. Infrared spectra were taken using a ThermoNicolet Nexus 470 FTIR running OMNIC software. Tandem gas chromatography/time-of-flight field ionization mass spectrometry (GC-TOF-MS) was conducted using a Hewlett-Packard 6890 GC and a MicroMass GCP spectrometer. Elemental analyses were conducted by QTI Inc., Whitehouse, N.J.

Ethylene (AGT grade 4.5, 99.995%) was used as received. 7-Octen-1-ol (TCI Co., 96%) was dried over 3 Å sieves for 3 days, filtered, and distilled at 50° C./2 mm (267 Pa). All other commercial comonomers were distilled from CaH$_2$ at the given temperature and pressure, degassed by freeze-pump-thaw cycles, and stored at −35° C. in a freezer under argon: 1-octene (Aldrich Co., 98%, 39° C./39 mm (5200 Pa)), octenyl acetate (TCI Co., 98+%, 54° C./10 mm (1333 Pa)), norbornene (Aldrich Co., 99%, 96° C./760 mm (101325 Pa)), 5-norbornen-2-yl acetate (Aldrich Co., 98%, 76° C./14 mm (1867 Pa); 79: 21 endo:exo by average of $^1$H and $^{13}$C NMR). The endo:exo ratio for 5-norbornen-2-yl acetate was determined by integration of the following resonances: $^1$H NMR, endo olefin (C$\underline{H}$ farthest from OAc) 6.16, exo olefin (C$\underline{H}$ farthest from OAc) 6.07, endo C$\underline{H}$OAc 5.10, exo C$\underline{H}$OAc 4.49 ppm; $^{13}$C NMR, endo olefin 138.01 and 131.15, exo olefin 140.61 and 132.24, endo methine (C$\underline{H}$ farthest from OAc) 41.82, exo methine (C$\underline{H}$ farthest from OAc) 40.22 ppm.

Example 2

Synthesis of 7-octen-1-ol trimethylsily ether. In a 3-necked, 1 L round-bottomed flask, 1-octenol (21.16 g, 165 mmol) and Et$_3$N (Aldrich Co., used as received, 23.0 mL, 165 mmol) were dissolved in 500 mL CH$_2$Cl$_2$ under an N$_2$ purge. A stirbar was added and the flask was fitted with a pressure-equalized addition funnel. In the drybox, a solution of Me$_3$SiCl (Aldrich Co., used as received, 18.82 g, 173 mmol) in 100 mL CH$_2$Cl$_2$ was prepared in a round-bottomed flask sealed with a rubber septum. This solution was cannulated into the addition funnel and added dropwise to the stirred 1-octenol solution. White smoke and a gentle reflux were observed and a white precipitate was observed. The mixture was stirred at room temperature overnight under N$_2$, cooled to 0° C., and depleted of volatiles using a Schlenk vacuum line with an in-line trap (caution: traps containing Me$_3$SiCl should be vented to an inert atmosphere). The resultant solid was purged with N$_2$ for 0.5 hour and taken into the drybox and extracted with 100 mL pentane. The cloudy supernatant was filtered using a glass frit and an 0.45μ Acrodisc filter to obtain a clear solution. The pentane was removed using a rotary evaporator to give 7-octen-1-OSiMe$_3$ as a colorless liquid (27.71 g, 83.8%) which was dried over CaH$_2$, distilled at 42° C./2 mm (267 Pa), degassed by freeze-pump-thaw cycles, and stored at −35° C. in a freezer under argon. $^1$H NMR (CDCl$_3$): δ 5.79 (d of d of tr, J$_{tr}$=6.7 Hz, J$_d$=10.3, 17.0 Hz, 1H, =C$\underline{H}$), 4.99 (d of d of tr, J$_{tr}$=1.7 Hz, J$_d$=1.9, 17.2 Hz, 1H, $\underline{H}_2$C=cis to chain), 4.91 (d of d of tr, J$_{tr}$=1.2 Hz, J$_d$=2.1, 10.2 Hz, 1H, $\underline{H}_2$C=trans to chain), 3.55 (tr, J=6.7 Hz, 2H, C$\underline{H}_2$OSi), 2.03 (apparent q, J=7.1 Hz, 2H), 1.51 (apparent tr, J=7.0 Hz, 2H), 1.37 (app tr, J=7.4 Hz, 2H), 1.30 (m, 4H) (CH$_2$), 0.09 (s, 9H, SiMe$_3$).

$^{13}$C NMR (CDCl$_3$): δ 139.06 (=$\underline{C}$H, 1C), 114.16 (H$_2\underline{C}$=, 1C), 62.65 ($\underline{C}$H$_2$OSi), 33.64, 32.68, 28.91, 28.89, 25.68 ($\underline{C}$H$_2$, each 1C), −0.49 (SiMe$_3$, 3C). IR (NaCl thin film): 3078 (w), 2955 (sh), 2931 (vs), 2858 (s), 2736 (w), 1641 (m), 1456 (w), 1438 (w), 1415 (w), 1387 (w), 1294 (sh), 1259 (sh), 1251 (vs), 1099 (vs), 1031 (sh), 993 (m), 930 (sh), 910 m), 873 (s), 841 (vs), 747 (m), 709 (w), 685 (w) cm$^{-1}$. High-resolution GC-TOF-MS: One peak; Calculated, 200.1596; Found: 200.1588. Elemental analysis calculated for C$_{11}$H$_{24}$OSi: C, 65.93; H, 12.07; O, 7.98; Si, 14.02. Found: C, 65.56; H, 11.99.

Polymerizations

In the below examples, polymerizations were carried out simultaneously in triplicate using three 3 oz. (70 mL) Fisher-Porter glass pressure bottles clamped side-by-side in a single large oil bath. The bottles were fitted with heads equipped with a 200 psig (1.38 MPa) pressure gauge, syringe port, vent valve, and 152 psig (1.05 MPa) safety valve. The bottles were fitted with screw-on cylindrical polycarbonate blast shields, in which ⅜" diameter holes were periodically drilled to allow for efficient heating oil flow. An ethylene manifold featuring three separate flexihoses attached to a single 500 cc pressure vessel tank (PVT) was used, with one regulator controlling pressure for all three vessels.

The general polymerization procedure used was as follows: In the drybox, a stock solution of 0.045 mmol catalyst (1 or C1) in 12 mL toluene (dried by passage through alumina and Q-5 copper catalyst as described in: Pangborn, A. B.; Giardello, M. A.; Grubbs, R. H.; Rosen, R. K.; Timmers, F. J. *Organometallics* 1996, 15, 1518) was prepared in a graduated cylinder and stirred. The solution was divided into three separate vials each containing exactly 4 mL. These aliquots were loaded into three dry, air-tight 5 mL syringes which were kept in the drybox until immediately before injection. Separately, 18 mmol of comonomer was weighed out and diluted to a 24 mL volume in a 25 mL graduated cylinder and stirred. An 8 mL portion of this solution was added to each of the three Fischer Porter tubes. Another 3 mL of toluene was added to each tube along with a stirbar (for ethylene homopolymerization experiments, 11 mL dry toluene was added to each pressure vessel along with a magnetic stirbar, rather than 3 mL toluene plus 8 mL of the toluene solution containing the comonomer). The tubes were sealed, taken out of the drybox, attached to an ethylene manifold, and heated to 50° C. in an oil bath with magnetic stirring. Three pressurization cycles of the bottles to 120 psig C$_2$H$_4$ (827 kPa) followed by venting were carried out to remove residual argon. Syringe injection of the 4 mL aliquots of catalyst solution was carried out for the three bottles (final conditions in each bottle: 0.015 mmol catalyst (1.0 mM), 6 mmol comonomer (0.4 M), 15 mL total volume). Immediate repressurization of the bottles to 120 psig C$_2$H$_4$ (827 kPa) was carried out. After four hours of reaction time, venting, quenching with 5 mL of 5% v/v HCl-acidified MeOH solution, and precipitation of the polymer into excess clean MeOH were performed. The polymer products were collected by filtration, washed with additional clean MeOH, dried in a vacuum oven overnight at 60° C., weighed, and analyzed. For copolymers prepared with 7-octen-1-ol trimethylsilyl ether monomer, all silyl ether units were completely hydrolized to alcohol units during the quench procedure to give polymers containing 7-octen-1-ol enchainments.

$^{13}$C and $^1$H NMR spectra for polymers were obtained on a Varian INOVA 300 MHz spectrometer using a 10 mm broadband probe, a JEOL Delta 400 spectrometer using a 10 mm broadband probe, or a Varian UnityPlus 500 spectrometer using a 5 mm switchable probe, at 120° C. in 1,1,2,2-tetrachloroethane-$d_2$ or 1,2-dichlorobenzene-$d_4$ at 120° C. Cr(acac)$_3$ (15 mg/mL) was used as a relaxation agent for $^{13}$C spectra. 10,000-20,000 co-added transients were collected for $^{13}$C spectra and 160 for $^1$H NMR spectra. All alkyl branching and endgroup numbers were quantified versus the total aliphatic integral in the $^1$H and $^{13}$C spectra (includes acetate O$_2$CMe but not C=O, CHOR, CHOH, or CH$_2$OH peaks). Spectra were typically referenced to tetramethysilane (TMS), residual protio solvent peaks, or major polymer resonances insensitive to composition (e.g. $^{13}$C NMR main chain unbranched methylene run CH$_2$, 29.98 ppm). "Total alkyl branches" were quantified by $^1$H NMR using the branch end CH$_3$ peak (1.0-0.6 ppm) and by $^{13}$C NMR summing all of the individual branch types (C$_1$ by CH$_3$ at 21-18 ppm or by the two methylenes adjacent to the branch point, 39-37 ppm; C$_2$ by CH$_3$ at 13-9 ppm; C$_3$ by CH$_3$ at 14.5 ppm; C$_4^+$ by CH$_3$ at 14-13 ppm). In the $^1$H spectra, a second set of peaks slightly downfield of 1.0 ppm, potentially corresponding to methyls near branch points, was not included for purposes of calculating "total alkyl branches." These resonances were insignificant for polymers containing octene-based monomers but more prevalent for those incorporating norbornene-based monomers (for the latter, inclusion of these peaks would serve to raise "total alkyl branches" to ca. 60-70/1000 carbons). For olefins and alkyl branches, "per 1000 carbons" designates olefinic, aliphatic, and acetate O$_2$CMe carbons only, and is equal to (1000) (14.027)/($^1$H NMR M$_n$).

Olefins were quantified via the $^1$H NMR resonances for vinyls (5.9-5.65 ppm and 5.3-4.85 ppm), 1,2-disubstituted olefins (5.5-5.3 ppm), trisubstituted olefins (5.3-4.85 ppm, by difference from vinyls), and vinylidenes (4.85-4.55 ppm). Discrepancies between the two vinyl regions (suggesting cyclic endgroups) and shifts in unassigned regions were observed for the ethylene/norbornene copolymers; vinyl content was determined from the =CH$_2$ peak (4.9 ppm) and, after correction for vinyls, the balance of the 5.9-5.65 ppm area was assigned to cyclic 1,2-disubstituted structures. Non-cyclic 1,2-disubstituted olefins were determined from the peak at 5.5-5.3 ppm, and a peak at 5.2 ppm was assigned as trisubstituted olefins. For ethylene/5-norbornen-2-yl acetate copolymers, the vinylidene resonance partially overlapped the exo OCH and was assumed to be zero. Vinyls, which were partially overlapped in the upfield band by the endo OCH, were determined by the band at 5.9-5.65, and the appropriate area was then subtracted from the endo OCH resonance.

Number-average molecular weight (M$_n$) values calculated by $^1$H and $^{13}$C NMR were calculated using the olefin and aliphatic resonances ($^{13}$C NMR: 114-140 ppm), assuming each carbon is a CH$_2$ (14.027 g/mol) unit and assuming one olefinic endgroup per chain. These values do not include contributions from groups outside of the aliphatic region (C=O, OCH, OCH$_2$), In most cases, signal-to-noise ratios were not sufficient to allow for a $^{13}$C NMR M$_n$ calculation. Olefin distribution and M$_n$ values for ethylene/norbornene copolymers were unavailable due to discrepancies between the two vinyl regions (suggesting cyclic endgroups) and shifts in unassigned regions.

For purposes of copolymer compositional analysis, 1-octene content was determined using a $^{13}$C NMR by-difference method, in which the ratio of C$_4^+$ branch integral to the sum of the C$_1$, C$_2$, and C$_3$ branch integrals was calculated for the analogous homopolyethylene control samples. This ratio (typically near 0.25) was multiplied by the C$_1$, C$_2$, and C$_3$ branch integral for the 1-octene copolymer set, and the resultant value was subtracted from the C$_4^+$ branch integral for the 1-octene copolymer set. The remainder of the C$_4$+branch integral was then assigned to 1-octene. Octenyl acetate content was determined by averaging values obtained via $^1$H NMR, using the OCH$_2$ resonance at 4.1 ppm, and $^{13}$C NMR, using the OCH$_2$ resonance at 64.4 ppm and the C=O resonance at 170.2 ppm. 7-Octen-1-ol (and 7-octen-1-ol trimethylsilyl ether) content was similarly determined, using the $^1$H NMR OCH$_2$ resonance at 3.6 ppm, and the $^{13}$C NMR OCH$_2$ resonance at 63.4 ppm. Norbornene content was determined by averaging values obtained via $^1$H NMR, using the CH resonances at 2.1-2.0 ppm, and $^{13}$C NMR, using the backbone-enchained norbornene methine resonances (2 carbons at 47-48 ppm) and the norbornene bridgehead methines (2 carbons at 41.5-42.0 ppm). 5-Norbornen-2-yl acetate content was similarly determined, using the $^1$H NMR OCH resonances at 4.9 (endo) and 4.65 (exo) ppm, and the $^{13}$C NMR OCH resonances (78.1 ppm, exo; 75.8 ppm, endo) and C=O resonances (169.8 ppm, endo; 169.4 ppm, exo). For calculated values of comonomer units per 1000 carbons, "per 1000 carbons" designates aliphatic and acetate O$_2$CMe carbons only, and is equal to (1000)(mol fraction comonomer)/[(mol fraction comonomer)(#C comonomer)+(mol fraction C$_2$H$_4$)(2)] where "#C comonomer" equals 8 for 1-octene and octenyl acetate, and 7 for norbornene, 5-norbornen-2-yl acetate, 7-octen-1-ol, and 7-octen-1-ol trimethylsilyl ether.

Number-average molecular weight (M$_n$), weight-average molecular weight (M$_w$), and polydispersity index (PDI, M$_w$/M$_n$) values were measured using a Waters Associates 150 C high temperature gel permeation chromatograph equipped with three Polymer Laboratories mixed bed Type B columns (10µ PD, 7.8 mm inner diameter, 300 mm length) in BHT (2,6-di-tert-butyl-4-methylphenol)-inhibited 1,2,4-trichlorobenzene at 135° C. using an internal differential refractive index detector (1.0 mL/minute flow rate; typical sample concentration 2 mg/mL; 300 µL injection loop). Values are reported versus polyethylene standards.

In the below examples, the following abbreviations and assumptions are used in the Tables: "Total Br" is the total alkyl branches per 1000 carbons (/K) determined by summing methyls observed for all branch types. "C$_1$, C$_2$, C$_3$, and C$_4^+$" are the methyl, ethyl, propyl, and butyl and higher branches per 1000 carbons. "Vinyl, 1,2-Disub., Trisub., and V-dene" are the percentages of olefin endgroups present as vinyl, 1,2-disubstituted olefin (vinylene), trisubstituted olefin, and vinylidene (1,1-disubstituted) structures. "NMR M$_n$" is molecular weight calculated assuming that all polymers have one olefinic endgroup.

Example 3

Copolymerization of ethylene and octenyl acetate using 1. The results in Tables 1 and 1A were obtained.

TABLE 1

| Ex. No. | Yield (g) | Activity (g/ mmol cat) | Activity (g/ mmol cat hr) | M$_w$ | M$_n$ | M$_w$/M$_n$ |
|---|---|---|---|---|---|---|
| 3-1 | 0.65 | 43.33 | 10.83 | 13,590 | 4,170 | 3.26 |
| 3-2 | 0.65 | 43.33 | 10.83 | 11,940 | 3,800 | 3.14 |
| 3-3 | 0.66 | 44.00 | 11.00 | 13,100 | 3,890 | 3.37 |
| Average | 0.65 | 43.56 | 10.89 | 12,880 | 3,950 | 3.26 |

TABLE 1A

| Ex. No. | $^1$H mol % comon. | $^{13}$C mol % comon. | Avg. mol % comon. | $^1$H Total Br/K | $^{13}$C Total Br/K | Avg. Total Br/K | % Vinyl | % 1,2-Disub. | % Trisub. | % V-dene | $C_1$/K | $C_2$/K | $C_3$/K | $C_4^+$/K | $^1$H NMR $M_n$ |
|---|---|---|---|---|---|---|---|---|---|---|---|---|---|---|---|
| 3-1 | 0.7 | 0.6 | 0.7 | 18.1 | 15.4 | 16.8 | 47.4 | 44.7 | 7.8 | 0 | 10.8 | 0.9 | 0.2 | 3.5 | 4356 |
| 3-2 | 0.7 | 0.6 | 0.7 | 18.7 | 22.4 | 20.6 | 51.0 | 45.5 | 3.5 | 0 | 12.9 | 3.5 | 0.6 | 5.3 | 4210 |
| 3-3 | 0.7 | 0.7 | 0.7 | 18.3 | 18.4 | 18.4 | 51.2 | 45.8 | 3.0 | 0 | 12.6 | 1.2 | 0.3 | 4.3 | 4319 |
| Average | 0.7 | 0.6 | 0.7 | 18.4 | 18.7 | 18.6 | 49.9 | 45.3 | 4.8 | 0 | 12.1 | 1.9 | 0.4 | 4.4 | 4295 |

Comparative Example C2

Copolymerization of ethylene and octenyl acetate using C1. The results in Tables 2 and 2A were obtained.

TABLE 2

| Ex. No. | Yield (g) | Activity (g/mmol cat) | Activity (g/mmol cat hr) | $M_w$ | $M_n$ | $M_w/M_n$ |
|---|---|---|---|---|---|---|
| C2-1 | 0.509 | 33.93 | 8.48 | 15,840 | 7,390 | 2.14 |
| C2-2 | 0.462 | 30.80 | 7.70 | 14,320 | 6,150 | 2.33 |
| C2-3 | 0.420 | 28.00 | 7.00 | 15,480 | 7,160 | 2.16 |
| Average | 0.464 | 30.91 | 7.73 | 15,210 | 6,900 | 2.21 |

TABLE 2A

| Ex. No. | $^1$H mol % comon* | $^{13}$C mol % comon. | Avg. mol % comon. | $^1$H Total Br/K | $^{13}$C Total Br/K | Avg. Total Br/K | % Vinyl | % 1,2-Disub. | % Trisub. | % V-dene | $C_1$/K | $C_2$/K | $C_3$/K | $C_4^+$/K | $^1$H NMR $M_n$ |
|---|---|---|---|---|---|---|---|---|---|---|---|---|---|---|---|
| C2-1 | 0.9 | 1.0 | 1.0 | 21.5 | 24.3 | 22.9 | 29.4 | 70.6 | 0.0 | 0 | 15.2 | 4.8 | 1.0 | 3.3 | 10318 |
| C2-2 | 0.9 | 1.1 | 1.0 | 22.7 | 25.1 | 23.9 | 29.1 | 70.9 | 0.0 | 0 | 18.5 | 2.5 | 0.6 | 3.4 | 9331 |
| C2-3 | 0.9 | 0.9 | 0.9 | 22.6 | 21.9 | 22.3 | 25.1 | 66.3 | 8.6 | 0 | 16.1 | 1.9 | 0.8 | 3.2 | 9362 |
| Average | 0.9 | 1.0 | 1.0 | 22.3 | 23.8 | 23.0 | 27.9 | 69.3 | 2.9 | 0 | 16.6 | 3.1 | 0.8 | 3.3 | 9670 |

*Traces (<0.05%) of octenol and unidentified peaks near 0 ppm detected.

Example 4

Copolymerization of ethylene and 7-octen-1-ol using 1. The results in Tables 3 and 3A were obtained.

TABLE 3

| Ex. No. | Yield (g) | Activity (g/mmol cat) | Activity (g/mmol cat hr) | $M_w$ | $M_n$ | $M_w/M_n$ |
|---|---|---|---|---|---|---|
| 4-1 | 0.05 | 3.33 | 0.83 | 6,610 | 2,650 | 2.49 |
| 4-2 | 0.05 | 3.33 | 0.83 | 6,870 | 2,680 | 2.56 |
| 4-3 | 0.06 | 4.00 | 1.00 | 6,340 | 2,550 | 2.49 |
| Average | 0.05 | 3.56 | 0.89 | 6,610 | 2,630 | 2.51 |

TABLE 3A

| Ex. No. | $^1$H mol % comon. | $^{13}$C mol % comon. | Avg. mol % comon. | $^1$H Total Br/K | $^{13}$C Total Br/K | Avg. Total Br/K | % Vinyl | % 1,2-Disub. | % Trisub. | % V-dene | $C_1$/K | $C_2$/K | $C_3$/K | $C_4^+$/K | $^1$H NMR $M_n$ |
|---|---|---|---|---|---|---|---|---|---|---|---|---|---|---|---|
| 4-1 | 0.7 | 0.7 | 0.7 | 22.5 | 17.5 | 20.0 | 52.3 | 42.0 | 5.7 | 0 | 11.1 | 2.2 | 0.0 | 4.1 | 3240 |
| 4-2 | 0.7 | NA | 0.7 | 23.0 | NA | 23.0 | 54.6 | 42.7 | 2.8 | 0 | NA | NA | NA | NA | 3378 |
| 4-3 | 0.7 | 0.8 | 0.8 | 23.5 | 19.4 | 21.5 | 57.4 | 43.6 | 0.0 | 0 | 14.3 | 0.0 | 0.0 | 5.1 | 3381 |
| Average | 0.7 | 0.8 | 0.7 | 23.0 | 18.5 | 21.5 | 54.8 | 42.8 | 2.8 | 0 | 12.7 | 1.1 | 0.0 | 4.6 | 3333 |

NA = Insufficient material tor analysis.

Comparative Example C3

Copolymerization of ethylene and 7-octen-1-ol using C1. The results in Tables 4 and 4A were obtained.

TABLE 4

| Ex. No. | Yield (g) | Activity (g/mmol cat) | Activity (g/mmol cat hr) | $M_w$ | $M_n$ | $M_w/M_n$ |
|---|---|---|---|---|---|---|
| C3-1 | 0.019 | 1.27 | 0.32 | 6,740 | 3,440 | 1.96 |
| C3-2 | 0.006 | 0.40 | 0.10 | 5,500 | 2,740 | 2.01 |
| C3-3 | 0.014 | 0.93 | 0.23 | 7,510 | 3,720 | 2.02 |
| Average | 0.013 | 0.87 | 0.22 | 6,583 | 3,300 | 2.00 |

TABLE 4A

| Ex. No. | $^1$H mol % comon. | $^1$H Total Br/K | % Vinyl | % 1,2-Disub. | % Trisub. | % V-dene | $^1$H NMR $M_n$ |
|---|---|---|---|---|---|---|---|
| C3-1 | 0.9 | 24.0 | 33.5 | 49.1 | 17.4 | 0 | 9203 |
| C3-2 | NA | NA | NA | NA | NA | NA | NA |
| C3-3 | 0.8 | 24.1 | 39.7 | 60.3 | 0 | 0 | 10422 |
| Average | 0.9 | 24.1 | 36.6 | 54.7 | 8.7 | 0 | 9813 |

NA = Insufficient material for analysis (no $^{13}$C NMR data available due to insufficient material)

Example 5

Copolymerization of ethylene and 7-octen-1-ol trimethylsilyl ether using 1. The results in Tables 5 and 5A were obtained.

TABLE 5

| Ex. No. | Yield (g) | Activity (g/mmol cat) | Activity (g/mmol cat hr) | $M_w$ | $M_n$ | $M_w/M_n$ |
|---|---|---|---|---|---|---|
| 5-1 | 0.74 | 49.33 | 12.33 | 12,030 | 3,870 | 3.11 |
| 5-2 | 0.68 | 45.33 | 11.33 | 10,120 | 3,610 | 2.80 |
| 5-3 | 0.68 | 45.33 | 11.33 | 11,570 | 3,780 | 3.06 |
| Average | 0.70 | 46.67 | 11.67 | 11,240 | 3,750 | 2.99 |

TABLE 5A

| Ex. No. | $^1$H mol % comon.* | $^{13}$C mol % comon.* | Avg. mol % comon.* | $^1$H Total Br/K | $^{13}$C Total Br/K | Avg. Total Br/K | % Vinyl | % 1,2-Disub. | % Trisub. | % V-dene | $C_1$/K | $C_2$/K | $C_3$/K | $C_4^+$/K | $^1$H NMR $M_n$ |
|---|---|---|---|---|---|---|---|---|---|---|---|---|---|---|---|
| 5-1 | 0.7 | 0.6 | 0.7 | 19.5 | 16.7 | 18.1 | 51.9 | 46.4 | 1.7 | 0 | 11.3 | 0.9 | 0.5 | 4.1 | 4257 |
| 5-2 | 0.8 | 0.7 | 0.8 | 20.3 | 16.0 | 18.2 | 49.3 | 44.8 | 5.8 | 0 | 10.9 | 0.5 | 0.2 | 4.4 | 3880 |
| 5-3 | 0.7 | 0.6 | 0.7 | 19.9 | 17.4 | 18.7 | 49.3 | 44.7 | 6.0 | 0 | 11.1 | 1.0 | 0.5 | 4.7 | 3963 |
| Average | 0.7 | 0.6 | 0.7 | 19.9 | 16.7 | 18.3 | 50.2 | 45.3 | 4.5 | 0 | 11.1 | 0.8 | 0.4 | 4.4 | 4033 |

*As 7-octen-1-ol.

Comparative Example C4

Copolymerization of ethylene and 7-octen-1-ol trimethylsilyl ether using C1. The results in Tables 6 and 6A were obtained.

TABLE 6

| Ex. No. | Yield (g) | Activity (g/mmol cat) | Activity (g/mmol cat hr) | $M_w$ | $M_n$ | $M_w/M_n$ |
|---|---|---|---|---|---|---|
| C4-1 | 0.69 | 46.00 | 11.50 | 17,790 | 8,030 | 2.22 |
| C4-2 | 0.67 | 44.67 | 11.17 | 18,900 | 8,470 | 2.23 |
| C4-3 | 0.66 | 44.00 | 11.00 | 18,930 | 8,280 | 2.29 |
| Average | 0.67 | 44.89 | 11.22 | 18,540 | 8,260 | 2.24 |

TABLE 6A

| Ex. No. | $^1$H mol % comon* | $^{13}$C mol % comon* | Avg. mol % comon* | $^1$H Total Br/K | $^{13}$C Total Br/K | Avg. Total Br/K | % Vinyl | % 1,2-Disub. | % Trisub. | % V-dene | $C_1$/K | $C_2$/K | $C_3$/K | $C_4^+$/K | $^1$H NMR $M_n$ |
|---|---|---|---|---|---|---|---|---|---|---|---|---|---|---|---|
| C4-1 | 0.8 | 0.7 | 0.8 | 21.4 | 19.5 | 20.5 | 22.2 | 63.3 | 14.4 | 0 | 15.5 | 1.2 | 0.5 | 2.4 | 8108 |
| C4-2 | 0.8 | 0.7 | 0.8 | 21.0 | 18.1 | 19.6 | 29.8 | 66.5 | 3.7 | 0 | 15.2 | 1.3 | 0.3 | 1.3 | 9041 |
| C4-3 | 0.8 | 0.6 | 0.7 | 20.3 | 18.2 | 19.3 | 28.0 | 68.2 | 3.8 | 0 | 15.5 | 0.7 | 0.3 | 1.7 | 9275 |
| Average | 0.8 | 0.7 | 0.7 | 20.9 | 18.6 | 19.8 | 26.7 | 66.0 | 7.3 | 0 | 15.4 | 1.1 | 0.4 | 1.8 | 8808 |

*A 7-octen-1-ol. Traces of Si species near 0 ppm detected

Comparative Example C5

Copolymerization of ethylene and 1-octene using 1. Copolymerization with 1-octene was carried out to gauge the effects of omega-polar substituents (acetate, alcohol, trimethylsilyl ether) with 1. The results in Tables 7 and 7A were obtained.

TABLE 7

| Ex. No. | Yield (g) | Activity (g/mmol cat) | Activity (g/mmol cat hr) | $M_w$ | $M_n$ | $M_w/M_n$ |
|---|---|---|---|---|---|---|
| C5-1 | 2.05 | 136.67 | 34.17 | 11,390 | 3,610 | 3.16 |
| C5-2 | 1.98 | 132.00 | 33.00 | 11,720 | 3,790 | 3.09 |
| C5-3 | 1.98 | 132.00 | 33.00 | 12,830 | 3,700 | 3.47 |
| Average | 2.00 | 133.56 | 33.39 | 11,980 | 3,700 | 3.24 |

TABLE 7A

| Ex. No. | $^1$H mol % comon. | $^{13}$C mol % comon. | Avg. mol % comon. | $^1$H Total Br/K | $^{13}$C Total Br/K | Avg. Total Br/K | % Vinyl | % 1,2-Disub. | % Trisub. | % V-dene | $C_1$/K | $C_2$/K | $C_3$/K | $C_4^+$/K | $^1$H NMR $M_n$ |
|---|---|---|---|---|---|---|---|---|---|---|---|---|---|---|---|
| C5-1 | NA | 0.3 | NA | 25.6 | 19.5 | 22.6 | 44.2 | 50.1 | 5.7 | 0 | 11.6 | 1.2 | 0.3 | 6.4 | 3776 |
| C5-2 | NA | 0.5 | NA | 23.7 | 20.7 | 22.2 | 42.9 | 51.2 | 5.9 | 0 | 11.2 | 1.7 | 0.3 | 7.5 | 4304 |
| C5-3 | NA | 0.6 | NA | 24.3 | 25.1 | 24.7 | 46.2 | 51.5 | 2.2 | 0 | 13.0 | 2.4 | 0.6 | 9.1 | 4082 |
| Average | NA | 0.5 | NA | 24.5 | 21.8 | 23.2 | 44.4 | 50.9 | 4.6 | 0 | 11.9 | 1.8 | 0.4 | 7.7 | 4054 |

Comparative Example C6

Copolymerization of ethylene and 1-octene using C1. Copolymerization with 1-octene was carried out to gauge the effects of omega-polar substituents (acetate, alcohol, trimethylsilyl ether) with C1. The results in Tables 8 and 8A were obtained.

TABLE 8

| Ex. No. | Yield (g) | Activity (g/mmol cat) | Activity (g/mmol cat hr) | $M_w$ | $M_n$ | $M_w/M_n$ | Notes |
|---|---|---|---|---|---|---|---|
| C6-1 | 2.42 | 161.33 | 40.33 | 9,020 | 2,590 | 3.48 | sl. bimodal MWD |
| C6-2 | 2.94 | 196.00 | 49.00 | 15,500 | 3,160 | 4.91 | bimodal MWD |
| C6-3 | 2.64 | 176.00 | 44.00 | 15,280 | 2,880 | 5.31 | bimodal MWD |
| Average | 2.67 | 177.78 | 44.44 | 13,270 | 2,880 | 4.56 | |

TABLE 8A

| Ex. No. | $^1H$ mol % comon. | $^{13}C$ mol % comon. | Avg. mol % comon. | $^1H$ Total Br/K | $^{13}C$ Total Br/K | Avg. Total Br/K | % Vinyl | % 1,2-Disub. | % Trisub. | % V-dene | $C_1/K$ | $C_2/K$ | $C_3/K$ | $C_4^+/K$ | $^1H$ NMR $M_n$ |
|---|---|---|---|---|---|---|---|---|---|---|---|---|---|---|---|
| C6-1 | NA | 1.2 | NA | 51.4 | 51.3 | 51.4 | 13.4 | 80.4 | 6.1 | 0 | 25.9 | 7.9 | 2.0 | 15.6 | 3122 |
| C6-2 | NA | 0.8 | NA | 44.1 | 45.8 | 45.0 | 13.5 | 80.8 | 5.7 | 0 | 23.5 | 7.3 | 1.9 | 13.1 | 3916 |
| C6-3 | NA | 1.1 | NA | 48.1 | 50.1 | 49.1 | 11.6 | 81.7 | 6.7 | 0 | 26.3 | 6.9 | 1.9 | 15.0 | 3669 |
| Average | NA | 1.0 | NA | 47.9 | 49.1 | 48.5 | 12.8 | 81.0 | 6.2 | 0 | 25.2 | 7.4 | 1.9 | 14.6 | 3569 |

Example 6

Copolymerization of ethylene and 5-norbornen-2-yl acetate using 1. The results in Tables 9 and 9A were obtained.

TABLE 9

| Ex. No. | Yield (g) | Activity (g/mmol cat) | Activity (g/mmol cat hr) | $M_w$ | $M_n$ | $M_w/M_n$ | $^1H$ endo | $^1H$ exo | endo:exo |
|---|---|---|---|---|---|---|---|---|---|
| 6-1 | 0.060 | 4.00 | 1.00 | 7,240 | 3,720 | 1.95 | 4.6 | 1.4 | 77:23 |
| 6-2 | 0.055 | 3.67 | 0.92 | 6,850 | 3,680 | 1.86 | 5.5 | 1.4 | 80:20 |
| 6-3 | 0.050 | 3.33 | 0.83 | 6,800 | 3,750 | 1.81 | 5.7 | 1.4 | 80:20 |
| Average | 0.055 | 3.67 | 0.92 | 6,960 | 3,720 | 1.87 | 5.3 | 1.4 | 79:21 |

$^{13}C$ NMR analyses unavailable due to insufficient material.

TABLE 9A

| Ex. No. | $^1H$ mol % comon. | $^1H$ Total Br/K | % Vinyl | % 1,2-Disub. | % Trisub. | % V-dene | $^1H$ NMR $M_n$ |
|---|---|---|---|---|---|---|---|
| 6-1 | 5.9 | 14.5 | 58.6 | 41.4 | 0 | 0 | 4420 |
| 6-2 | 6.9 | 16.2 | 59.4 | 40.6 | 0 | 0 | 4619 |
| 6-3 | 7.2 | 14.7 | 59.0 | 41.0 | 0 | 0 | 4317 |
| Average | 6.7 | 15.1 | 59.0 | 41.0 | 0 | 0 | 4452 |

$^{13}C$ NMR analyses were unavailable due to insufficient material.

Comparative Example C7

Copolymerization of ethylene and 5-norbornen-2-yl acetate using C1. The results in Tables 10 and 10A were obtained.

TABLE 10

| Ex. No. | Yield (g) | Activity (g/mmol cat) | Activity (g/mmol cat hr) | $M_w$ | $M_n$ | $M_w/M_n$ | $^1H$ endo | $^{13}C$ endo | Avg endo | $^1H$ exo | $^{13}C$ exo | Avg endo | endo:exo |
|---|---|---|---|---|---|---|---|---|---|---|---|---|---|
| C7-1 | 0.110 | 7.33 | 1.83 | 17,500 | 10,520 | 1.66 | 4.8 | 4.5 | 4.7 | 1.4 | 1.4 | 1.4 | 77:23 |
| C7-2 | 0.087 | 5.80 | 1.45 | 13,530 | 6,920 | 1.96 | 5.3 | 5.8 | 5.6 | 1.6 | 1.7 | 1.7 | 77:23 |
| C7-3 | 0.104 | 6.93 | 1.73 | 15,130 | 7,800 | 1.94 | 5.5 | 5.4 | 5.5 | 1.7 | 1.7 | 1.7 | 76:24 |
| Average | 0.100 | 6.69 | 1.67 | 15,390 | 8,410 | 1.85 | 5.2 | 5.2 | 5.2 | 1.6 | 1.6 | 1.6 | 77:23 |

TABLE 10A

| Ex. No. | $^1H$ mol % comon. | $^{13}C$ mol % comon. | Avg. mol % comon. | $^1H$ Total Br/K | $^{13}C$ Total Br/K | Avg. Total Br/K | % Vinyl | % 1,2-Disub. | % Trisub. | % V-dene | $C_1/K$ | $C_2/K$ | $C_3/K$ | $C_4^+/K$ | $^1H$ NMR $M_n$ |
|---|---|---|---|---|---|---|---|---|---|---|---|---|---|---|---|
| C7-1 | 6.2 | 5.9 | 6.1 | 14.5 | 11.3 | 12.9 | 30.3 | 69.7 | 0 | 0 | See Total Me | not seen | not seen | not seen | 13126 |
| C7-2 | 7.0 | 7.5 | 7.3 | 17.7 | 10.0 | 13.9 | 27.0 | 73.0 | 0 | 0 | | | | | 9482 |
| C7-3 | 7.2 | 7.1 | 7.2 | 17.1 | 9.5 | 13.3 | 29.4 | 70.6 | 0 | 0 | | | | | 9629 |
| Average | 6.8 | 6.8 | 6.8 | 16.4 | 10.3 | 13.4 | 28.9 | 71.1 | 0 | 0 | | | | | 10746 |

Comparative Example C8

Copolymerization of ethylene and norbornene using 1. Copolymerization with norbornene was carried out to gauge the effects of the cyclic-sited acetate substituent on 1. The results in Tables 11 and 11A were obtained.

TABLE 11

| Ex. No. | Yield (g) | Activity (g/mmol cat) | Activity (g/mmol cat hr) | $M_w$ | $M_n$ | $M_w/M_n$ |
|---|---|---|---|---|---|---|
| C8-1 | 0.40 | 26.67 | 6.67 | 9,120 | 3,980 | 2.29 |
| C8-2 | 0.35 | 23.33 | 5.83 | 9,400 | 4,450 | 2.11 |
| C8-3 | 0.36 | 24.00 | 6.00 | 8,080 | 3,590 | 2.25 |
| Average | 0.37 | 24.67 | 6.17 | 8,870 | 4,010 | 2.22 |

TABLE 11A

| Ex. No. | $^1$H mol % comon. | $^{13}$C mol % comon. | Avg. mol % comon. | $^1$H Total Br/K* | $^{13}$C Total Br/K^ | Avg. Total Br/K |
|---|---|---|---|---|---|---|
| C8-1 | 15.2 | 12.8 | 14.0 | 25.0 | 9.5 | 17.3 |
| C8-2 | 14.9 | 13.2 | 14.1 | 26.0 | 9.8 | 17.9 |
| C8-3 | 13.9 | 12.6 | 13.3 | 25.9 | 9.7 | 17.8 |
| Average | 14.7 | 12.9 | 13.8 | 25.6 | 9.7 | 17.7 |

*Analysis complicated by cyclic olefinic endgroups.
^$^{13}$C by $S_{\alpha\delta+}$ CH$_2$ adjacent to branch (37.1 ppm): C8-1, 12; C8-2, 12; C8-3, 13.

| Ex. No. | % Vinyl* | % 1,2-Disub* | % Trisub* | % V-dene* | $C_1$/K | $C_2$/K | $C_3$/K | $C_4^+$/K | $^1$H NMR $M_n$* |
|---|---|---|---|---|---|---|---|---|---|
| C8-1 | 37.2 | 37.4 | 23.9 | 1.5 | 6.1 | 0.8 | 0.2 | 2.5 | 3024 |
| C8-2 | 38.9 | 35.4 | 25.7 | 0 | 6.4 | 0.0 | 0.4 | 3.0 | 3408 |
| C8-3 | 31.8 | 32.2 | 36.0 | 0 | 6.9 | 0.0 | 0.2 | 2.5 | 2781 |
| Average | 36.0 | 35.0 | 28.5 | 0.5 | 6.5 | 0.3 | 0.3 | 2.7 | 3071 |

*Analysis complicated by cyclic olefinic endgroups.
1,2-Disub. includes some cyclics.

Comparative Example C9

Copolymerization of ethylene and norbornene using C1. Copolymerization with norbornene was carried out to gauge the effects of the cyclic-sited acetate substituent on C1. The results in Tables 12 and 12A were obtained.

TABLE 12

| Ex. No. | Yield (g) | Activity (g/mmol cat) | Activity (g/mmol cat hr) | $M_w$ | $M_n$ | $M_w/M_n$ |
|---|---|---|---|---|---|---|
| C9-1 | 0.477 | 31.80 | 7.95 | 25,510 | 13,930 | 1.83 |
| C9-2 | 1.000 | 66.67 | 16.67 | 21,120 | 11,010 | 1.92 |
| C9-3 | 0.616 | 41.07 | 10.27 | 23,440 | 12,330 | 1.90 |
| Average | 0.698 | 46.51 | 11.63 | 23,360 | 12,420 | 1.88 |

TABLE 12A

| Ex. No. | $^1$H mol % comon. | $^{13}$C mol % comon. | Avg. mol % comon. | $^1$H Total Br/K* | $^{13}$C Total Br/K^ | Avg. Total Br/K |
|---|---|---|---|---|---|---|
| C9-1 | 14.9 | 13.0 | 14.0 | 26.3 | 10.9 | 18.6 |
| C9-2 | 10.5 | 9.5 | 10.0 | 25.8 | 14.9 | 20.4 |
| C9-3 | 13.3 | 11.7 | 12.5 | 25.8 | 13.5 | 19.7 |
| Average | 12.9 | 11.4 | 12.2 | 26.0 | 13.1 | 19.5 |

TABLE 12A-continued

\* Analysis complicated by cyclic olefinic endgroups.
^ $^{13}$C by $S_{\alpha\delta+}$ $CH_2$ adjacent to branch (37.1 ppm): C9-1, 14; C9-2, 21; C9-3, 16.

| Ex. No. | % Vinyl* | % 1,2-Disub* | % Trisub* | % V-dene* | $C_1$/K | $C_2$/K | $C_3$/K | $C_4^+$/K | $^1$H NMR $M_n$* |
|---|---|---|---|---|---|---|---|---|---|
| C9-1 | 23.7 | 54.1 | 19.0 | 3.1 | 8.8 | 1.1 | 0 | 1.0 | 10868 |
| C9-2 | 28.5 | 57.3 | 12.9 | 1.4 | 9.4 | 2.8 | 0.6 | 2.1 | 10728 |
| C9-3 | 22.1 | 50.0 | 27.9 | 0 | 9.9 | 1.7 | 0.6 | 1.3 | 8662 |
| Average | 24.8 | 53.8 | 19.9 | 1.5 | 9.4 | 1.9 | 0.4 | 1.5 | 10086 |

*Analysis complicated by cyclic olefinic endgroups.
1,2-Disub. includes some cyclics.

Comparative Example C10

Homopolymerization of ethylene using 1. The results in Tables 13 and 13A were obtained.

TABLE 13

| Ex. No. | Yield (g) | Activity (g/ mmol cat) | Activity (g/ mmol cat hr) | $M_w$ | $M_n$ | $M_w/M_n$ |
|---|---|---|---|---|---|---|
| C10-1 | 2.08 | 138.67 | 34.67 | 16,990 | 3,690 | 4.60 |
| C10-2 | 2.06 | 137.33 | 34.33 | 15,800 | 3,900 | 4.05 |
| C10-3* | 1.56 | 104.00 | 26.00 | 14,840 | 3,530 | 4.20 |
| Average^ | 2.07 | 138.00 | 34.5 | 16,400 | 3,800 | 4.33 |

*Did not stir properly.
^Does not include C10-3

TABLE 13A

| Ex. No. | $^1$H Total Br/K | $^{13}$C Total Br/K | Avg. Total Br/K | % Vinyl | % 1,2-Disub. | % Trisub. | % V-dene | $C_1$/K | $C_2$/K | $C_3$/K | $C_4^+$/K | $^1$H NMR $M_n$ | $^{13}$C NMR $M_n$ | Avg. NMR $M_n$ |
|---|---|---|---|---|---|---|---|---|---|---|---|---|---|---|
| C10-1 | 19.8 | 17.5 | 18.7 | 49.9 | 48.4 | 1.7 | 0 | 11.7 | 0.5 | 0.5 | 4.7 | 4169 | 3949 | 4059 |
| C10-2 | 19.6 | 15.7 | 17.7 | 50.4 | 44.9 | 4.6 | 0 | 10.9 | 0.9 | 0.2 | 3.7 | 4216 | 4144 | 4180 |
| C10-3* | 20.9 | 18.7 | 19.8 | 43.3 | 46.6 | 10.2 | 0 | 11.5 | 1.6 | 0.5 | 5.2 | 3711 | 3841 | 3776 |
| Average^ | 19.7 | 16.6 | 18.2 | 50.2 | 46.7 | 3.2 | 0 | 11.3 | 0.7 | 0.4 | 4.2 | 4193 | 4047 | 4120 |

*Did not stir properly.
^Does not include C10-3

Comparative Example C11

Homopolymerization of ethylene using C1. The results in Tables 14 and 14A were obtained.

TABLE 14

| Ex. No. | Yield (g) | Activity (g/ mmol cat) | Activity (g/ mmol cat hr) | $M_w$ | $M_n$ | $M_w/M_n$ |
|---|---|---|---|---|---|---|
| C11-1 | 2.404 | 160.27 | 40.07 | 12,760 | 2,780 | 4.59 |
| C11-2 | 2.446 | 163.07 | 40.77 | 16,580 | 2,870 | 5.78 |
| C11-3 | 2.708 | 180.53 | 45.13 | 16,970 | 3,280 | 5.17 |
| Average | 2.519 | 167.96 | 41.99 | 15,440 | 2,980 | 5.18 |

TABLE 14A

| Ex. No. | $^1$H Total Br/K | $^{13}$C Total Br/K | Avg. Total Br/K | % Vinyl | % 1,2-Disub. | % Trisub. | % V-dene | $C_1$/K | $C_2$/K | $C_3$/K | $C_4^+$/K | $^1$H NMR $M_n$ |
|---|---|---|---|---|---|---|---|---|---|---|---|---|
| C11-1 | 48.7 | 50.3 | 49.5 | 14.7 | 80.2 | 5.2 | 0 | 29.5 | 8.2 | 1.8 | 10.8 | 3287 |
| C11-2 | 44.6 | 46.7 | 45.7 | 14.5 | 85.3 | NA* | 0 | 27.7 | 7.5 | 1.6 | 9.9 | 4026 |
| C11-3 | 67.4^ | 41.4^ | 54.4 | 12.1 | 81.1 | 6.8 | 0 | 25.0 | 6.6 | 1.3 | 8.5 | 2042 |
| Average | 53.6 | 46.1 | 49.9 | 13.8 | 82.3 | 6.0 | 0 | 27.4 | 7.4 | 1.6 | 9.7 | 3118 |

*Interference from spectral artifact.
^Disagreement between methods.

| Comonomer | C2 only | C2/C8 | C2/NB | C2/C8—Ac | C2/C8—OSiMe$_3$^ | C2/C8—OH | C2/NB—Ac |
|---|---|---|---|---|---|---|---|
| Activity, g/mmol 1 | 138.00 | 133.56 | 24.67 | 43.56 | 46.67 | 3.56 | 3.67 |
| $M_w$ | 16,400 | 11,980 | 8,870 | 12,880 | 11,240 | 6,610 | 6,960 |
| $M_n$ | 3,800 | 3,700 | 4,010 | 3,950 | 3,750 | 2,630 | 3,720 |
| $M_w/M_n$ | 4.33 | 3.24 | 2.22 | 3.26 | 2.99 | 2.51 | 1.87 |
| $^1$H NMR $M_n$ | 4,120 | 4,050 | 3,070 | 4,300 | 4,030 | 3,330 | 4,450 |
| Comon mol % | — | 0.5 | 13.8 | 0.7 | 0.7 | 0.7 | 6.7 |
| Olefins* | 3.3 | 3.5 | 4.6 | 3.3 | 3.5 | 4.2 | 3.2 |
| Comon. units* | — | 2.5 | 51.3 | 3.4 | 3.4 | 3.4 | 28.7 |
| % V:1,2:Tri:VD | 50:47:3:0 | 44:51:5:0 | 36:35:29:1 | 50:45:5:0 | 50:45:5:0 | 55:43:3:0 | 59:41:0:0 |
| $C_1$:$C_2$:$C_3$:$C_4^+$* | 11:1:0:4 | 12:2:0:8 | 7:0:0:3 | 12:2:0:4 | 11:1:0:4 | 13:1:0:5 | — |
| Total $^1$H Br* | 19.7 | 24.5 | 25.6 | 18.4 | 19.9 | 23.0 | 15.1 |
| Total $^{13}$C Br* | 16.6 | 21.8 | 9.7 | 18.7 | 16.7 | 18.5 | — |

*Per 1000 C.
^As 7-octen-1-ol in polymer.
V = vinyl; 1,2 = 1,2-disubstituted;
Tri = trisubstituted;
VD = vinylidene.
C2 = ethylene,
C8 = 1-octene,
NB = norbornene,
C8—Ac = octenyl acetate,
C8—OSiMe$_3$ = 7-octen-1-ol trimethylsilyl ether,
C8—OH = 7-octen-1-ol,
NB—Ac = 5-norbonen-2-yl acetate.

| Comonomer | C2 only | C2/C8 | C2/NB | C2/C8—Ac | C2/C8—OSiMe$_3$^ | C2/C8—OH | C2/NB—Ac |
|---|---|---|---|---|---|---|---|
| Activity, g/mmol C1 | 167.96 | 177.78 | 46.51 | 30.91 | 44.89 | 0.87 | 6.69 |
| $M_w$ | 15,440 | 13,270 | 23,360 | 15,210 | 18,540 | 6,580 | 15,390 |
| $M_n$ | 2,980 | 2,880 | 12,420 | 6,900 | 8,260 | 3,300 | 8,410 |

-continued

| Comonomer | C2 only | C2/C8 | C2/NB | C2/ C8—Ac | C2/C8— OSiMe₃^ | C2/ C8—OH | C2/ NB—Ac |
|---|---|---|---|---|---|---|---|
| $M_w/M_n$ | 5.18 | 4.56 | 1.88 | 2.21 | 2.24 | 2.00 | 1.85 |
| ¹H NMR $M_n$ | 3,120 | 3,570 | 10,090 | 9,670 | 8,810 | 9,810 | 10,750 |
| Comon mol % | — | 1.0 | 12.2 | 1.0 | 0.7 | 0.9 | 6.8 |
| Olefins* | 4.5 | 3.9 | 1.4 | 1.5 | 1.6 | 1.4 | 1.3 |
| Comon. units* | — | 4.9 | 46.7 | 4.7 | 3.7 | 4.2 | 29.3 |
| % V:1,2:Tri:VD | 14:82:6:0 | 12:81:6:0 | 25:54:20:2 | 28:69:3:0 | 27:66:7:0 | 37:55:9:0 | 29:71:0:0 |
| $C_1:C_2:C_3:C_4$** | 27:7:2:10 | 25:7:2:15 | 9:2:0:2 | 17:3:1:3 | 15:1:0:2 | — | 10:0:0:0 |
| Total ¹H Br* | 53.6 | 47.9 | 26.0 | 22.3 | 20.9 | 24.1 | 16.4 |
| Total ¹³C Br* | 46.1 | 49.1 | 13.1 | 23.8 | 18.6 | — | 10.3 |

*Per 1000 C.
^As 7-octen-1-ol in polymer.
V = vinyl;
1,2 = 1,2-disubstituted;
Tri = trisubstituted;
VD = vinylidene.
C2 = ethylene,
C8 = 1-octene,
NB = norbornene,
C8—Ac = octenyl acetate,
C8—OSiMe₃ = 7-octen-1-ol trimethylsilyl ether,
C8—OH = 7-octen-1-ol, NB—Ac = 5-norbornen-2-yl acetate.

Example 7

Comparison of retention of activity and comonomer incorporation upon introduction of functional groups for 1 and C1. Table 17 shows average catalyst activity for 1 and C1 in the presence of polar comonomers, as a percentage of the base activity seen with the unfunctionalized monomer of similar structure (e.g., octenyl acetate to 1-octene). Table 17 also shows comonomer incorporation for 1 and C1, as a percentage of the base incorporation seen with the unfunctionalized monomer. Azo-phenoxide 1 gives less severe activity drops upon functionalization of an octene or norbornene comonomer framework than imine-phenoxide C1. For the case of octene-based functional comonomers, an increase in comonomer incorporation in seen with 1, rather than a decrease as is seen for C1.

| Copoly- merization | Average Activity, g PE/mmol cat (% of base) | | Average Comonomer Incorporation, mol % (% of base) | |
|---|---|---|---|---|
| | 1 | C1 | 1 | C1 |
| C2/C8 (base case) | 133.56 | 177.78 | 0.5 | 1.0 |
| C2/C8—Ac | 43.56 (33%) | 30.91 (17%) | 0.7 (140%) | 1.0 (100%) |
| C2/C8—OH | 3.56 (3%) | 0.87 (0.5%) | 0.7 (140%) | 0.9 (90%) |
| C2/C8-OSiMe₃^ | 46.67 (35%) | 44.89 (25%) | 0.7 (140%) | 0.7 (70%) |
| C2/NB (base case) | 24.67 | 46.51 | 13.8 | 12.2 |

-continued

| Copoly- merization | Average Activity, g PE/mmol cat (% of base) | | Average Comonomer Incorporation, mol % (% of base) | |
|---|---|---|---|---|
| | 1 | C1 | 1 | C1 |
| C2/NB—Ac | 3.67 (15%) | 6.69 (14%) | 6.7 (49%) | 6.8 (55%) |

^ As 7-octen-1-ol in polymer.
C2 = ethylene,
C8 = 1-octene,
NB = norbornene,
C8—Ac = octenyl acetate,
C8—OSiMe₃ = 7-octen-1-ol trimethylsilyl ether,
C8—OH = 7-octen-1-ol,
NB—Ac = 5-norbornen-2-yl acetate.

Example 8

Comparison of retention of copolymer molecular weight upon introduction of functional groups for 1 and C1. Table 18 shows average copolymer weight-average molecular weight (Mw) for 1 and C1 in the presence of polar comonomers, as a percentage of the base Mw seen with the unfunctionalized monomer of similar structure. Mw values for functional copolymers are not directly comparable to those for base unfunctionalized (C2/C8 or C2/NB) copolymers due to changes in refractive index. However, as copolymer compositions are roughly similar between 1 and C1 for each particular comonomer, Mw values/percentages for each can be compared between the two catalysts. The reduction in copolymer Mw upon adding an acetate functionality to a norbornene monomer is less severe for 1 than for C1. A similar (but smaller) advantage for 1 exists upon addition of an alcohol group to an octene comonomer.

TABLE 18

Mw and Mw retention (in %) for polar monomers vs. analogous unfunctionalized monomers for 1 and C1 (toluene solvent, 4 h, 50° C., 120 psig $C_2H_4$ (827 kPa)).

| Copolymerization | Average $M_w^a$ (% of base) | |
|---|---|---|
|  | 1 | C1 |
| C2/C8 (base case) | 11,980 | 13,270 |
| C2/C8—Ac | 12,880 (108%) | 15,210 (115%) |
| C2/C8—OH | 6,610 (55%) | 6,580 (50%) |
| C2/C8—OSiMe$_3^\wedge$ | 11,240 (94%) | 18,540 (140%) |
| C2/NB (base case) | 8,870 | 23,360 |
| C2/Nb—Ac | 6,960 (87%) | 15,390 (66%) |

$^\wedge$As 7-octen-1-ol in polymer.
$^a$DRI, vs. polyethylene standards, in 1,2,4-trichlorobenzene at 135° C. Percentages greater than 100 most likely reflect changes in refractive index rather than actual increases in Mw.
C2 = ethylene,
C8 = 1-octene,
NB = norbornene,
C8—Ac = octenyl acetate,
C8—OSiMe$_3$ = 7-octen-1-ol trimethylsilyl ether,
C8—OH = 7-octen-1-ol,
NB—Ac = 5-norbornen-2-yl acetate.

Example 9

Comparison of alkyl branches per 1000 carbons and vinyl endgroup content for ethylene/polar monomer copolymers made with 1 and C1. Table 19 shows the average total alkyl branch content, and percent of endgroups that are vinyl structures, for ethylene/polar monomer copolymers made with 1 and C1. The functional copolymers prepared with 1 have fewer alkyl branches than those prepared with C1, and also have a greater percentage of their olefin endgroups as vinyls.

TABLE 19

Total alkyl branches (per 1000 carbons) and vinyl endgroup content (as %) for ethylene/polar monomer copolymers made with 1 and C1 (toluene solvent, 4 h, 50° C., 120 psig $C_2H_4$ (827 kPa)).

| Copolymerization | Average Br/ 1000 C$^a$ | | Average % Vinyls$^b$ | |
|---|---|---|---|---|
|  | 1 | C1 | 1 | C1 |
| C2/C8—Ac | 18.4 | 22.3 | 49.9 | 27.9 |
| C2/C8—OH | 23.0 | 24.1 | 54.8 | 36.6 |
| C2/C8—OSiMe$_3^\wedge$ | 19.9 | 20.9 | 50.2 | 26.7 |
| C2/Nb—Ac | 15.1 | 16.4 | 59.0 | 28.9 |

$^\wedge$As 7-octen-1-ol in polymer.
$^a$By $^1$H NMR; represents all alkyl branches regardless of length.
$^b$By $^1$H NMR, as per cent of total olefins (vinyl; 1,2-disubstituted; trisubstituted; vinylidene).
C2 = ethylene,
C8 = 1-octene,
NB = norbornene,
C8—Ac = octenyl acetate,
C8—OSiMe$_3$ = 7-octen-1-ol trimethylsilyl ether,
C8—OH = 7-octen-1-ol,
NB—Ac = 5-norbornen-2-yl acetate.

Example 10

Synthesis of ethylene/5-norbornen-2-ol copolymer via copolymerization of ethylene/5-norbornen-2-yl acetate using 1. A set of three triplicate copolymerizations similar to Example 6 were carried out, using a polar monomer feed of 2 mmol (0.13 M) 5-norbornen-2-yl acetate per cell instead of 6 mmol. After isolation and weighing, the three separate batches of copolymer were combined for compositional analysis. In a 250 mL 3-necked 24/40 round bottom flask equipped with a mechanical stirrer and a reflux condenser, 1.7 g of the copolymer was dissolved in 50 mL toluene. Using an addition funnel, a solution of 150 mg KOH dissolved in 20 mL methanol/1 mL H$_2$O was added dropwise to the stirred solution over a 30 minute period under N$_2$. The mixture was stirred overnight at 118° C. and the product polymer (polyethylene-co-5-norbornen-2-ol) was subsequently precipitated into methanol, washed, filtered, dried, and characterized similarly to previous examples (1.6 g). IR (KBr pellet): 3332 cm$^{-1}$ (w, O—H); no C=O stretch at 1700-1600 cm$^{-1}$. The results in Tables 20 and 20A were obtained.

Tables 20 and 20A (Example 10)—Ethylene/5-norbornen-2-yl acetate copolymerization with 1 and hydrolysis of product to ethylene/5-norbornen-2-ol copolymer.

TABLE 20

| Ex. No. | Yield (g) | Activity (g/mmol cat) | Activity (g/mmol cat hr) | $M_w$ | $M_n$ | $M_w/M_n$ | $^1$H mol % comon. |
|---|---|---|---|---|---|---|---|
| 10-1 | 0.65 | 43.33 | 10.83 |  |  |  |  |
| 10-2 | 0.582 | 38.80 | 9.70 |  |  |  |  |
| 10-3 | 0.542 | 36.13 | 9.03 |  |  |  |  |
| Average | 0.591 | 39.42 | 9.86 | 9,800* | 4,430* | 2.22* | 1.9* |

*Samples were combined for characterization and hydrolysis.

TABLE 20A

| Ex. No. | $^1$H Total Br/K | % Vinyl | % 1,2-Disub. | % Trisub. | % V-dene | $^1$H endo | $^1$H exo | endo:exo |
|---|---|---|---|---|---|---|---|---|
| Avg* | 13.1 | 56.0 | 44.0 | 0 | 0 | 1.3 | 0.6 | 69:31 |

*Samples were combined for characterization and hydrolysis.

For the examples below, NMR characterization of ethylene/5-norbornen-2-ol copolymers was carried out similarly to the analyses previously described for other copolymers. $^1$H NMR copolymer composition was determined using the C$\underline{H}$OH resonances at 4.4 (endo) and 3.9 (exo) ppm. $^{13}$C NMR copolymer composition was determined using the $\underline{C}$HOH resonances at 75.4 ppm (exo) and 73 ppm (endo). $^{13}$C NMR alkyl branching per 1000 carbons does not include chain ends and was determined by summing contributions from 1B$_1$ methyls (20 ppm) and 1B$_{3+}$ branch methyls (14.1 ppm, after subtracting contributions from linear methyl chain ends as measured by the 2 s methylene peak at 22.9 ppm; no 1B$_2$ methyls were detected). Differential scanning calorimetry (DSC) was carried out on a TA Instruments 2920 calorimeter using a scan rate of 10 degrees per minute. Melting point (T$_m$) values are maxima derived from second heats. Molecular weights (Mw, Mn, Mw/Mn) were measured as previously described for other copolymers. 5-Norbornen-2-ol (Aldrich Chemical Co.) was purified prior to use by dissolution in hot, dry hexanes, followed by filtration and recrystallization at –40° C.

Example 11

Ethylene/5-norbornen-2-yl acetate copolymerization with azo-phenoxide catalyst 1 at lower ethylene pressure.

In a drybox, a 300 cc Hasteloy C Parr reactor bottom was charged with 2.23 g (14.6 mmol) of 5-norbornen-2-yl acetate, 70 mL dry toluene, and 20 mL dry diethyl ether. Separately, 56.5 mg (0.065 mmol) of 1 was dissolved in 10 mL dry toluene in a scintillation vial. This solution was loaded into an airtight 10 mL syringe and kept in the drybox until immediately before use. The reactor was sealed with a head apparatus featuring a mechanical stirring paddle and a catalyst injection valve and removed from the drybox. The contents of the reactor were pressurized with 100 psig ethylene (690 kPa), stirred for 3 minutes, and the reactor was vented and heated to 40° C. The catalyst solution was then injected into the reactor, which was pressurized to a constant 50 psig (348 kPa) using a pressure vessel tank (PVT) and stirred for 2 hours. Subsequently, the reactor was vented and cooled, and 5 mL methanol was added via syringe to terminate polymerization. The contents of the reactor were added to an excess of methanol, and the solid polymer was collected by filtration, washed with additional clean methanol, and dried in a vacuum oven overnight at 60 C. Results are given in Tables 21 and 21A.

Comparative Example C12

Ethylene/5-norbornen-2-yl acetate copolymerization with imine-phenoxide catalyst C1 at lower ethylene pressure. This procedure was carried out in a similar manner to Example 11 except that the initial charge of ethylene was held for 5 minutes prior to venting. The amounts of reagents used were: 53 mg (0.062 mmol) C1 in 5 mL toluene (catalyst solution); 2.23 g (14.6 mmol) 5-norbornen-2-yl acetate, 75 mL toluene, and 20 mL diethyl ether (in Parr). Results are given in Tables 21 and 21A.

Example 12

Ethylene/5-norbornen-2-ol copolymerization with azo-phenoxide catalyst 1 at lower ethylene pressure. This procedure was carried out in a similar manner to Example 11 except that the initial charge of ethylene (prior to venting) was 50 psig. The amounts of reagents used were 43.5 mg (0.05 mmol) azo-phenoxide 1 in 10 mL toluene (catalyst solution); 1.58 g (14.4 mmol) 5-norbornen-5-ol, 54 mL toluene, and 16 mL diethyl ether (in Parr). Results are given in Tables 21 and 21A.

Comparative Example C13

Ethylene/5-norbornen-2-ol copolymerization with imine-phenoxide catalyst C1 at lower ethylene pressure. This procedure was carried out in a similar manner to Example 11 except that the initial charge of ethylene was held for 5 minutes prior to venting. The amounts of reagents used were: 55 mg (0.065 mmol) C1 in 5 mL toluene (catalyst solution); 2.0 g (18.2 mmol) 5-norbornen-2-ol, 75 mL toluene, and 20 mL diethyl ether (in Parr). Results are given in Tables 21 and 21A.

Tables 21 and 21A Ethylene copolymerization with 5-norbornen-2-yl acetate (NB—Ac) or 5-norbornen-2-ol (NB—OH) using 1 and C1 (40° C., 50 psig C$_2$H$_4$ (348 kPa), 2 h).

| Ex. No. | Catalyst (mmol) | Comonomer (mmol) | Solvent | Yield (g) | Activity (g PE/ mmol cat) | Mol % comon. |
|---|---|---|---|---|---|---|
| 11 | 1 (0.065) | NB—Ac (14.6) | 80 mL toluene 20 mL Et$_2$O | 0.9 | 13.8 | 5.9[a] |
| C12 | C1 (0.062) | NB—Ac (14.6) | 80 mL toluene 20 mL Et$_2$O | 1.61 | 26.0 | 3.7[a] |
| 12 | 1 (0.050) | NB—OH (14.4) | 64 mL toluene 16 mL Et$_2$O | 0.26 | 5.2 | 7.0[b] |

| Ex. No. | | | -continued | | | |
|---|---|---|---|---|---|---|
| C13 | C1 (0.065) | NB—OH (18.2) | 80 mL toluene 20 mL Et$_2$O | 0.63 | 97 | 6.3[b] |

[a] By $^{13}$C NMR.
[b] By average of $^1$H and $^{13}$C NMR.

Table 21A

| Ex. No. | endo:exo | Alkyl Br/ 1000 C[c] | Mw/Mn (PDI)[d] | $T_m$[e] (° C.) |
|---|---|---|---|---|
| 11 | 76:24[e] | 13.6 | 4,560/2,420 (1.9) | 72.1 v. broad |
| C12 | NA | 11.6[f] | 19,780/7,580 (2.6) | 90.3 broad, lo-temp shoulder |
| 12 | 74:26[b] | 14.5 | 3,290/1,600 (2.1) | 77.6 broad, lo-temp shoulder |
| C13 | 72:28[a] | 13.7[f] | 9,980/5,640 (1.8) | 83.6 v. broad |

[a] By $^1$H NMR.
[b] By average of $^1$H and $^{13}$C NMR.
[c] By $^{13}$C NMR; linear chain ends not included.
[d] DRI, vs. polyethylene standards, in 1,2,4-trichlorobenzene at 135° C.
[e] 2$^{nd}$ Heat maxima.
[f] Only C$_1$ branches detected.

Tables 17-19 (Examples 7-9) and 21 (Examples 11-12) serve to illustrate some of advantages of E-phenoxide catalysts for the copolymerization of olefins with polar monomers. Many known olefin polymerization catalysts show large and undesirable decreases in efficiency, as measured by reduced activity and polymer molecular weight, upon the introduction of polar monomers to the feed. Azo-phenoxide 1 gives less severe activity drops upon the addition of functionality to an octene or norbornene comonomer framework than imine-phenoxide C1 at 50° C. and 120 psig C$_2$H$_4$ (827 kPa). At these conditions, azo-phenoxide 1 also shows smaller decreases in polymer Mw upon the addition of some functionalities to an octene or norbornene comonomer framework as compared to C1. Additionally, at 40° C. and 50 psig ethylene (348 kPa), 1 gives greater incorporation of 5-norbornen-2-yl acetate and 5-norbornen-2-ol than C1. Thus, on a relative basis, azo-phenoxide catalyst 1 can exhibit greater activity to polar monomers, or retain more of its desirable properties for the preparation of olefin polymers, than a similar imine-phenoxide catalyst (C1).

Additionally, at 50° C. and 120 psig C$_2$H$_4$ (827 kPa), the functional copolymers prepared with 1 have slightly fewer alkyl branches than those prepared with C1 and also have a greater percentage of their olefin endgroups as vinyls. Reduced alkyl branching is desirable because many polymer properties (including melting point and crystallinity) are degraded by the presence of branches, whereas greater vinyl endgroup content presents an advantage for the potential use of the functional copolymers prepared with 1 as macromonomers.

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

The invention calaimed is:

1. A polymerization method comprising contacting one or more polar monomers and one or more olefin monomers with a catalyst system comprising: 1) optionally, an activator, and 2) a catalyst composition represented by the formula:

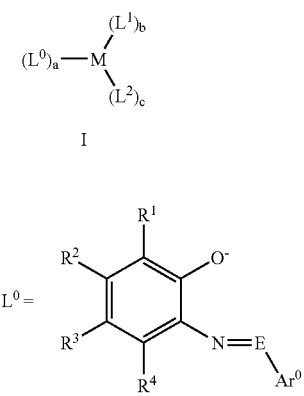

I wherein

M is selected from groups 3-11 of the periodic table;
E is nitrogen or phosphorus;
Ar$^0$ is arene;
R$^1$-R$^4$ are, each independently, selected from hydrogen, hydrocarbyl, substituted hydrocarbyl or functional group, provided however that R$^3$ and R$^4$ do not form a naphthyl ring;
L$^1$ represents a formal anionic ligand,
L$^2$ represents a formal neutral ligand,
a is an integer greater than or equal to 1;
b is an integer greater than or equal to 0; and
c is an integer greater than or equal to 1.

2. The method of claim 1 wherein M is a group 4 or 10 metal.

3. The method of claim 1 wherein M is titanium or nickel.

4. The method of claim 1 wherein E is nitrogen.

5. The method of claim 1 wherein a is 1, 2, 3, or 4.

6. The method of claim 1 wherein a is 1 or 2.

7. The method of claim 1 wherein b is 0, 1 or 2 and c is 1 or 2.

8. The method of claim 1 wherein $Ar^0$ is selected from the group consisting of ZETA-ARENES.

9. The method of claim 1 further comprising an activator.

10. The method of claim 1 wherein
each $L^2$ is, independently, selected from the group consisting of ethers, ketones, esters, alcohols, carboxylic acids, amines, imines, azo, nitriles, heterocycles, phosphines, thioethers, alkyls, alkenes, alkynes, arenes and combinations thereof;
each $L^1$ is, independently, selected from the group consisting of hydrides, fluorides, chlorides, bromides, iodides, alkyls, aryls, alkenyls, alkynyls, allyls, benzyls, acyls, trimethylsilyls and combinations thereof; and
$Ar^0$ is selected from the group consisting of substituted or unsubstituted heterocyclics, polyheterocyclics, heterocyclic ring assemblies, fused heterocyclic ring systems or combinations thereof.

11. The method of claim 10 wherein M is nickel or titanium.

12. The method of claim 11 wherein a=1 or 2, b=0, 1 or 2, and c=1 or 2.

13. The method of claim 10 further comprising an activator.

14. The method of claim 1 wherein $L^1$ is selected from the group consisting of ZETA-FORMAL ANIONIC LIGANDS, and $L^2$ is selected from the group consisting of ZETA-FORMAL NEUTRAL LIGANDS.

15. The method of claim 1 wherein $L^1$ is selected from the group consisting of —F, —Cl, —Br, —I, —N(CH$_3$)$_2$, —OCH$_3$, —H, —CH$_3$, —C$_6$H$_5$, -allyl, -benzyl, —CH$_2$Si(CH$_3$)$_3$.

16. The method of claim 1 wherein the catalyst composition is represented by one of the following formulae:

| $(L^0)_a(L^1)_{b-2}(L^2)_cM(R^5)_2$ | $(L^0)_a(L^1)_{b-2}(L^2)_cM(R^5)_1(L^3)_1$ | $(L^0)_a(L^1)_{b-2}(L^2)_cM(L^3)_2$ |
|---|---|---|
| 2 | 3 | 4 |
| $(L^0)_a(L^2)_cM$ | $(L^0)_a(L^1)_{b-1}(L^2)_cM(R^5)_1$ | $(L^0)_a(L^1)_{b-1}(L^2)_cM(L^3)_1$ |
| 5 | 6 | 7 | wherein:
M is selected from groups 3-11 of the periodic table,
$L^0$ represents an E-phenoxide ligand represented by the formula:

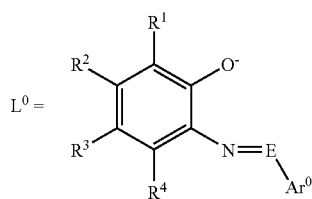

$L^1$ represents a formal anionic ligand;
$L^2$ represents a formal neutral ligand;
$L^3$ represents a formal anionic ligand that comprises a functional group;
a is 1, 2, 3 or 4;
b is 0, 1, 2, 3, 4, 5 or 6, provided that b is not 0 or 1 in formula 2, 3 or 4 and b is not 0 in formula 6 or 7;
c is 1, 2, 3 or 4;

E is nitrogen or phosphorus;
$Ar^0$ is an arene selected from the group consisting of ZETA-ARENES;
$R^1$-$R^4$ are each independently hydrogen, a hydrocarbyl, a substituted hydrocarbyl or a functional group, provided that $R^3$ and $R^4$ do not form a naphthyl ring; and
$R^5$ is a hydride, a hydrocarbyl or a substituted hydrocarbyl.

17. The method of claim 16 wherein E is nitrogen and M is titanium or nickel.

18. The method of claim 1 wherein the catalyst composition is represented by one of the following formulae:

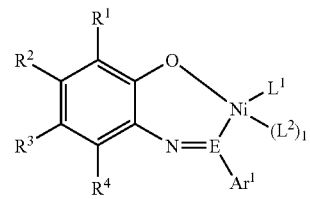

8

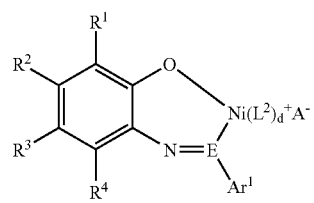

9

-continued

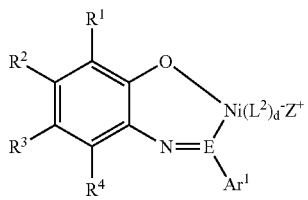

10

E is nitrogen or phosphorus;
$Ar^1$ is selected from the group consisting of:

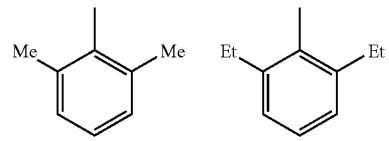

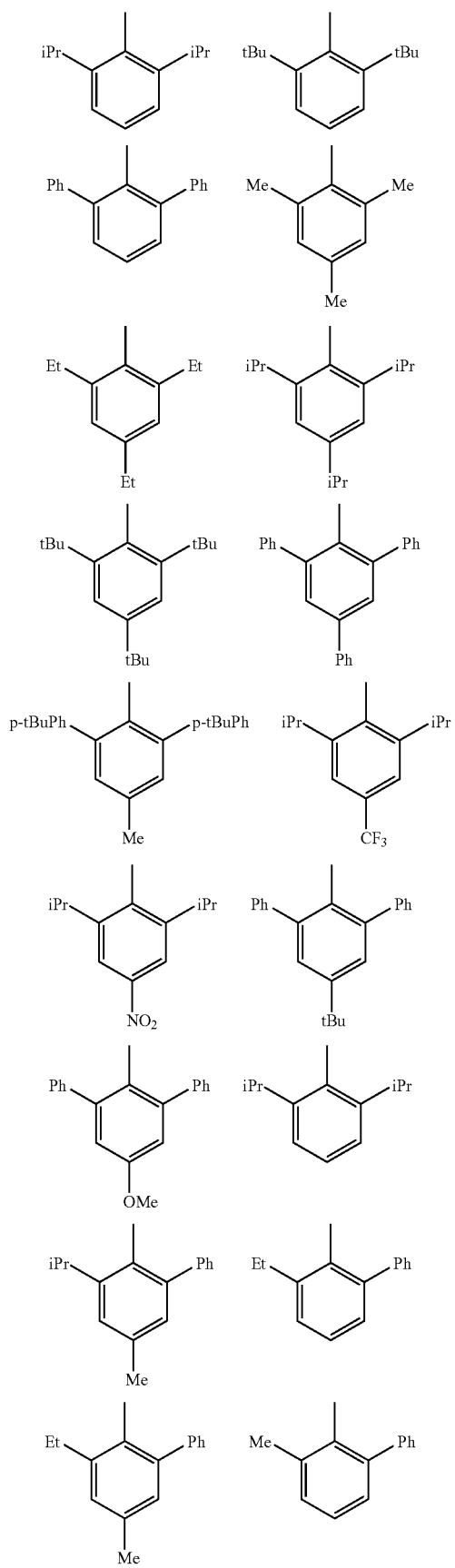
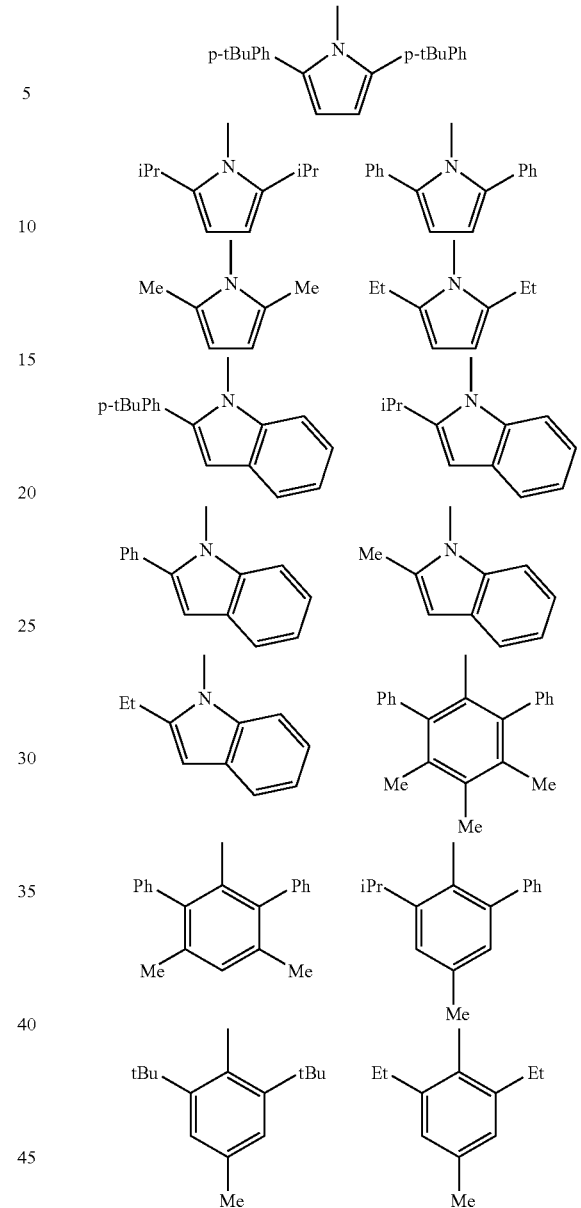

$R^1$-$R^4$ are each independently hydrogen, a hydrocarbyl, a substituted hydrocarbyl or a functional group, provided that $R^3$ and $R^4$ do not form a naphthyl ring;

$L^1$ represents a formal anionic ligand selected from the group consisting of ZETA-FORMAL ANIONIC LIGANDS;

$L^2$ represents a formal neutral ligand selected from the group consisting of ZETA-FORMAL NEUTRAL LIGANDS;

"d" is 1, 2 or 3;

$A^-$ is an anion that may or may not coordinate to Ni; and $Z^+$ is a cation selected from the group consisting of metals or metal complexes of groups 1, 2, 11, and 12, where Me is methyl, Et is ethyl, iPr is isopropyl, tBu is tertiary butyl, Ph is phenyl, p-t-BuPh is para-tertiary-butylphenyl.

19. The method of claim 18 wherein A⁻ is a non-coordinating anion.

20. The method of claim 18 wherein A⁻ is selected from the group consisting of halides, carboxylates, phosphates, sulfates, sulfonates, borates, aluminates, alkoxides, thio-alkoxides, anonic substituted hydrocarbons, and anionic metal complexes.

21. The method of claim 1 wherein the catalyst composition is represented by formula:

11

[Structure: azo-phenoxide nickel complex with $R^6$, $R^3$ substituents on phenol ring, O coordinated to Ni with $L^1$ and $L^4$ ligands, N=N linkage to $Ar^1$]

wherein $L^1$ represents a formal anionic ligand;

$R^3$ is hydrogen, a hydrocarbyl, a substituted hydrocarbyl or a functional group;

$R^6$ is $C(R^7)_e$, e is 2 or 3, $R^7$ is a hydrocarbon, a substituted hydrocarbon, or a functional group, two $R^7$ groups may be part of a common arene ring when e is 2;

$Ar^1$ is an arene; and $L^4$ is a formal neutral ligand, coordinated to the nickel in addition to the nitrogen of the azo-phenoxide ligand.

22. The method of claim 21 wherein $L^4$ selected from the group consisting of:

$P(C_6H_5)_3$   $P(C_{10}H_7)_3$   $NC-CH_3$   $NC-C_5H_3(CF_3)_2$   $CH_2=CH_2$

[Structures: 2,6-lutidine; 2-bromopyridine; pyridine]

$Me_3P=CH_2$ where Me is methyl.

23. The method of claim 22 wherein $R^6$ is selected from the group consisting of t-butyl, adamantyl, phenyl, naphthyl, and anthracenyl.

24. The method of claim 1 wherein the catalyst composition is represented by the formula:

12

[Structure: azo-phenoxide nickel complex with Me and $Ar^3$ substituents on phenol ring, O coordinated to Ni with $R^8$ and $L^4$ ligands, N=N linkage to $Ar^2$]

wherein:

$L^4$ represents a formal neutral ligand based on carbon, nitrogen or phosphorus;

$R^8$ represents a formal anionic ligand which may be hydrogen or a hydrocarbyl;

$Ar^2$ is a phenyl group independently substituted in the 2 and 6 positions by secondary hydrocarbons, secondary substituted hydrocarbons, tertiary hydrocarbons, tertiary substituted hydrocarbons, or arenes $Ar^2$ is an arene;

$Ar^3$ is an arene; and

Me is methyl.

25. The method of claim 24 wherein $Ar^2$ is selected from the group consisting of:

[Structures: 2,6-diisopropyl-3-methylphenyl; 2,6-di-tert-butyl-3-methylphenyl; 2,6-diphenyl-3-methylphenyl]

where iPr is isopropyl, tBu is tertiary butyl and Ph is phenyl.

26. The method of claim 24 wherein $Ar^3$ is selected from the group consisting of:

[Structures: toluene; 4-trifluoromethyltoluene; 4-nitrotoluene; 3,5-bis(trifluoromethyl)toluene; 3,5-dinitro-trifluoromethylbenzene; pentafluorotoluene; methylnaphthalene; methylnaphthalene; fluorinated methylnaphthalene; fluorinated methylnaphthalene; methylanthracene; 4-methylpyridine; 4-methylpyridinium]

-continued

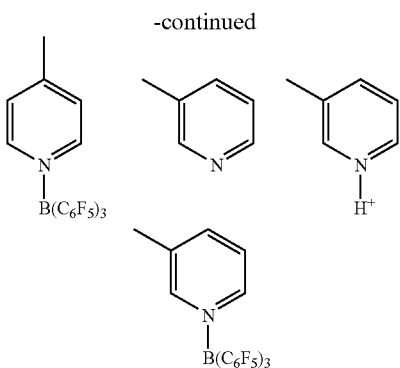

27. The method of claim 24 wherein $R^8$ is selected from the group consisting of hydrogen, a hydride, methyl, ethyl, trimethylsilylmethyl, trimethylsilyl, phenyl, naphthyl, allyl and benzyl.

28. The method of claim 1 wherein the catalyst composition is represented by the formula:

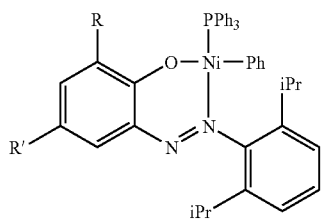

where R is anthracene and R' is methyl or tertiary butyl, iPr is isopropyl and Ph is phenyl.

29. The method of claim 1 wherein the olefin monomer comprises a C2 to C40 olefin monomer and the polar monomer is selected from the group consisting of carbon monoxide, 3-buten-1-ol, 2-methyl-3-buten-1-ol, 3-butene-1,2-diol, 4-penten-1-ol, 4-pentene-1,2-diol, 5-hexen-1-ol, 5-hexene-1,2-diol, 6-hepten-1-ol, 6-heptene-1,2-diol, 7-octen-1-ol, 7-octene-1,2-diol, 8-nonen-1-ol, 8-nonene-1,2-diol, 9-decen-1-ol, 9-decene-1,2-diol, 10-undecen-1-ol, 10-undecene-1,2-diol, 11-dodecen-1-ol, 11-dodecene-1,2-diol, 12-tridecen-1-ol, 12-tridecene-1,2-diol, 4-(3-butenyl)-2,2-dimethyldioxolane, 1,2-epoxy-3-butene (butadiene monoxide), 2-methyl-2-vinyloxirane, 1,2-epoxy-4-pentene, 1,2-epoxy-5-hexene, 1,2-epoxy-6-heptene, 1,2-epoxy-7-octene, 1,2-epoxy-8-nonene, 1,2-epoxy-9-decene, 1,2-epoxy-10-undecene, 1,2-epoxy-11-dodecene, 1,2-epoxy-12-tridecene, 3-buten-1-ol methyl ether, 4-penten-1-ol methyl ether, 5-hexen-1-ol methyl ether, 6-hepten-1-ol methyl ether, 7-octen-1-ol methyl ether, 8-nonen-1-ol methyl ether, 9-decen-1-ol methyl ether, 10-undecen-1-ol methyl ether, 11-dodecen-1-ol methyl ether, 12-tridecen-1-ol methyl ether, 4-pentenoic acid, 2,2-dimethyl-4-pentenoic acid, 5-hexenoic acid, 6-heptenoic acid, trans-2,4-pentadienoic acid, 2,6-heptadienoic acid, 7-octenoic acid, 8-nonenoic acid, 9-decenoic acid, 10-undecenoic acid, 11-dodecenoic acid, 12-tridecenoic acid, methyl 4-pentenoate, methyl 5-hexenoate, methyl 6-heptenoate, methyl 7-octenoate, methyl 8-nonenoate, methyl 9-decenoate, methyl 10-undecenoate, ethyl 10-undecenoate, methyl 11-dodecenoate, methyl 12-tridecenoate, 3-butenyl acetate, pentenyl acetate, hexenyl acetate, heptenyl acetate, octenyl acetate, nonenyl acetate, decenyl acetate, undecenyl acetate, dodecenyl acetate, tridecenyl acetate, 4-pentene-1-nitrile, 5-hexene-1-nitrile, 6-heptene-1-nitrile, 7-octene-1-nitrile, 8-nonene-1-nitrile, 9-decene-1-nitrile, 10-undecene-1-nitrile, 11-dodecene-1-nitrile, 12-tridecene-1-nitrile, 3-buten-1-ol trimethylsilyl ether, 4-penten-1-ol trimethylsilyl ether, 5-hexen-1-ol trimethylsilyl ether, 6-hepten-1-ol trimethylsilyl ether, 7-octen-1-ol trimethylsilyl ether, 8-nonen-1-ol trimethylsilyl ether, 9-decen-1-ol trimethylsilyl ether, 10-undecen-1-ol trimethylsilyl ether, 11-dodecen-1-ol trimethylsilyl ether, 12-tridecen-1-ol trimethylsilyl ether, 2,2-dimethyl-4-pentenal, undecylenic aldehyde, 2,4-dimethyl-2,6-heptadienal, 5-hexen-2-one, nonafluoro-1-hexene, 5-norbornene-2-carbonitrile, 5-norbornene-2-carboxaldehyde, 5-norbornene-2-carboxylic acid, cis-5-norbornene-endo-2,3-dicarboxylic acid, cis-5-norbornene-2-endo-3-exo-dicarboxylic acid, 5-norbornene-2-carboxylic acid methyl ester, cis-5-norbornene-endo-2,3-dicarboxylic anhydride, cis-5-norbornene-exo-2,3-dicarboxylic anhydride, 5-norbornene-2-endo-3-endo-dimethanol, 5-norbornene-2-endo-3-exo-dimethanol, 5-norbornene-2-exo-3-exo-dimethanol, 5-norbornene-2,2,-dimethanol, 5-norbornene-2-methanol, 5-norbornen-2-ol, 5-norbornen-2-ol trimethylsilyl ether, 5-norbornen-2-ol methyl ether, 5-norbornen-2-yl acetate, 1-[2-(5-norbornene-2-yl)ethyl]-3,5,7,9,11,13,15-heptacyclopentylpentacyclo[9.5.1.1$^{3,9}$.1$^{5,15.17,13}$]octasiloxane, 2-benzoyl-5-norbornene, tricyclo[4.2.1.0$^{0,0}$,]non-7-ene-3-carboxylic acid tert-butyl ester, tricyclo[4.2.1.0$^{0,0}$] non-7-ene-3,4-dicarboxylic acid tert-butyl ester, tricyclo[4.2.1.0$^{0,0}$]non-7-ene-3,4-dicarboxylic acid anhydride, N-butyl-tricyclo[4.2.1.0$^{0,0}$]non-7-ene-3,4-dicarboxyimide, 2-cyclopenten-1-one ethylene ketal, and vinylene carbonate.

30. The method of claim 1 in which the olefin monomer is ethylene and the polar monomer is 7-octen-1-ol.

31. The method of claim 1 in which the olefin monomer is ethylene and the polar monomer is 7-octen-1-ol trimethylsilyl ether.

32. The method of claim 1 in which the olefin monomer is ethylene and the polar monomer is octenyl acetate.

33. The method of claim 1 in which the olefin monomer is ethylene and the polar monomer is 5-norbornen-2-yl acetate.

34. The method of claim 1 in which the olefin monomer is ethylene and the polar monomer is 5-norbornen-2-ol and or norbornen-2-ol trimethylsilyl ether.

35. The method of claim 1 in which the catalyst composition comprises [2-(2',6'-Diisopropylphenylazo)-4-methyl-6-(9-anthracenyl)phenoxide]-Nickel(phenyl)(triphenylphosphine).

36. The method of claim 29 in which the catalyst composition comprises [2-(2',6'-Diisopropylphenylazo)-4-methyl-6-(9-anthracenyl)phenoxide]-Nickel(phenyl)(triphenylphosphine).

37. The method of claim 1 wherein the polar monomer is present in the polymer at 0.2 to 30 mole %.

38. The method of claim 1 wherein the polar monomer is present in the polymer at 0.2 to 15 mole %.

39. The method of claim 1 wherein the polar monomer is present in the polymer at 5 to 15 mole %.

40. The method of claim 1 wherein the polymerization is conducted at a temperature of 40° C. or more.

41. The method of claim 1 wherein the polymerization is conducted at a temperature of 50° C. or more.

42. The method of claim 1 wherein the polymerization is conducted at a pressure of 0.1 MPa or more.

43. The method of claim 1 wherein the polymerization is conducted at a pressure of 0.25 MPa or more.

44. The method of claim 1 wherein the polymerization is conducted in the presence of a solvent or diluent.

45. The method of claim 1 wherein the polymerization is conducted in the presence of a solvent or diluent where the solvent or diluent comprises a mixture of a polar solvent or diluent and a non-polar solvent or diluent.

46. The method of claim 1 wherein the polymerization is conducted at a temperature above 70° C. and a pressure above 5 MPa.

47. The method of claim 1 wherein the polymerization is conducted in the gas phase.

48. The method of claim 1 wherein the polymerization is conducted in the slurry phase.

49. The method of claim 1 wherein the polymerization is conducted in the solution phase.

50. The method of claim 1 wherein the polymerization is conducted in the presence of a mixture of toluene and diethyl ether.

* * * * *